United States Patent
Karbowniczek et al.

(10) Patent No.: US 9,993,184 B2
(45) Date of Patent: Jun. 12, 2018

(54) LANCET DEVICE

(71) Applicant: Becton, Dickinson and Company, Franklin Lakes, NJ (US)

(72) Inventors: Jacek Grzegorz Karbowniczek, Warsaw (PL); Wlodzimierz Rutynowski, Warsaw (PL)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days. days.

(21) Appl. No.: 14/543,168

(22) Filed: Nov. 17, 2014

(65) Prior Publication Data

US 2015/0073464 A1    Mar. 12, 2015

Related U.S. Application Data

(60) Continuation of application No. 13/669,792, filed on Nov. 6, 2012, now Pat. No. 8,998,942, which is a
(Continued)

(51) Int. Cl.
*A61B 17/14* (2006.01)
*A61B 17/32* (2006.01)
(Continued)

(52) U.S. Cl.
CPC .......... *A61B 5/1411* (2013.01); *A61B 5/1513* (2013.01); *A61B 5/150022* (2013.01);
(Continued)

(58) Field of Classification Search
CPC .............. A61B 5/1411; A61B 5/15186; A61B 5/15142; A61B 17/32093; A61B 5/151;
(Continued)

(56) References Cited

U.S. PATENT DOCUMENTS

| 3,741,197 A | 6/1973 | Sanz et al. |
| 4,194,505 A | 3/1980 | Schmitz |

(Continued)

FOREIGN PATENT DOCUMENTS

| DE | 20313417 | 11/2003 |
| EP | 0582226 B1 | 10/1997 |

(Continued)

OTHER PUBLICATIONS

Merriam-Webster definition of associated as accessed Jul. 22, 2015; http://www.merriam-webster.com/dictionary/associate.*

(Continued)

*Primary Examiner* — Jonathan Miles
(74) *Attorney, Agent, or Firm* — The Webb Law Firm

(57) ABSTRACT

The lancet device includes a housing and a lancet having a puncturing element. The lancet is disposed within the housing and is adapted for axial movement between an initial or pre-actuated position wherein the puncturing element is retained within the housing, and a puncturing position wherein the puncturing element extends through a forward opening in the housing. The lancet device includes a drive spring disposed within the housing for biasing the lancet toward the puncturing position, and a retraction or return spring for returning the lancet to a position within the housing where the puncturing element is disposed within the housing. The retraction spring thereafter maintains engagement with the lancet to assist in preventing the puncturing element from again projecting outward from the forward opening in the housing.

13 Claims, 51 Drawing Sheets

Related U.S. Application Data division of application No. 11/910,629, filed as application No. PCT/US2006/013470 on Apr. 7, 2006, now Pat. No. 8,333,781.

(51) Int. Cl.
*A61B 5/15* (2006.01)
*A61B 5/151* (2006.01)

(52) U.S. Cl.
CPC ....... *A61B 5/15111* (2013.01); *A61B 5/15113* (2013.01); *A61B 5/15117* (2013.01); *A61B 5/15142* (2013.01); *A61B 5/15144* (2013.01); *A61B 5/150259* (2013.01); *A61B 5/150412* (2013.01); *A61B 5/150503* (2013.01); *A61B 5/150549* (2013.01); *A61B 5/150564* (2013.01); *A61B 5/150618* (2013.01); *A61B 5/150717* (2013.01); *A61B 5/150908* (2013.01)

(58) Field of Classification Search
CPC ............ A61B 5/15117; A61B 5/15113; A61B 5/2033; A61B 2005/2013
See application file for complete search history.

(56) References Cited

U.S. PATENT DOCUMENTS

| | | |
|---|---|---|
| 4,388,925 A | 6/1983 | Burns |
| 4,442,836 A | 4/1984 | Meinecke et al. |
| 4,527,561 A | 7/1985 | Burns |
| 4,553,541 A | 11/1985 | Burns |
| 4,577,630 A | 3/1986 | Nitzsche et al. |
| 4,580,564 A | 4/1986 | Andersen |
| 4,653,513 A | 3/1987 | Dombrowski |
| 4,817,603 A | 4/1989 | Turner et al. |
| 4,869,249 A | 9/1989 | Crossman et al. |
| 4,924,879 A | 5/1990 | O'Brien |
| 4,994,068 A | 2/1991 | Hufnagle |
| 5,314,441 A | 5/1994 | Cusack et al. |
| 5,356,420 A | 10/1994 | Czernecki et al. |
| 5,540,709 A | 7/1996 | Ramel |
| 5,554,166 A | 9/1996 | Lange et al. |
| 5,611,809 A | 3/1997 | Marshall et al. |
| 5,628,764 A | 5/1997 | Schraga |
| 5,662,127 A | 9/1997 | De Vaughn |
| 5,755,733 A | 5/1998 | Morita |
| 5,984,940 A | 11/1999 | Davis et al. |
| 6,248,120 B1 | 6/2001 | Wyszogrodzki |
| 6,432,120 B1 | 8/2002 | Teo |
| 6,558,402 B1 | 5/2003 | Chelak et al. |
| 6,719,771 B1 | 4/2004 | Crossman |
| 6,852,119 B1 | 2/2005 | Abulhaj et al. |
| 7,175,643 B2 | 2/2007 | Shi |
| 7,282,058 B2 | 10/2007 | Levin et al. |
| 2002/0128608 A1 | 9/2002 | Teo et al. |
| 2004/0092997 A1 | 5/2004 | Levin et al. |
| 2004/0133172 A1 | 7/2004 | Wilkinson |
| 2004/0236362 A1 | 11/2004 | Shraga |
| 2006/0058828 A1 | 3/2006 | Shi |

FOREIGN PATENT DOCUMENTS

| | | |
|---|---|---|
| EP | 1219242 A1 | 7/2002 |
| EP | 1247489 A1 | 10/2002 |
| JP | 57168644 A | 10/1982 |
| JP | 61286738 A | 12/1986 |
| JP | 6238140 A | 2/1987 |
| JP | 04176444 A | 6/1992 |
| JP | 67329 A | 1/1994 |
| JP | 07500995 A | 2/1995 |
| JP | 2001-078991 | 3/2001 |
| JP | 2001078991 A | 3/2001 |
| JP | 2001353138 A | 12/2001 |
| JP | 2003325484 A | 11/2003 |
| JP | 2003339679 A | 12/2003 |
| JP | 2004-344292 | 12/2004 |
| JP | 2005518858 A | 6/2005 |
| JP | 2006504502 A | 2/2006 |
| WO | 03049613 A1 | 6/2003 |
| WO | 03073936 A2 | 9/2003 |
| WO | 2004039429 A2 | 5/2004 |
| WO | 2005009238 A1 | 2/2005 |

OTHER PUBLICATIONS

TheFreeDictionary.com definition for "contact" as accessed Jul. 20, 2017; http://www.thefreedictionary.com/contact.*

* cited by examiner

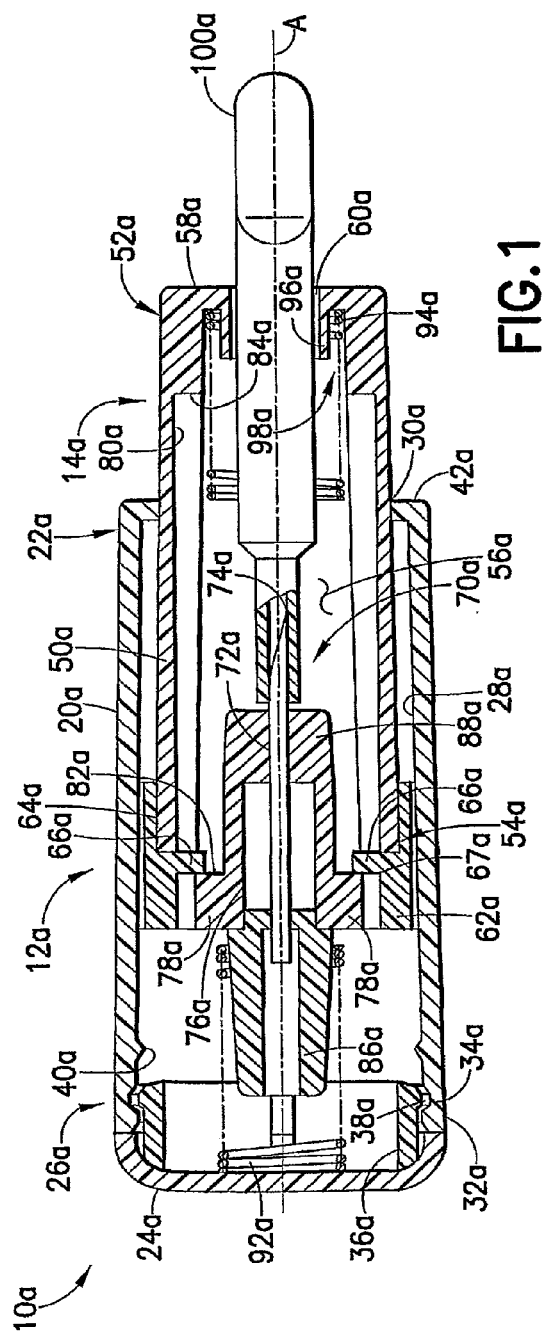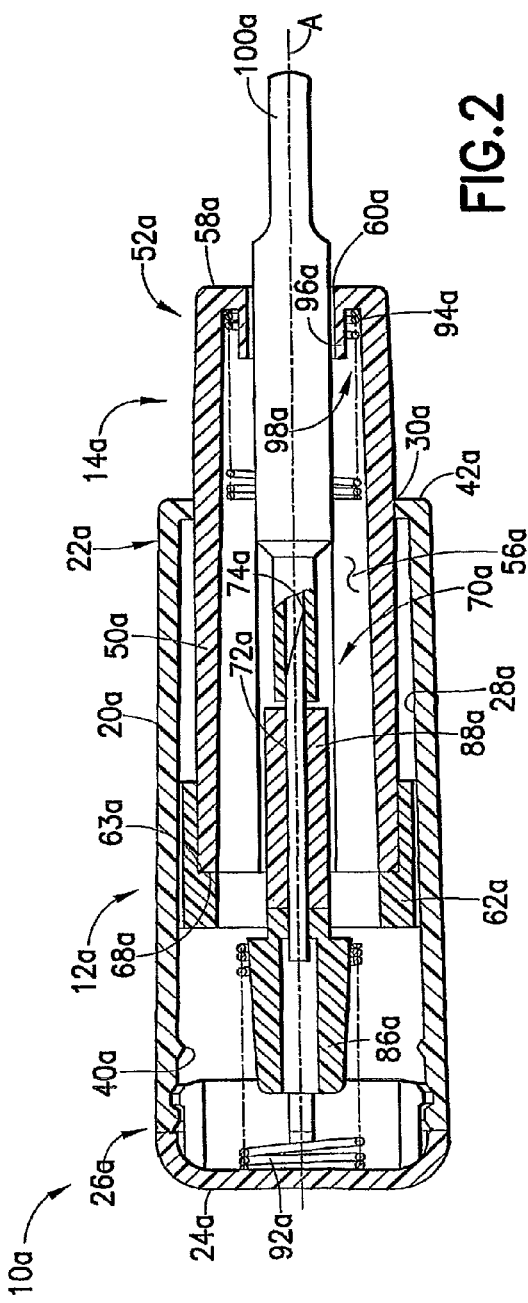

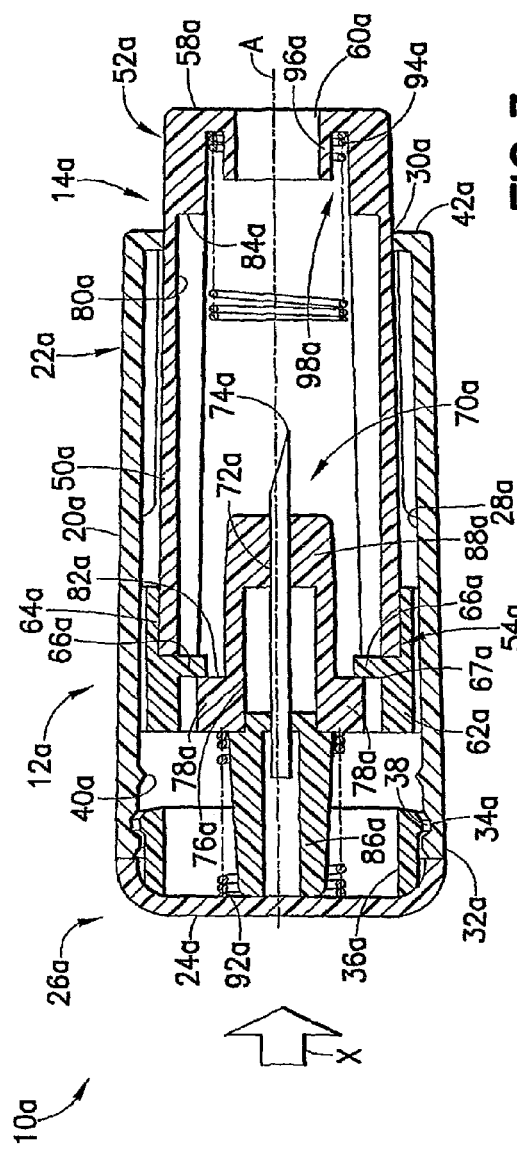

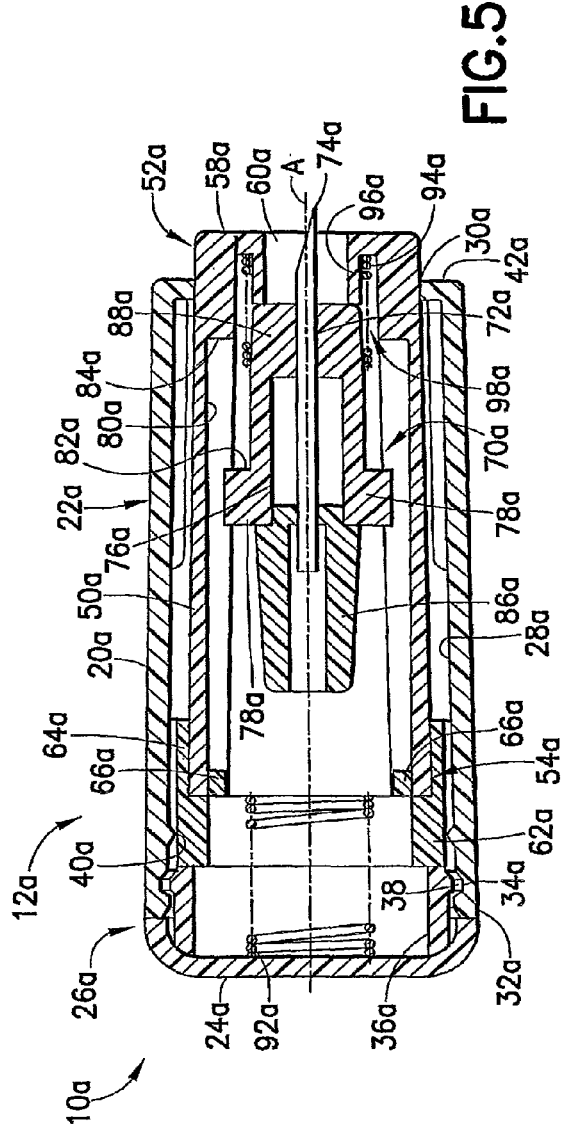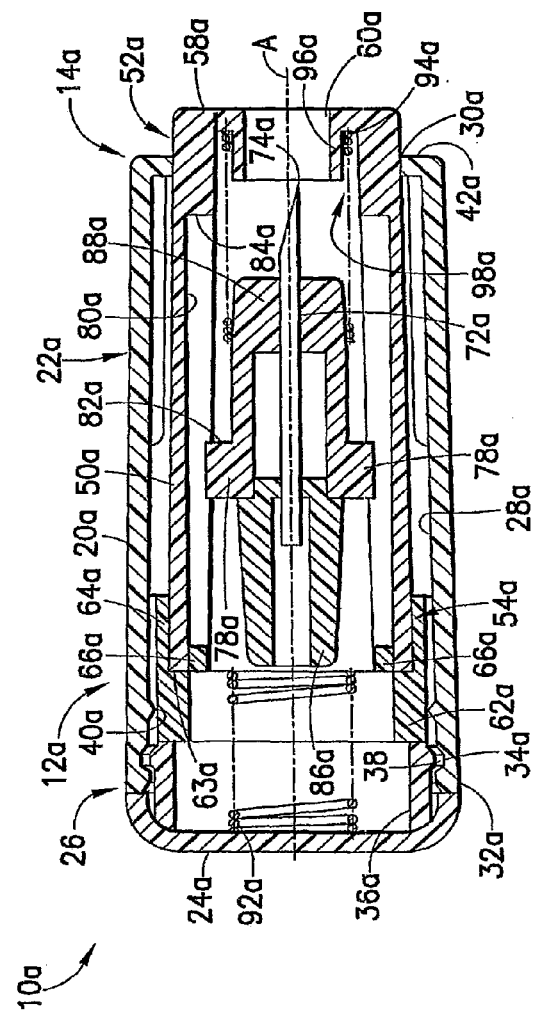

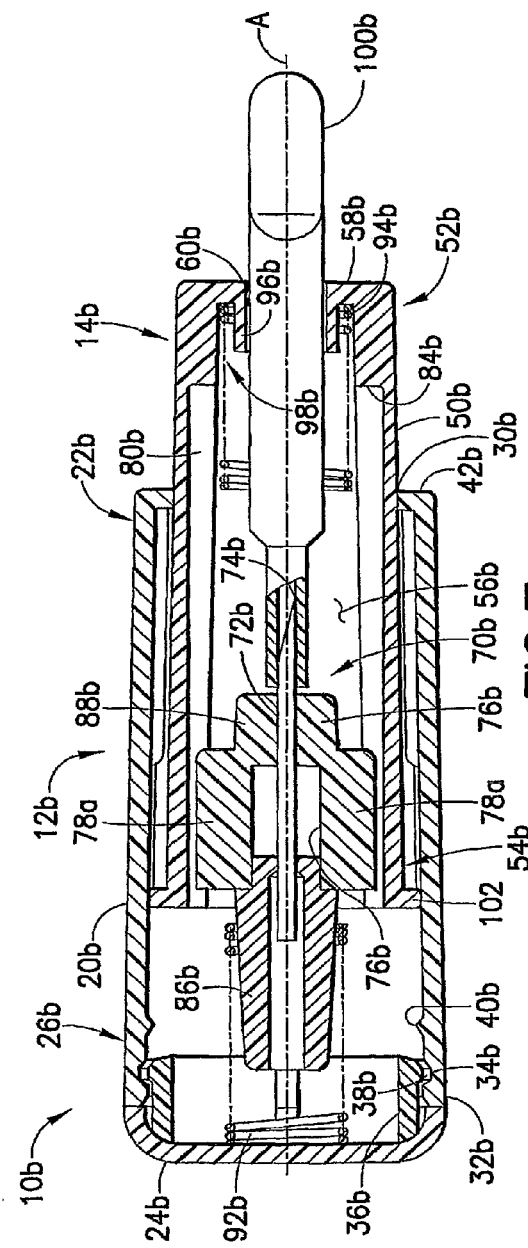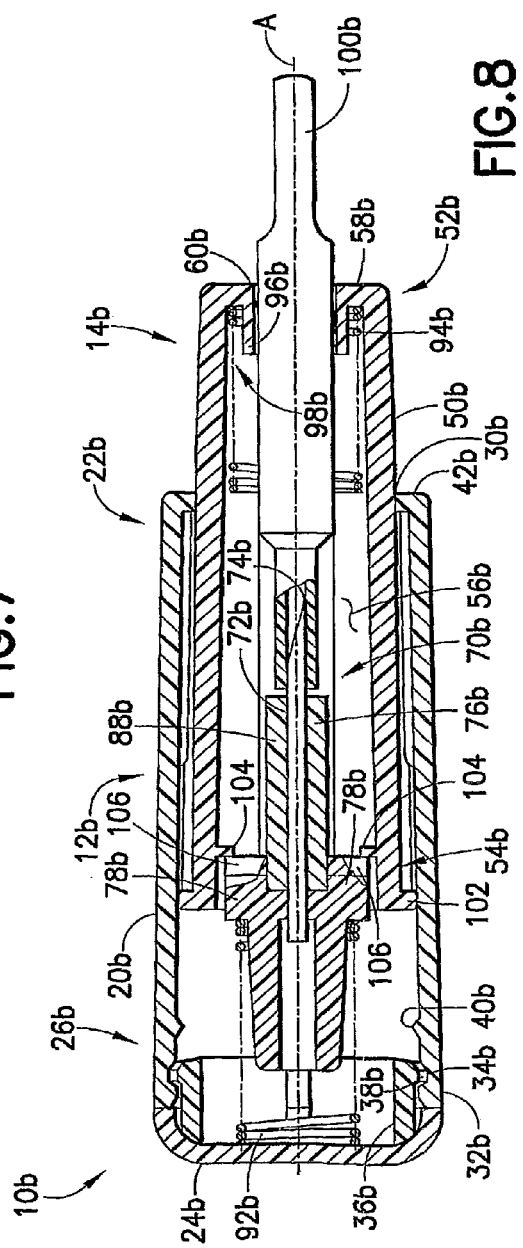

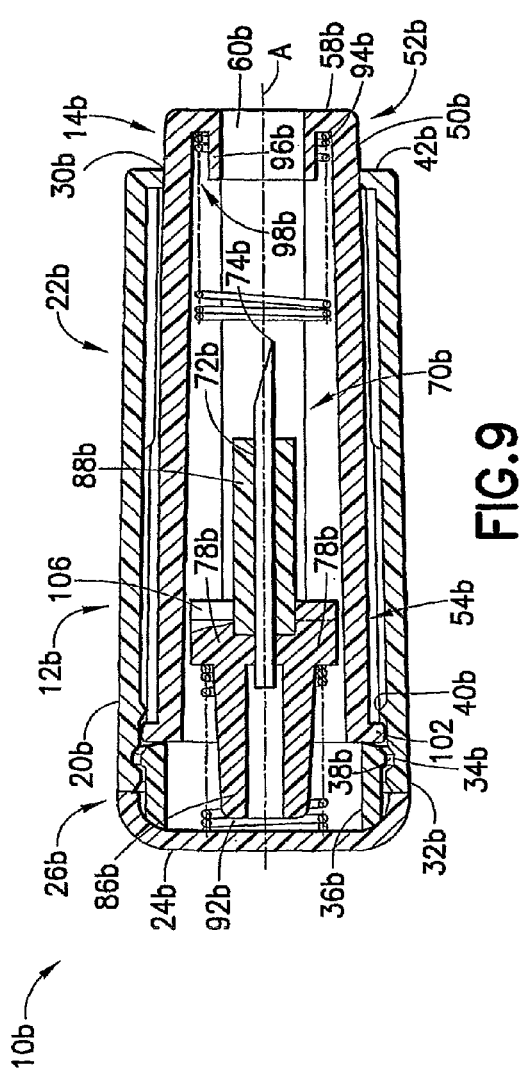
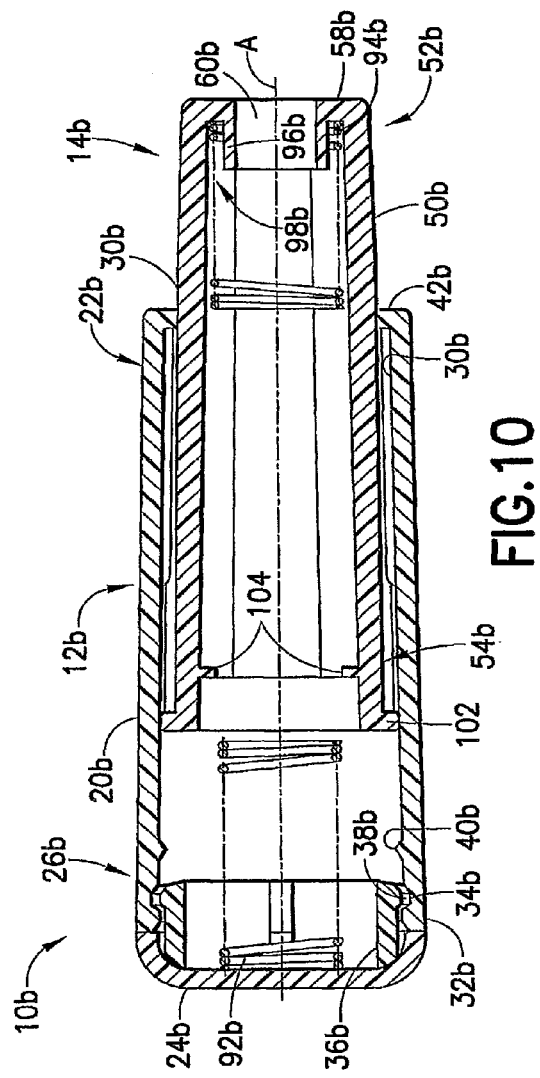

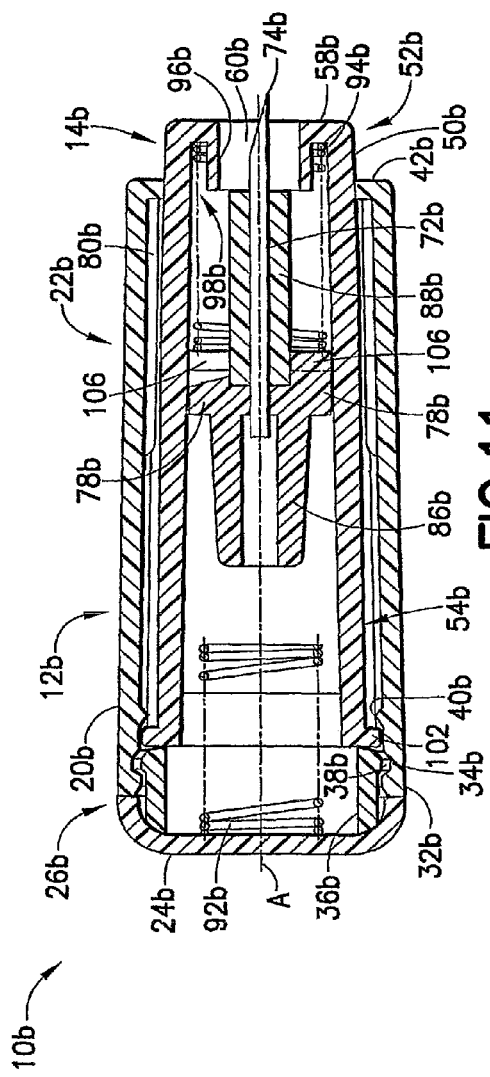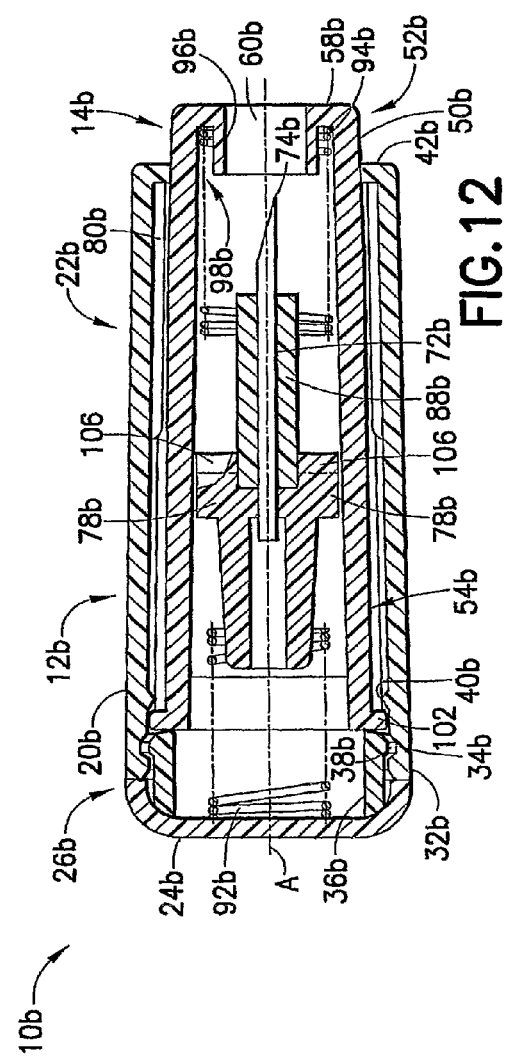

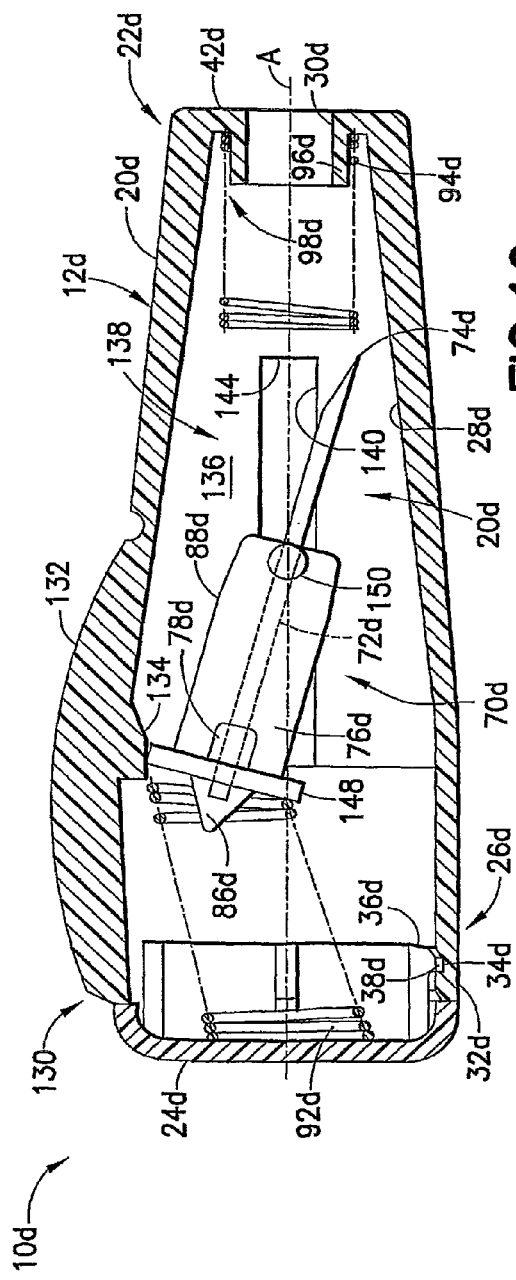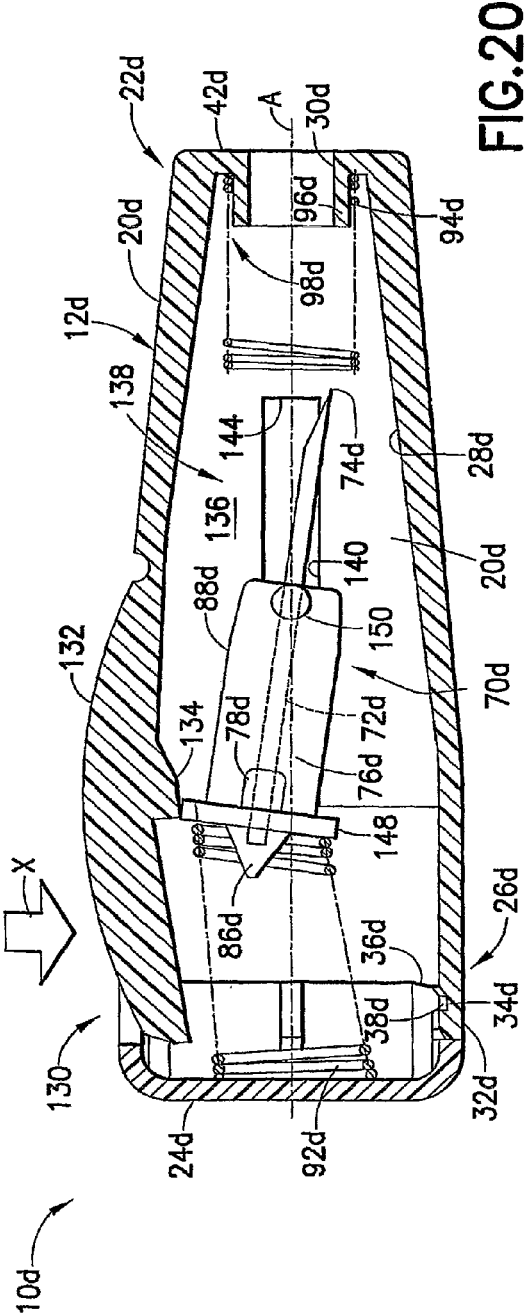

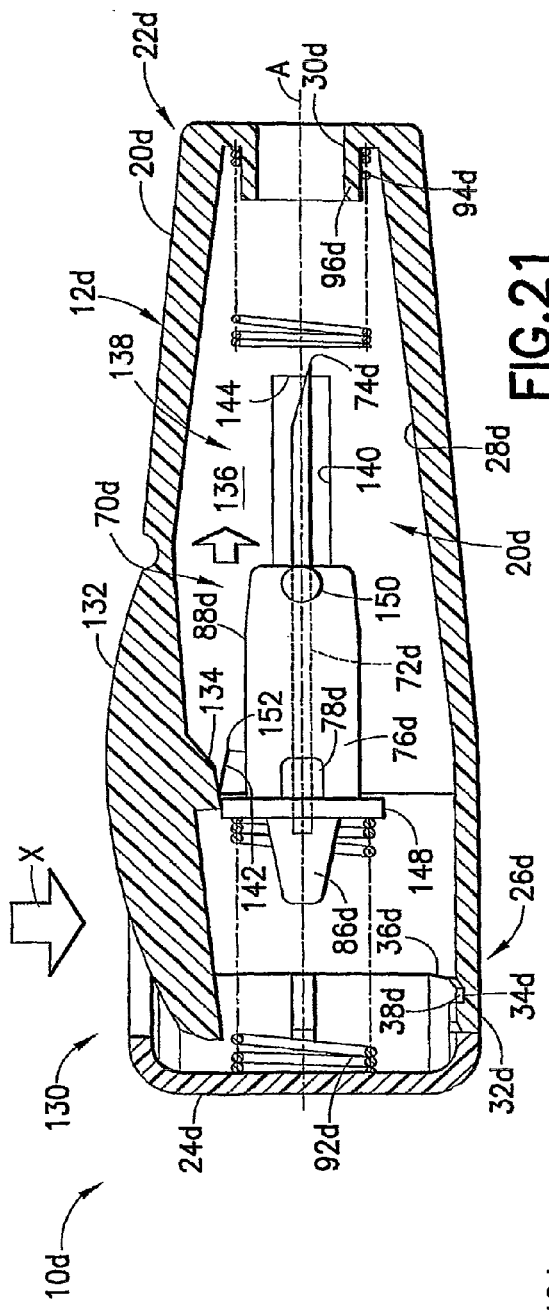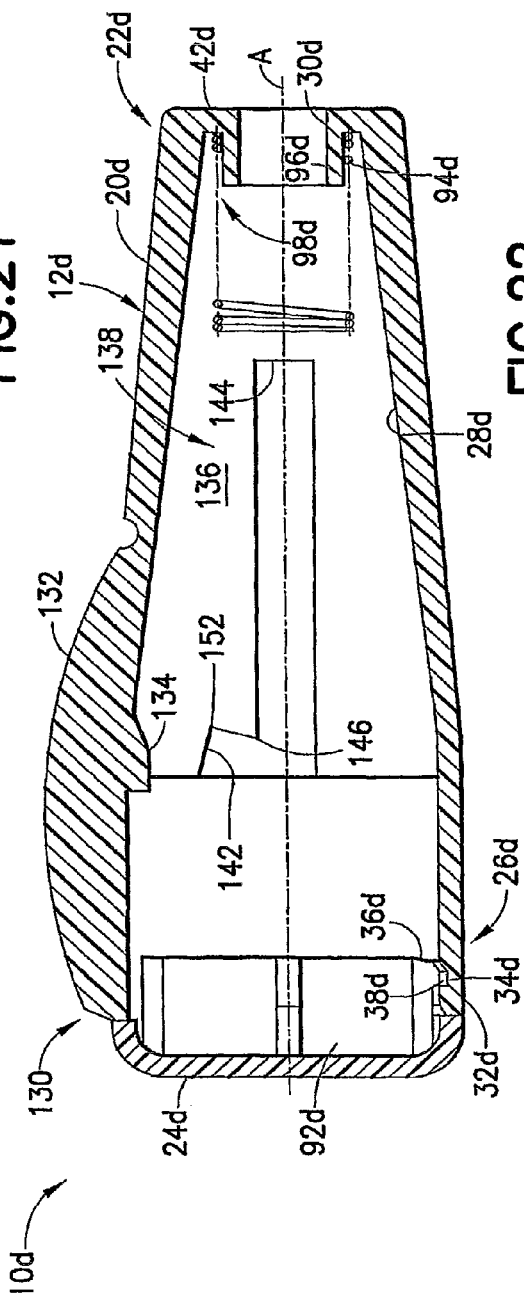

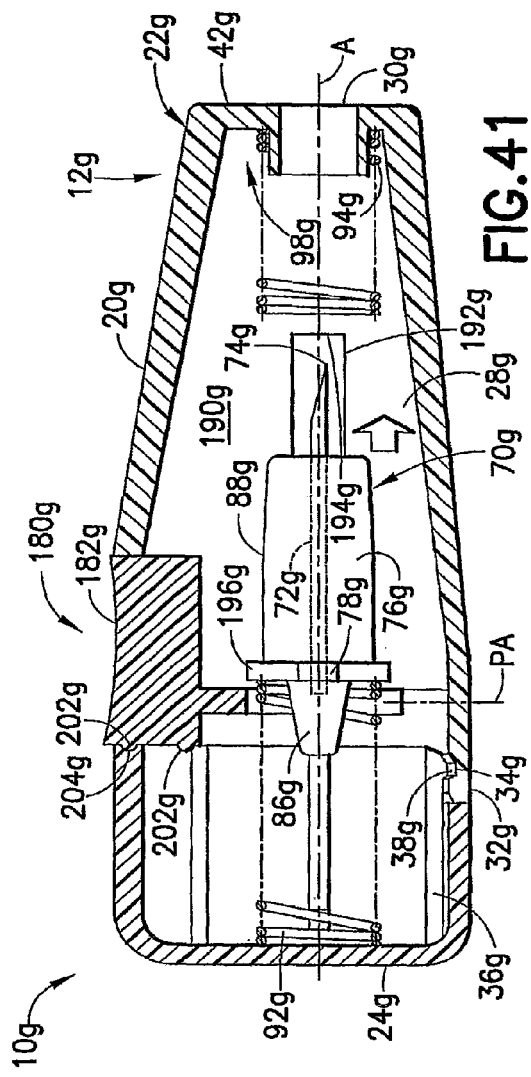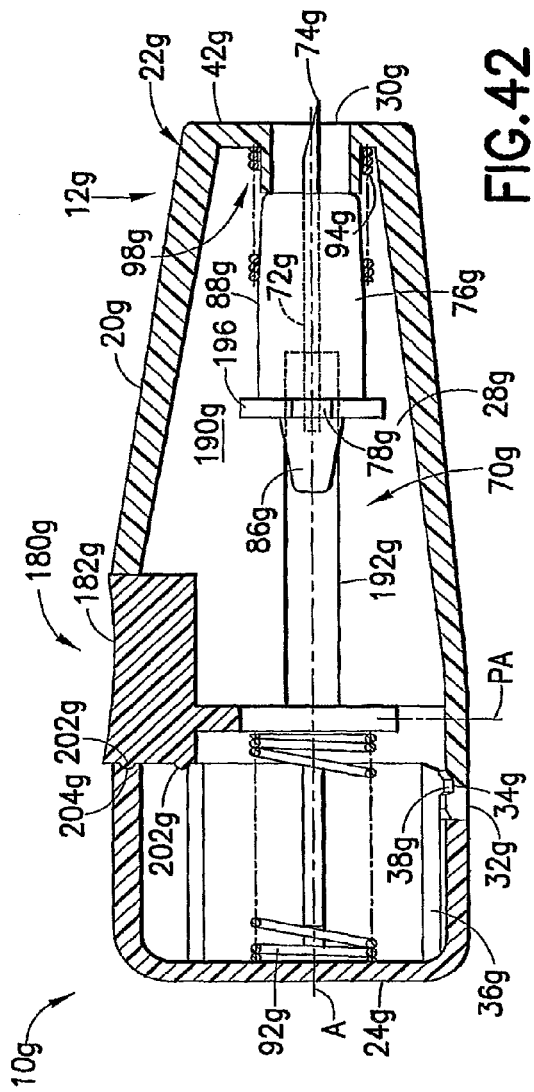

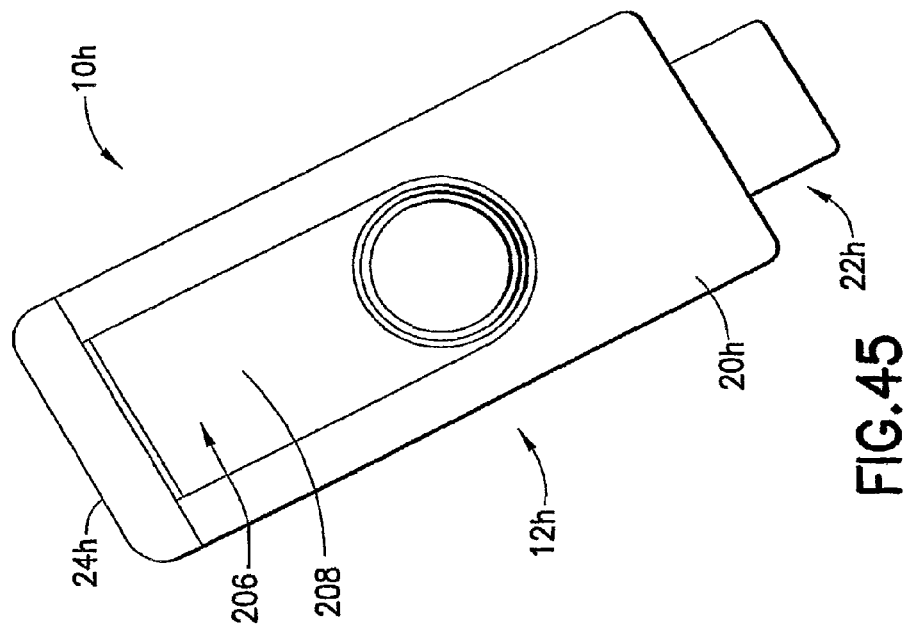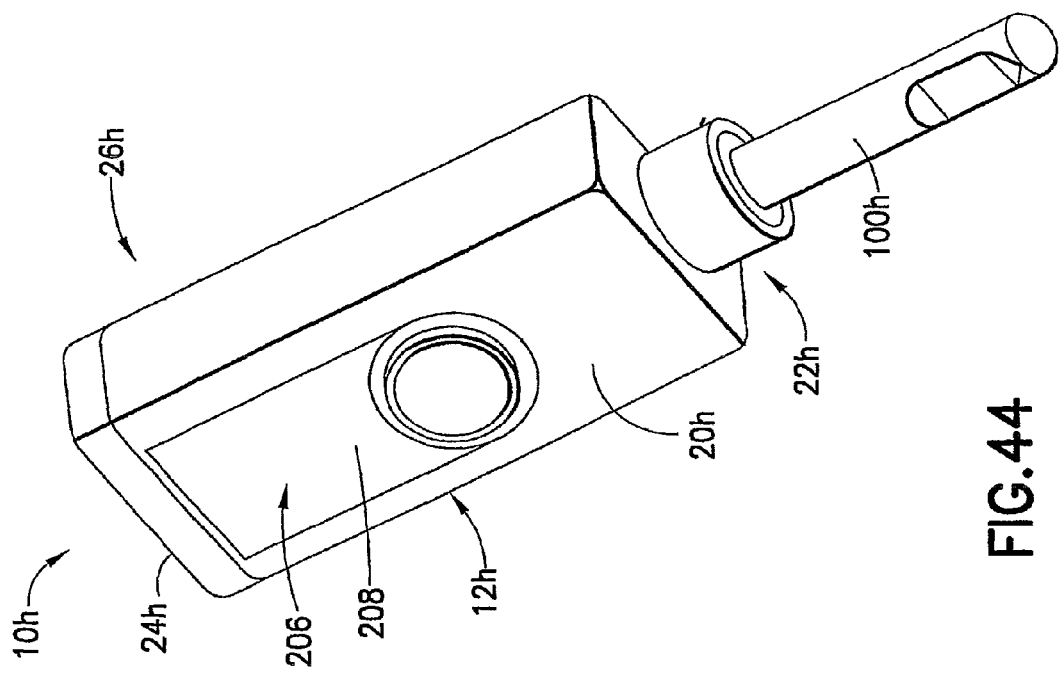

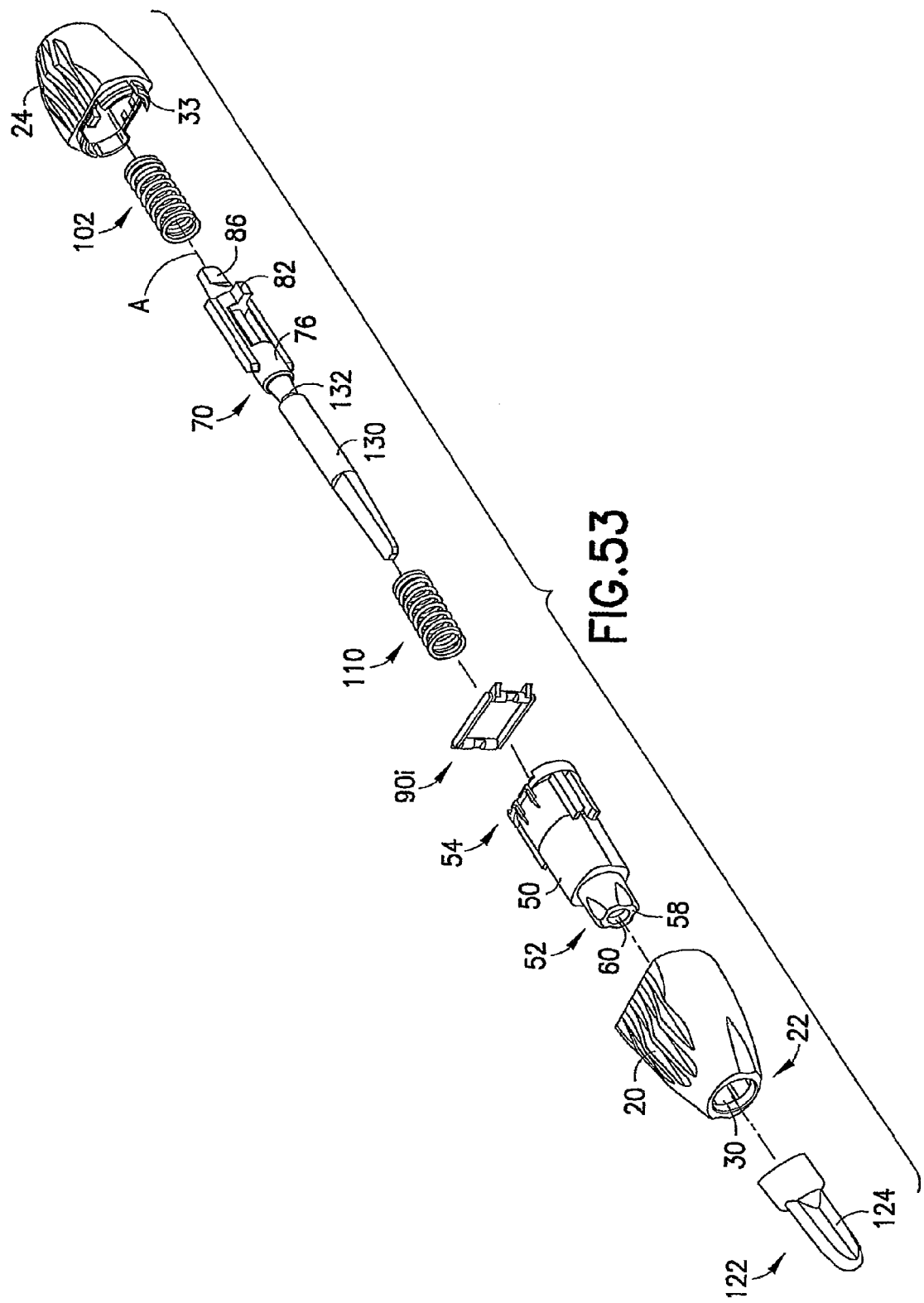

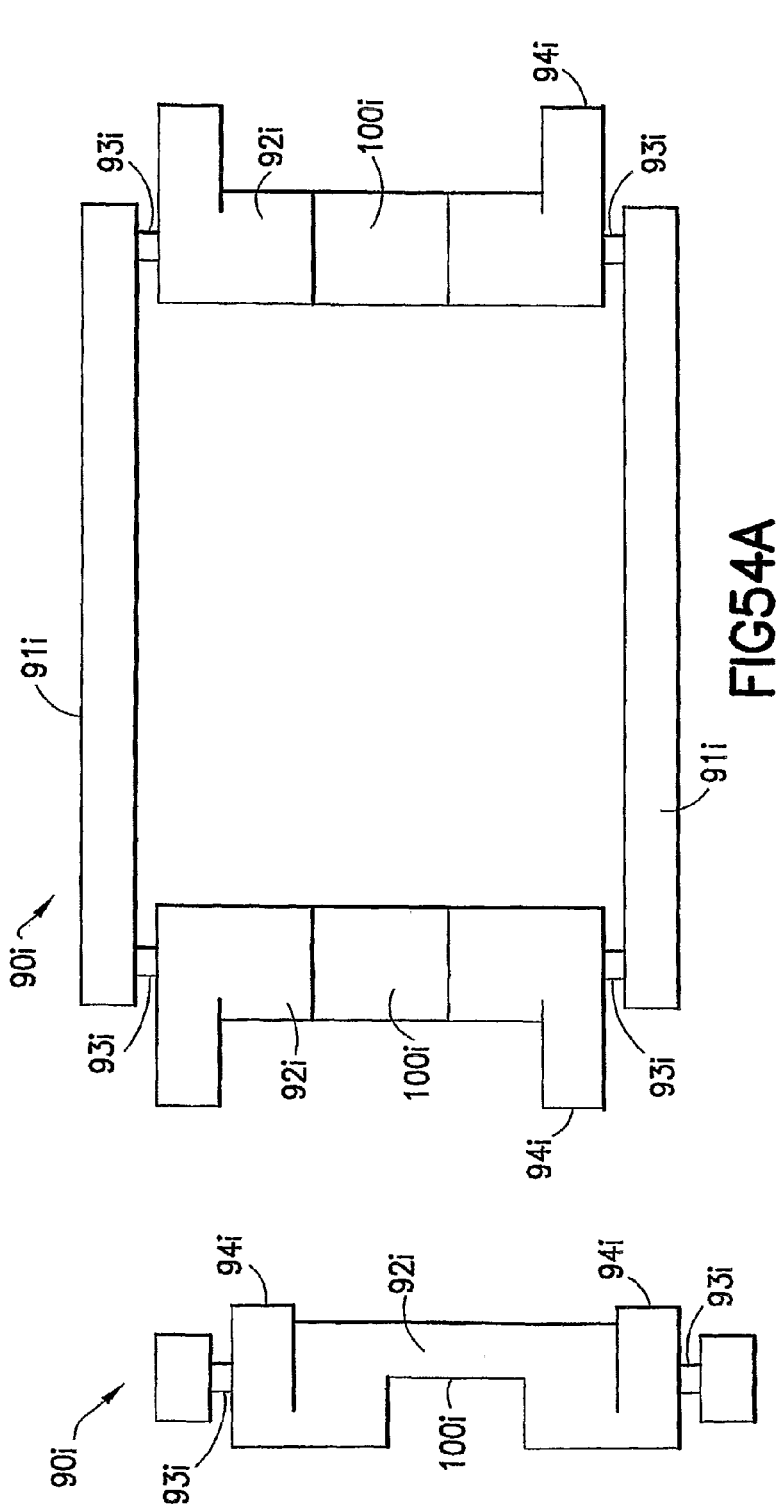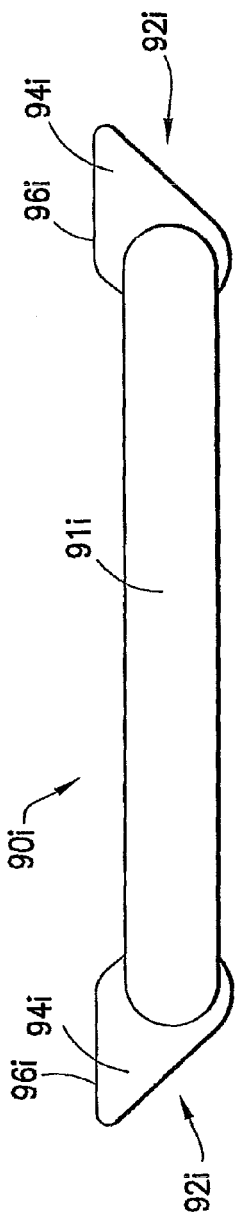

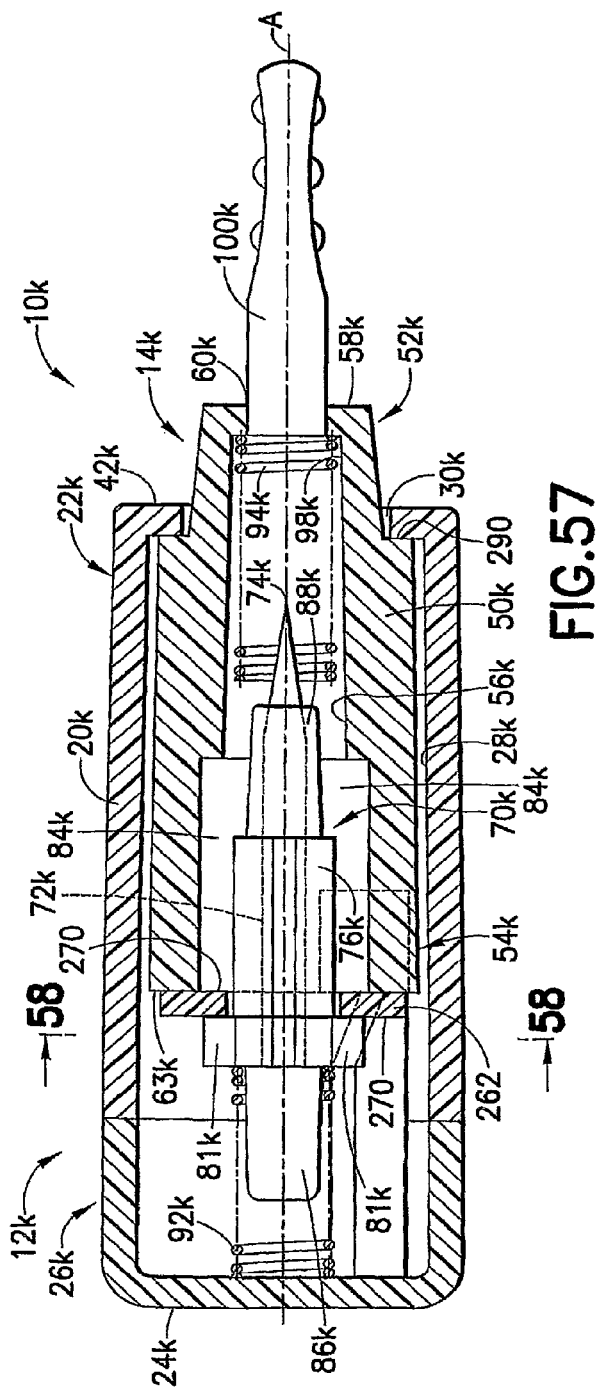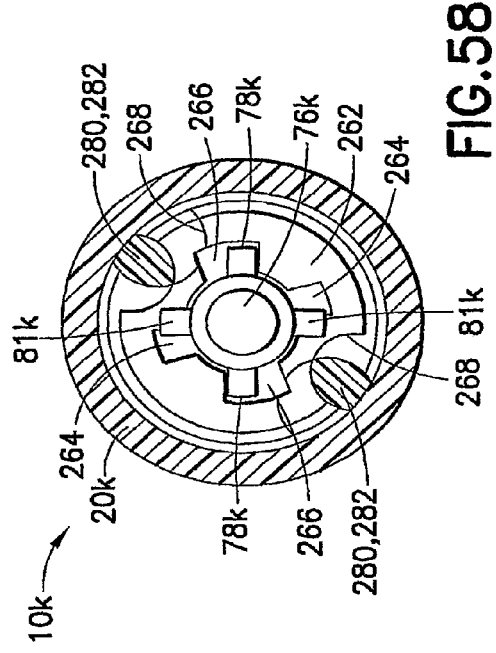

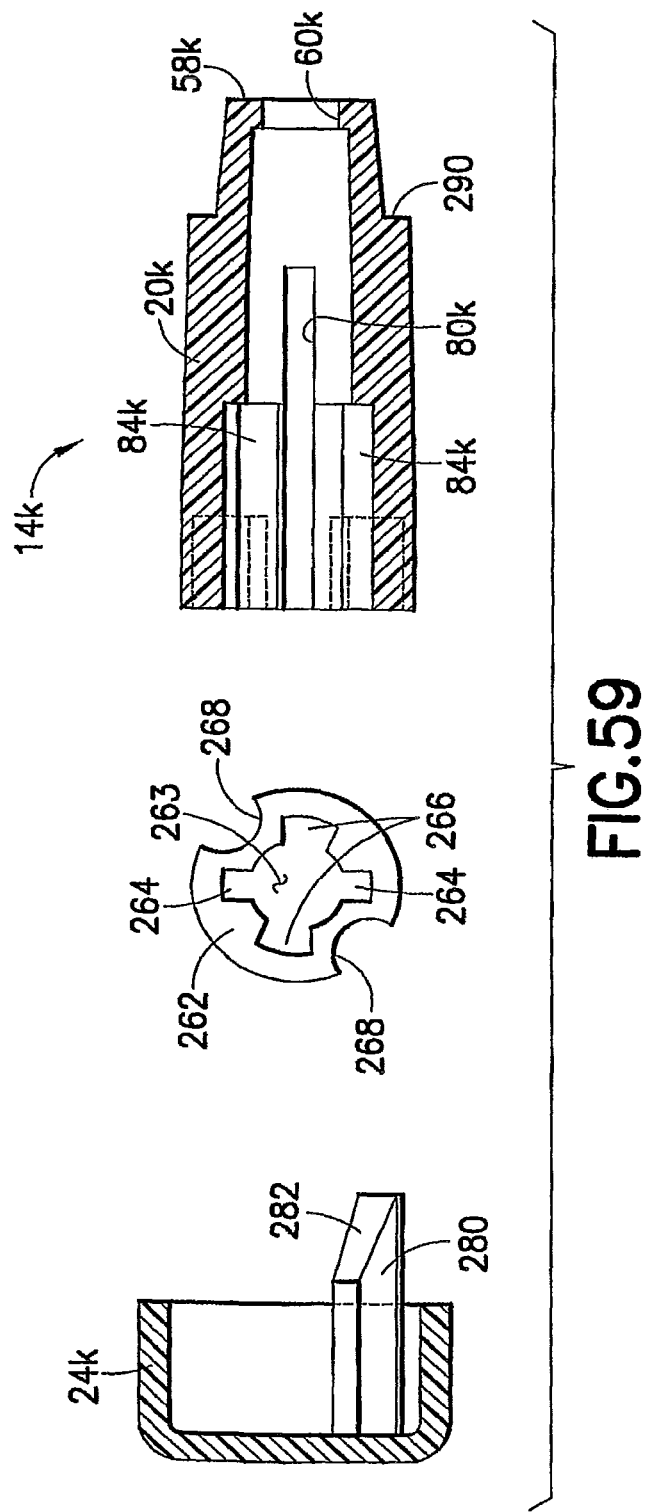

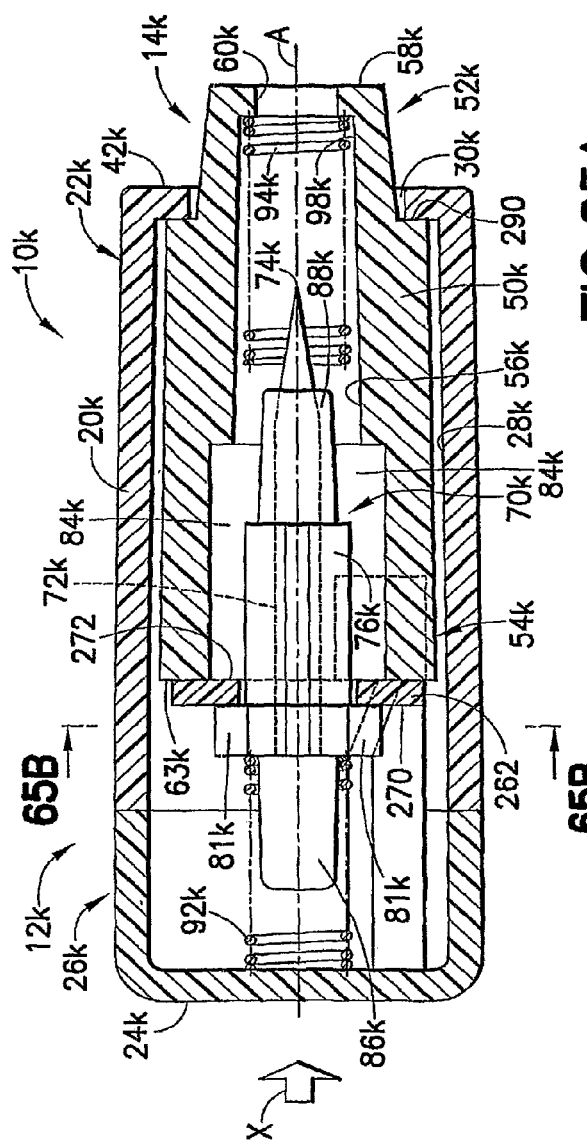
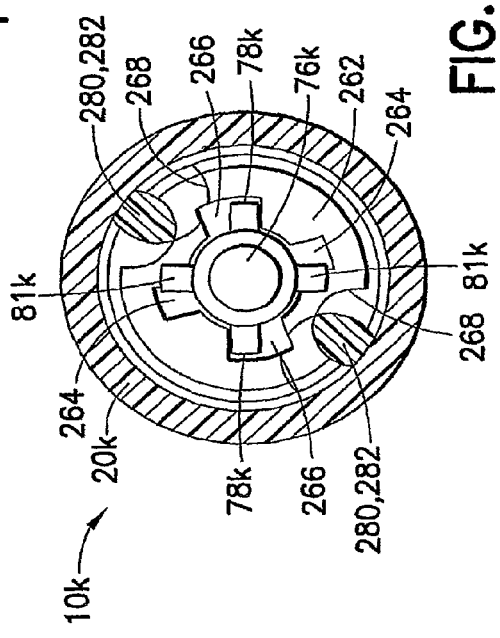
FIG.65A
FIG.65B

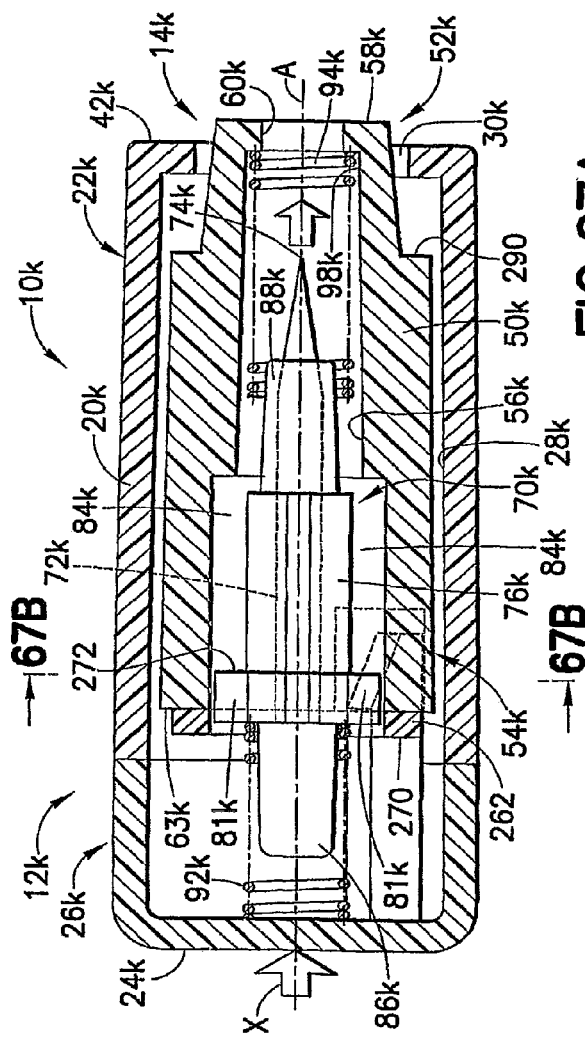
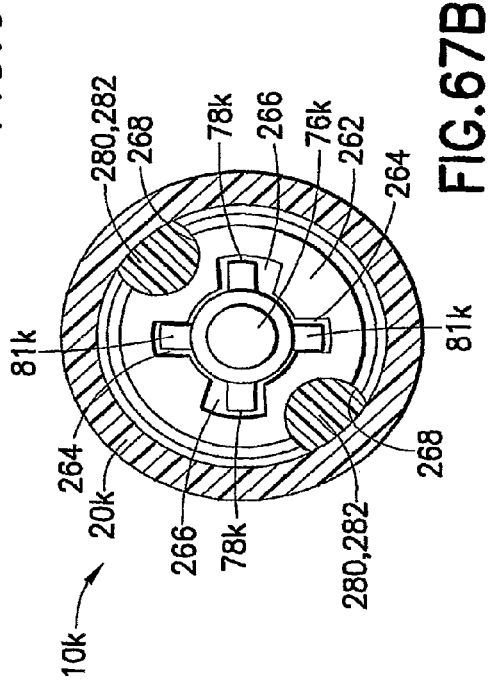
FIG.67A
FIG.67B

LANCET DEVICE

CROSS-REFERENCE TO RELATED APPLICATION

The present application is a continuation of U.S. patent application Ser. No. 13/669,792, published as United States Patent Publication No. 2013/0066354, filed Nov. 6, 2012 entitled "Lancet Device" which is a divisional application of U.S. patent application Ser. No. 11/910,629 filed Oct. 6, 2008, now U.S. Pat. No. 8,333,781, which is a national stage application under 35 U.S.C. § 371 of International Application PCT/US06/13470 filed Apr. 7, 2006, the entire disclosures of each of which are hereby incorporated by reference.

BACKGROUND OF THE INVENTION

Field of the Invention

The invention relates generally to medical puncturing devices, commonly referred to as lancets, which are used to take blood samples from patients and, more specifically, to a lancet device that is designed for ease of use with activation achieved during contact of the device in normal use.

Description of Related Art

Lancet devices are used in the medical field for puncturing the skin of a patient to obtain a capillary blood sample from the patient. Certain diseases, such as diabetes, require that the patient's blood be tested on a regular basis to monitor, for example, the patient's blood sugar levels. Additionally, test kits, such as cholesterol test kits, often require a blood sample for analysis. The blood collection procedure usually involves pricking a finger or other suitable body part in order to obtain the blood sample. Typically, the amount of blood needed for such tests is relatively small and a small puncture wound or incision normally provides a sufficient amount of blood for these tests.

Various lancet devices are commercially available to hospitals, clinics, doctors' offices, and the like, as well as to individual consumers. Such devices typically include a sharp-pointed member such as a needle, or a sharp-edged member such as a blade, that is used to make a quick puncture wound or incision in the patient's skin in order to provide a small outflow of blood. It is often physiologically and psychologically difficult for many people to prick their own finger with a hand-held needle or blade. As a result, lancet devices have evolved into devices that facilitate puncturing or cutting the skin of the patient upon the actuation of a triggering mechanism. In some devices, the needle or blade is kept in a standby position until it is triggered by the user, who may be a medical professional in charge of drawing blood from the patient, or the patient himself or herself. Upon triggering, the needle or blade punctures or cuts the skin of the patient, for example on the finger. Often, a spring is incorporated into the device to provide the "automatic" force necessary to puncture or cut the skin of the patient.

It is of the utmost importance in the medical field that such medical puncturing devices or lancets are in a sterile condition before use. Today, generally without exception, medical puncturing devices or lancets are manufactured and packaged in a sterilized condition before they are distributed to medical professionals and members of the public who have a need for such devices. The sterile packaging maintains the sterility of the device, ensuring that the surrounding environment does not contaminate it until use. In addition, it is also of increasing importance that the user or another person does not come into contact with the needle or blade after use of the device. With the concern over blood-borne diseases, medical professionals are required to take great care with medical devices that come into contact with the blood of patients. Thus, an important aspect of lancet design involves preventing the needle or blade of the device from wounding the user or another person after the blood sample is drawn from the patient. Once used, the needle or blade should be shielded to prevent the needle or blade from wounding the user or another person handling the device. Moreover, the lancet device should be disposable to eliminate the chances of disease transmission due to the needle or blade being used on more than one person. In this regard, the lancet device should ideally be designed for one firing, and have safety features to prevent reuse.

Advances have been made in recent years to increase safety in operating and handling used lancet devices. For example, lancet devices are currently available which are single shot devices that feature automatic ejection and retraction of the puncturing or cutting element from and into the device. Examples of such medical puncturing devices are disclosed in U.S. Pat. Nos. 6,432,120; 6,248,120; 5,755,733; and 5,540,709.

U.S. Pat. No. 6,432,120 to Teo discloses a lancet device that includes a lancet holder which contains a spring-loaded lancet structure. The spring-loaded lancet structure includes a single spring that effects the ejection and retraction of a lancet needle upon the triggering of the structure. U.S. Pat. No. 6,248,120 to Wyszogrodzki discloses a lancet device comprised of a housing, a shielding portion, a piston with a puncturing tip, and drive and return springs that eject and retract the piston, respectively, upon the breakage of internal wing elements in the housing. U.S. Pat. No. 5,755,733 to Morita discloses a lancet device that includes a combined holder and lancet structure. The lancet structure includes a lancet member with a puncturing tip and a compressible spring member that causes the lancet member to puncture the skin of a patient upon actuation of a pair of actuating arms.

U.S. Pat. No. 5,540,709 to Ramel discloses a lancet device that includes a housing enclosing a slidable trigger, which is used to trigger a compressed spring that powers a piercing lancet member to pierce the skin of a patient. The housing includes a pair of internal fingers that engage the body of the lancet member, which are then released of engagement with the lancet member body by axial force applied by the user to the slidable trigger. Other medical puncturing devices or lancets known in the art are disclosed, in U.S. Pat. Nos. 4,869,249 and 4,817,603. The devices disclosed in these references include a cap that is used to protect a needle or to keep the needle sterile.

In view of the foregoing, a need generally exists in the medical field for a medical puncturing device that is easy for a user to manipulate and use while ensuring sterility before use and safe and secure disposal after use. Additionally, a need exists in the medical field for a simple, inexpensive, reliable, and disposable medical puncturing device for use in collecting blood samples.

SUMMARY OF THE INVENTION

The present invention is generally directed to a lancet device. The lancet device according to a first embodiment comprises a housing, a shield at least partially disposed within the housing and movably associated therewith, and a lancet disposed in the housing and axially movable through the shield. The lancet comprises a puncturing element, and is adapted for axial movement between an initial position wherein the puncturing element is disposed within the housing and a puncturing position wherein the puncturing element extends through a forward opening in the shield for a puncturing procedure. A drive spring is disposed between a rearward end of the housing and the lancet for biasing the lancet to the puncturing position. The lancet device further comprises an actuator associated with the shield and in interference engagement with the lancet in the initial position. In operation, axial movement of the shield into the housing causes the actuator to move the lancet toward and contact the rearward end of the housing to at least partially compress the drive spring. Upon contact with the rearward end of the housing, further force applied to retract the shield into the housing causes failure of the interference engagement between the actuator and the lancet thereby releasing the at least partially compressed drive spring and permitting the drive spring to bias the lancet through the shield to the puncturing position. The actuator comprises a shearable element associated with a proximal end of the shield, and the shearable element may comprise at least one breakable shelf or tab providing the interference engagement with the lancet.

The lancet device according to a second embodiment comprises a housing, a shield at least partially disposed within the housing and movably associated therewith, with the shield comprising at least one internal tab, and a lancet disposed in the housing and axially movable through the shield. The lancet comprises a puncturing element, and is adapted for axial movement between an initial position wherein the puncturing element is disposed within the housing and a puncturing position wherein the puncturing element extends through a forward opening in the shield for a puncturing procedure. The lancet is in interference engagement with the internal tab in the shield in the initial position. A drive spring is disposed between a rearward end of the housing and the lancet for biasing the lancet to the puncturing position. In operation, axial movement of the shield into the housing causes the lancet to move toward and contact the rearward end of the housing due to the interference engagement with the shield internal tab to at least partially compress the drive spring. Upon contact with the rearward end of the housing, further force or movement applied to retract the shield into the housing causes failure of the internal tab removing the interference engagement and releasing the at least partially compressed drive spring to bias the lancet through the shield to the puncturing position. The lancet may comprise a cutting element providing the interference engagement with the internal tab in the initial position of the lancet, and failure of the internal tab may be caused by the cutting element cutting through the internal tab.

The lancet device according to a third embodiment comprises a housing, a shield at least partially disposed within the housing and movably associated therewith, and a lancet disposed in the housing and axially movable through the shield and comprising a puncturing element. The lancet is generally adapted for axial movement between an initial position wherein the puncturing element is disposed within the housing and a puncturing position wherein the puncturing element extends through a forward opening in the shield for a puncturing procedure. A drive spring is disposed between a rearward end of the housing and the lancet for biasing the lancet to the puncturing position. The lancet device further comprises an actuator in interference engagement with the lancet in the initial position and maintains the drive spring in an at least partially compressed state in the initial position of the lancet. The actuator comprises a sleeve portion associated with the housing and at least one elastic element in interference engagement with the lancet. In operation, axial movement of the shield into the housing causes the shield to move the elastic element radially outward from the lancet releasing the interference engagement therewith, and thereby releasing the at least partially compressed drive spring to bias the lancet through the shield to the puncturing position. The sleeve portion and elastic element may be formed integrally and connected, for example, by a living hinge.

The lancet device according to fourth embodiment comprises a housing and a lancet disposed in the housing and axially movable through the housing and comprising a puncturing element. The lancet is adapted for axial movement between an initial position wherein the puncturing element is disposed within the housing and a puncturing position wherein the puncturing element extends through a front opening in the housing for a puncturing procedure. A drive spring is disposed between a rearward end of the housing and the lancet for biasing the lancet to the puncturing position. The drive spring is held in at least partially compressed state between the rearward end of the housing and the lancet by an interference engagement between the lancet and housing. The lancet device further comprises an actuator pivotally connected to the housing and in contact engagement with the lancet in the initial position for causing release of the drive spring. In operation, movement, typically depression, of the actuator causes pivotal movement thereof into the housing causing at least a portion of the lancet to move downward in the housing until the lancet is released of interference engagement with the housing, thereby releasing the at least partially compressed drive spring to bias the lancet through the housing to the puncturing position. The lancet may comprises at least one outward-extending guide tab and the housing may define an internal guide channel comprising a longitudinal main channel and a generally transverse side channel, such that the interference engagement comprises the guide tab engaging a corner or vertex defined generally at the intersection of the main channel and side channel.

The lancet device according to a fifth embodiment comprises a housing having an internal cam surface at a rearward end thereof, a shield at least partially disposed within the housing and movably associated therewith, and a lancet disposed in the housing and axially movable through the shield and comprising a puncturing element. The lancet is adapted for axial movement between an initial position wherein the puncturing element is disposed within the housing and a puncturing position wherein the puncturing element extends through a forward opening in the shield for a puncturing procedure. A drive spring is disposed between the rearward end of the housing and the lancet for biasing the lancet to the puncturing position. The lancet device further comprises an actuator associated with a proximal end of the shield disposed in the housing and in interference engagement with the lancet in the initial position thereof. In operation, axial movement of the shield into the housing causes the actuator to move the lancet toward the rearward end of the housing to at least partially compress the drive spring while simultaneously interacting with the internal cam surface. Continued interaction with the internal cam surface during the shield axial movement further moves the actuator to a position within the housing where the interference engagement between the actuator and the lancet is released, thereby releasing the at least partially compressed drive spring and permitting the drive spring to bias the lancet through the shield to the puncturing position. The actuator may comprise a plate member slidably associated with the shield proximal end and defining a keyhole for permitting passage of the lancet therethrough to release the interference engagement.

The lancet device according to a sixth embodiment comprises a housing and a lancet disposed in the housing and axially movable through the housing. The lancet device comprises a puncturing element, and is adapted for axial movement between an initial position wherein the puncturing element is disposed within the housing and a puncturing position wherein the puncturing element extends through a front opening in the housing for a puncturing procedure. A drive spring is disposed between a rearward end of the housing and the lancet for biasing the lancet to the puncturing position. The lancet device further comprises an actuator associated with the housing and in interference engagement with the lancet in the initial position. The interference engagement between actuator and lancet maintains the drive spring in at least a partially compressed state between the rearward end of the housing and the lancet in the initial position. In operation, movement, typically depression, of the actuator into the housing moves the actuator to a position within the housing where the interference engagement between the actuator and the lancet is released, thereby releasing the at least partially compressed drive spring and permitting the drive spring to bias the lancet through the shield to the puncturing position. The actuator may comprise a lever member pivotally connected to the housing and a plate member depending into the housing. The plate member defines a keyhole for permitting passage of the lancet therethrough to release the interference engagement. The lancet device, according to a seventh embodiment, may include the actuator comprising a depressible button associated with the housing and a plate member depending into the housing, with the plate member defining a keyhole for permitting passage of the lancet therethrough to release the interference engagement.

The lancet device according to an eighth embodiment comprises a housing, a lancet disposed in the housing and axially movable through the housing and comprising a puncturing element. The lancet is adapted for axial movement between an initial position wherein the puncturing element is disposed within the housing and a puncturing position wherein the puncturing element extends through a front opening in the housing for a puncturing procedure. A drive spring is disposed between a rearward end of the housing and the lancet for biasing the lancet to the puncturing position. The drive spring is held in at least a partially compressed state between the rearward end of the housing and the lancet by an interference engagement between the lancet and housing. The lancet device further comprises an actuator connected or optionally integrated pivotally to the housing and adapted to sever the interference engagement between the lancet and housing for causing release of the drive spring. In operation, movement, typically depression, of the actuator causes pivotal movement thereof into the housing until the actuator severs the interference engagement between the lancet and housing thereby releasing the at least partially compressed drive spring to bias the lancet through the housing to the puncturing position. The actuator may comprise a lever member connected pivotally to the housing and comprising a depending cutting edge for severing the interference engagement between the lancet and housing.

The lancet device according to a further embodiment comprises a housing and a lancet disposed within the housing and comprising a puncturing element. The lancet is adapted for axial movement between an initial, pre-actuated position wherein the puncturing element is retained within the housing and a puncturing position wherein the puncturing element extends through a front opening the housing. A drive spring is disposed between a rearward end of the housing and the lancet for biasing the lancet toward the puncturing position. The lancet device further comprises a retaining hub retaining the lancet in the pre-actuated position. The retaining hub is adapted to retain the lancet against the bias of the drive spring, and comprises a pivotal cam element. The cam element is in interference engagement with the lancet in the pre-actuated position of the lancet. In operation, axial movement of the housing toward the retaining hub causes the cam element to pivot, thereby moving the lancet toward the rearward end of the housing to at least partially compress the drive spring and releasing the cam element from interference engagement with the lancet, permitting the drive spring to drive the lancet through the housing toward the puncturing position. The cam element may define a recess or notch which releases the cam element from the interference engagement with the lancet when the cam element is pivoted to align the recess with an interfering on the lancet.

The lancet device may further comprise an internal contact within the housing and axial movement of the housing toward the retaining hub causes the internal contact within the housing to pivot the cam element. The cam element may comprise a contact surface for engagement with the internal contact of the housing. The internal contact of the housing may comprise an integrally formed cam surface for cooperating engagement with the contact surface of the cam element. The retaining hub may comprise an annular rim, generally defined by a pair of opposed support members connected by a pair of pivotal cam elements. The cam elements may comprise pivotal shafts connecting the support members.

The lancet device according to a final embodiment generally comprises a housing including an internal actuation member, a shield at least partially disposed within the housing and movably associated therewith, a lancet disposed in the housing and axially movable through the shield, and a rotation element. The lancet includes a puncturing element and is adapted for axial movement between an initial position wherein the puncturing element is disposed within the housing, and a puncturing position wherein the puncturing element extends through a forward opening in the shield for a puncturing procedure. A drive spring is typically disposed between a rearward end of the housing and the lancet for biasing the lancet to the puncturing position. The lancet is typically in interference engagement with the rotation element in the initial position. In operation, axial movement of the shield into the housing causes the actuation member to rotate the rotation element relative to the lancet to a release position releasing the interference engagement between the lancet and rotation element, thereby permitting the drive spring to bias the lancet through the shield to the puncturing position.

The rotation element may be associated with the shield such that axial movement of the shield into the housing causes the drive spring to at least partially compress between the housing rearward end and lancet due to the interference engagement between the lancet and rotation element. The rotation element may be associated with a rearward end of the shield disposed in the housing.

The actuating member may comprise a cam element with a cam surface and the rotation element may comprise a guide plate defining a cam guide recess for receiving the cam element, such that axial movement of the shield into the housing causes the cam surface to engage the cam guide recess an impart rotational motion to the guide plate. The lancet may comprise an actuation tab in interference engagement with the guide plate, and the guide plate may define a clearance slot, such that the interference engagement may be released when the guide plate rotates to the release position where the actuation tab aligns with the clearance slot.

The actuating member may comprise a cam element with a cam surface and the rotation element may comprise a cam follower, such that axial movement of the shield into the housing causes the cam surface to engage the cam follower an impart rotational motion thereto at least until the cam follower reaches the release position.

Further details and advantages of the invention will become clear from the following detailed description when read in conjunction with the accompanying drawings.

BRIEF DESCRIPTION OF THE DRAWINGS

FIG. 1 is a longitudinal cross-sectional view of a first embodiment of a lancet device showing the lancet device in an initial, pre-actuated state;

FIG. 2 is a longitudinal cross-sectional view of the lancet device of FIG. 1 taken along a perpendicular longitudinal axis to the cross-sectional view in FIG. 1;

FIG. 3 is a longitudinal cross-sectional view of the lancet device of FIG. 1 showing the lancet device in an initial stage of actuation;

FIG. 4 is a longitudinal cross-sectional view of the lancet device of FIG. 1 showing the lancet device immediately after actuation;

FIG. 5 is a longitudinal cross-sectional view of the lancet device of FIG. 1 showing the lancet device after actuation with a lancet of device partially exposed for a puncturing procedure;

FIG. 6 is a longitudinal cross-sectional view of the lancet device of FIG. 1 showing the lancet device in a final state after actuation;

FIG. 7 is a longitudinal cross-sectional view of a second embodiment of the lancet device showing the lancet device in the initial, pre-actuated state;

FIG. 8 is a longitudinal cross-sectional view of the lancet device of FIG. 7 taken along a perpendicular longitudinal axis to the cross-sectional view in FIG. 7;

FIG. 9 is a longitudinal cross-sectional view of the lancet device of FIG. 7 showing the lancet device in the initial stage of actuation;

FIG. 10 is a longitudinal cross-sectional view of the lancet device of FIG. 7 with the lancet of device removed for viewing the interior of the device;

FIG. 11 is a longitudinal cross-sectional view of the lancet device of FIG. 7 showing the lancet device after actuation with the lancet of device partially exposed for a puncturing procedure;

FIG. 12 is a longitudinal cross-sectional view of the lancet device of FIG. 7 showing the lancet device in the final state after actuation;

FIG. 19 is a longitudinal cross-sectional view of a fourth embodiment of the lancet device showing the lancet device in the initial, pre-actuated state;

FIG. 20 is a longitudinal cross-sectional view of the lancet device of FIG. 19 showing the lancet device in the initial stage of actuation;

FIG. 21 is a cross-sectional view of the lancet device of FIG. 19 showing the lancet device immediately after actuation;

FIG. 22 is a longitudinal cross-sectional view of the lancet device of FIG. 19 with the lancet of the device removed for viewing the interior of the device;

FIG. 41 is a longitudinal cross-sectional view of the lancet device of FIG. 38 showing the lancet device after actuation with the lancet moving within the device toward a puncturing position;

FIG. 42 is a longitudinal cross-sectional view of the lancet device of FIG. 38 showing the lancet device after actuation with the lancet of device in the puncturing position for a puncturing procedure;

FIG. 44 is a perspective view of an eighth embodiment of the lancet device;

FIG. 45 is a perspective view of the lancet device of FIG. 44 with a sterile cover associated with the internal lancet removed;

FIG. 53 is a perspective view of a further embodiment of the lancet device;

FIGS. 54A-54C are bottom, side, and end views, respectively, of a retaining hub used in the lancet device shown in FIG. 53;

FIG. 57 is a longitudinal cross-sectional view of the lancet device of FIG. 56;

FIG. 58 is a transverse cross-sectional view of the lancet device of FIG. 56 taken along line 58-58 in FIG. 57;

FIG. 59 is an exploded and partial cross-sectional view of the lancet device of FIG. 56 showing a rear cap, guide plate and shield of the lancet device;

FIGS. 65A and 65B are longitudinal and transverse cross-sectional views, respectively, of the lancet device of FIG. 56 showing the lancet device in an initial, pre-actuated state;

FIGS. 67A and 67B are longitudinal and transverse cross-sectional views, respectively, of the lancet device of FIG. 56 showing the lancet device at the point of actuation.

DESCRIPTION OF THE PREFERRED EMBODIMENTS

Figure 13:
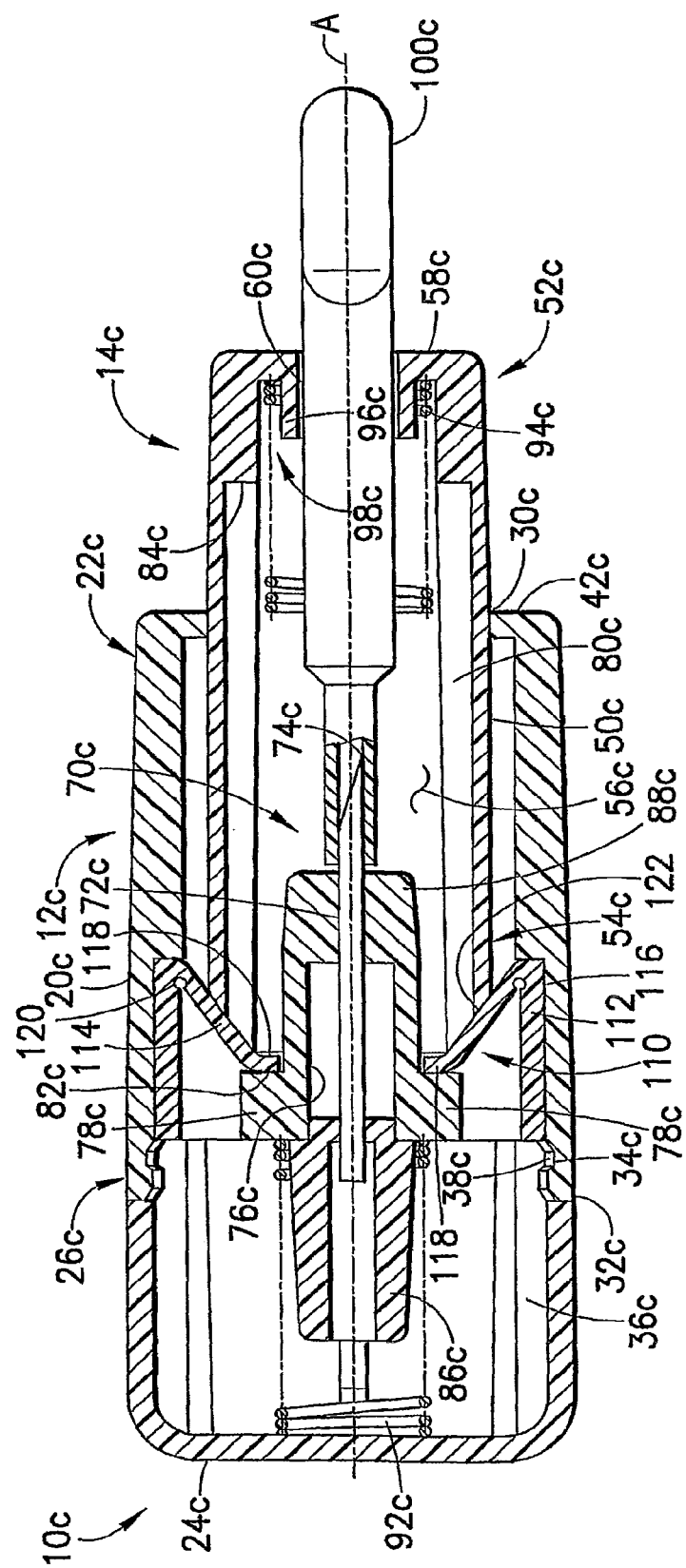
FIG. 13 is a longitudinal cross-sectional view of a third embodiment of the lancet device showing the lancet device in the initial, pre-actuated state.
Figure 14:
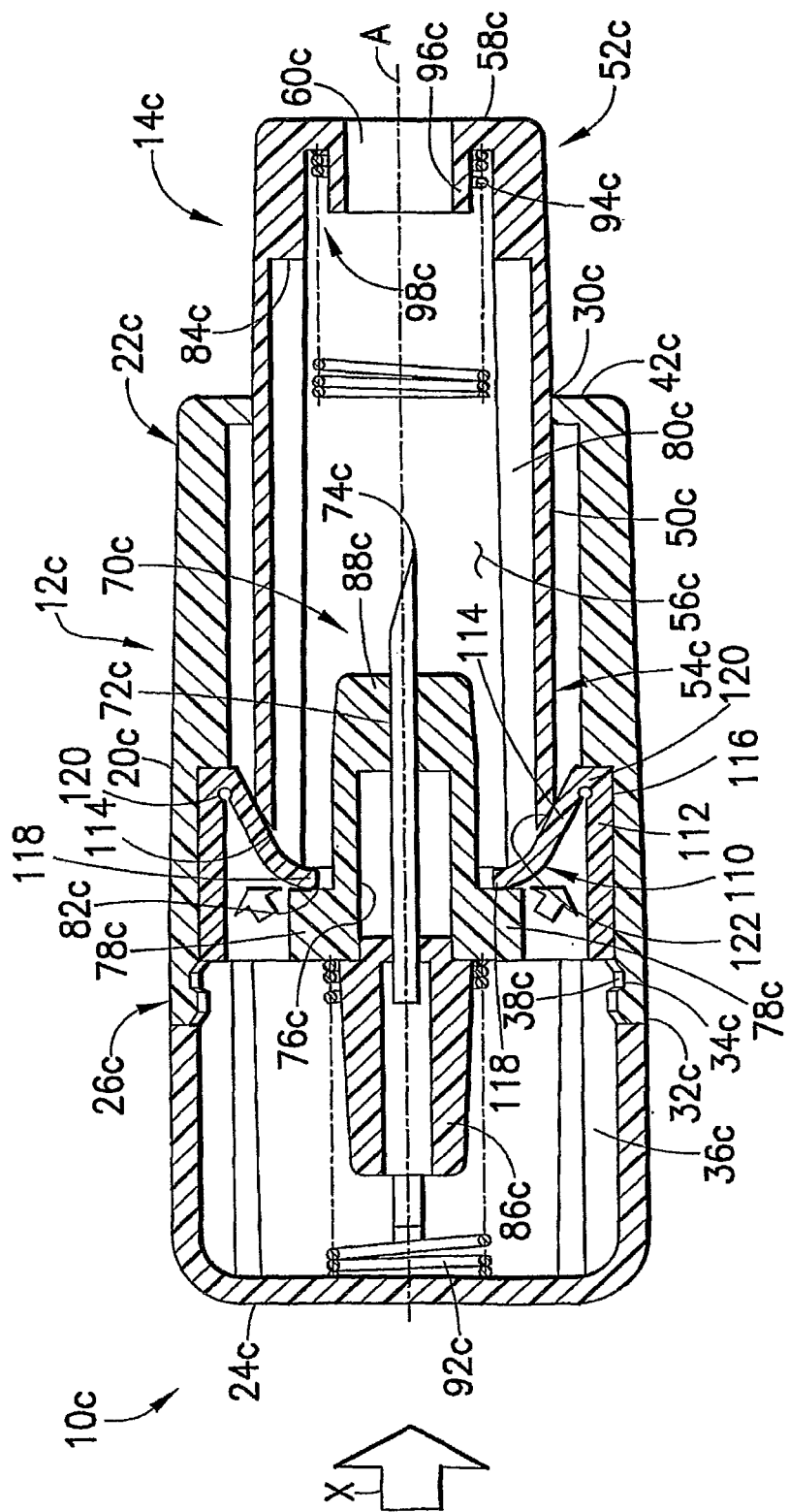
FIG. 14 is a longitudinal cross-sectional view of the lancet device of FIG. 13 showing the lancet device in the initial stage of actuation.
Figure 15:
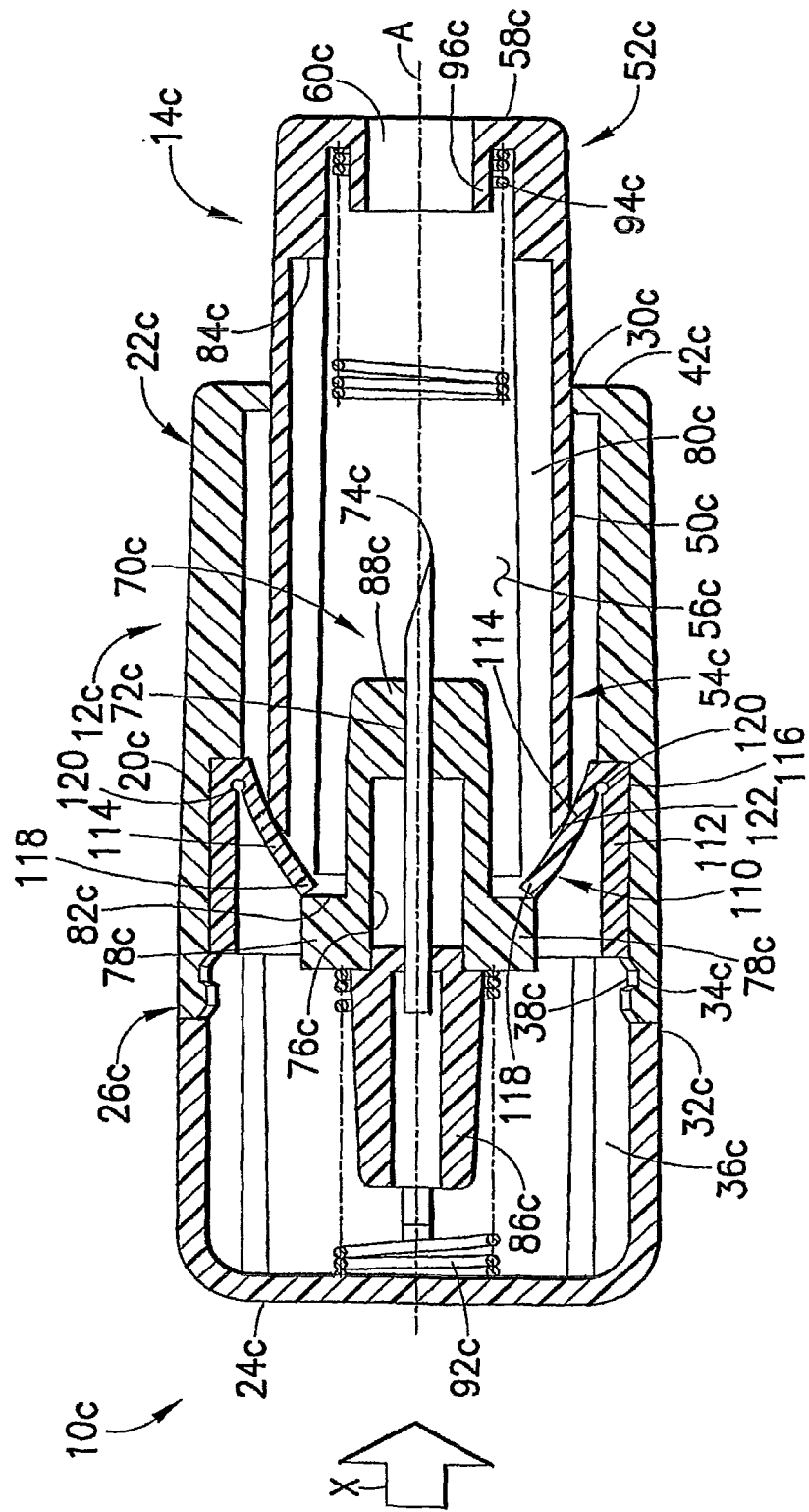
FIG. 15 is a longitudinal cross-sectional view of the lancet device of FIG. 13 showing the lancet device in a later stage of actuation.
Figure 16:
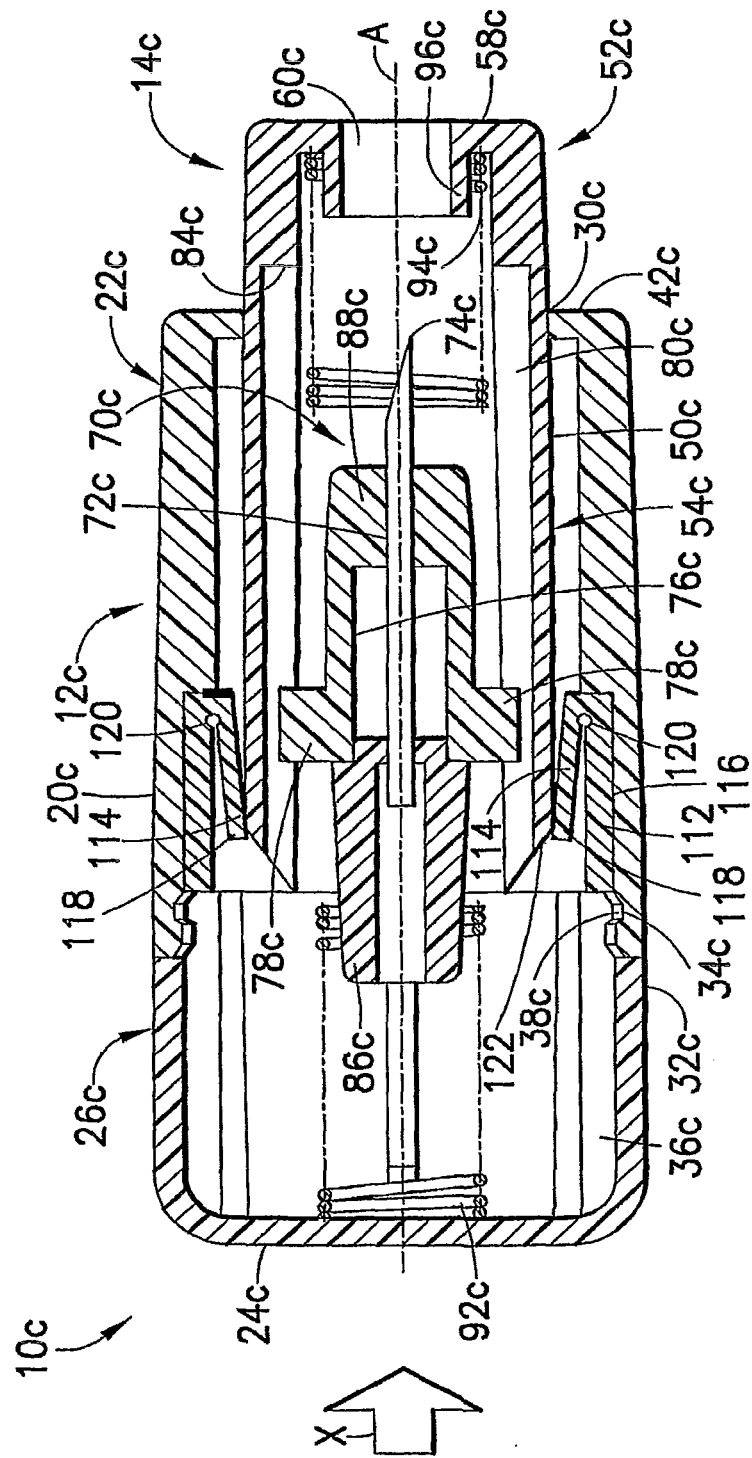
FIG. 16 is a cross-sectional view of the lancet device of FIG. 13 showing the lancet device immediately after actuation.
Figure 17:
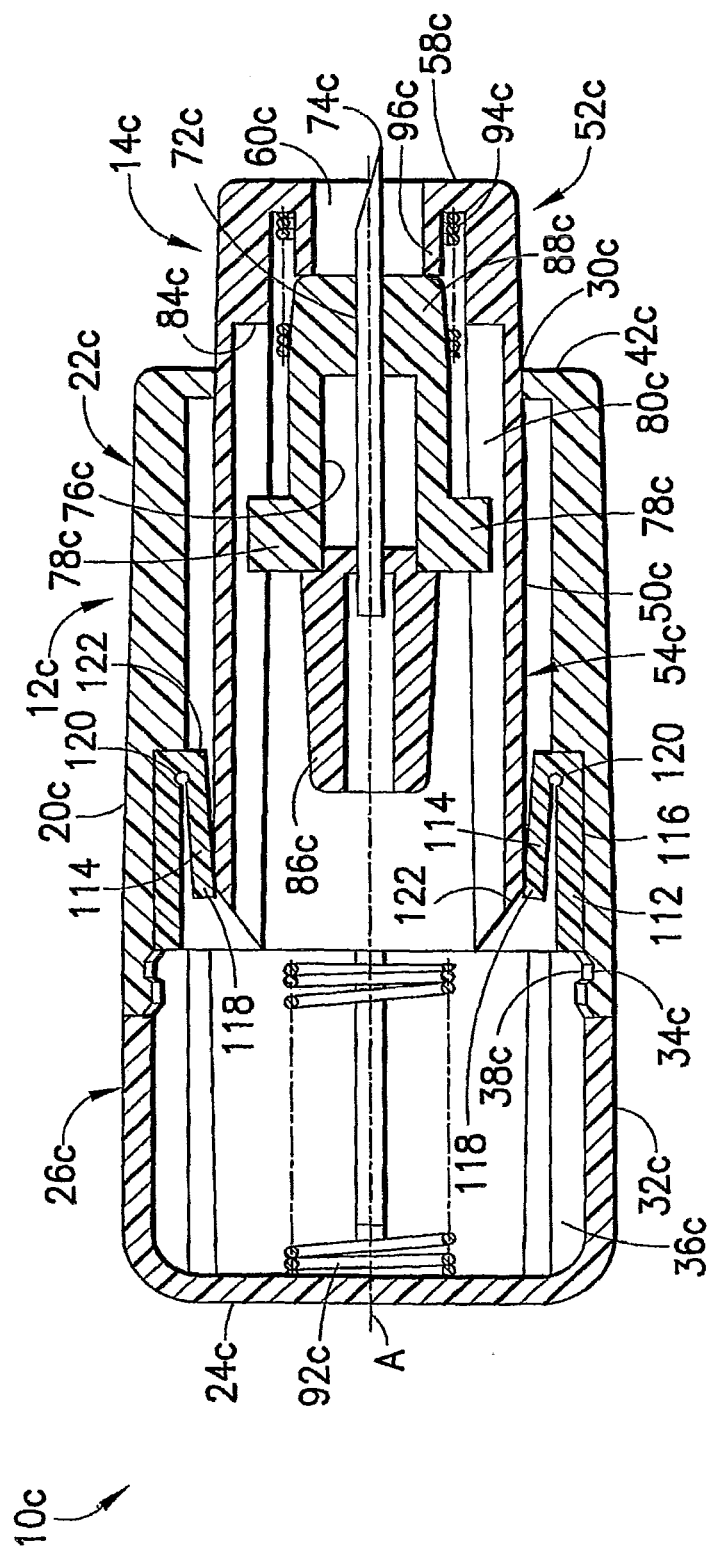
FIG. 17 is a longitudinal cross-sectional view of the lancet device of FIG. 13 showing the lancet device after actuation with the lancet of the device partially exposed for a puncturing procedure.
Figure 18:
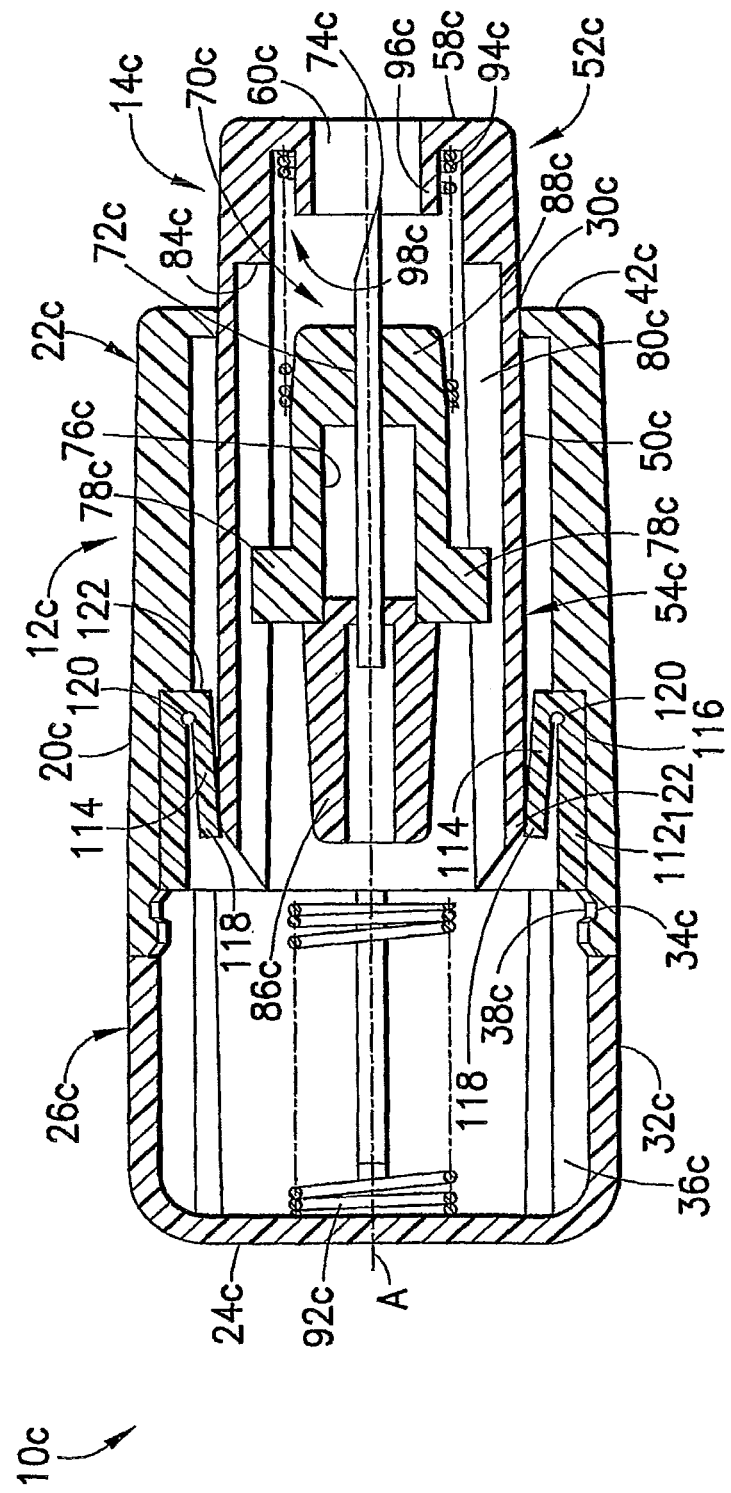
FIG. 18 is a longitudinal cross-sectional view of the lancet device of FIG. 13 showing the lancet device in the final state after actuation.
Figure 23:
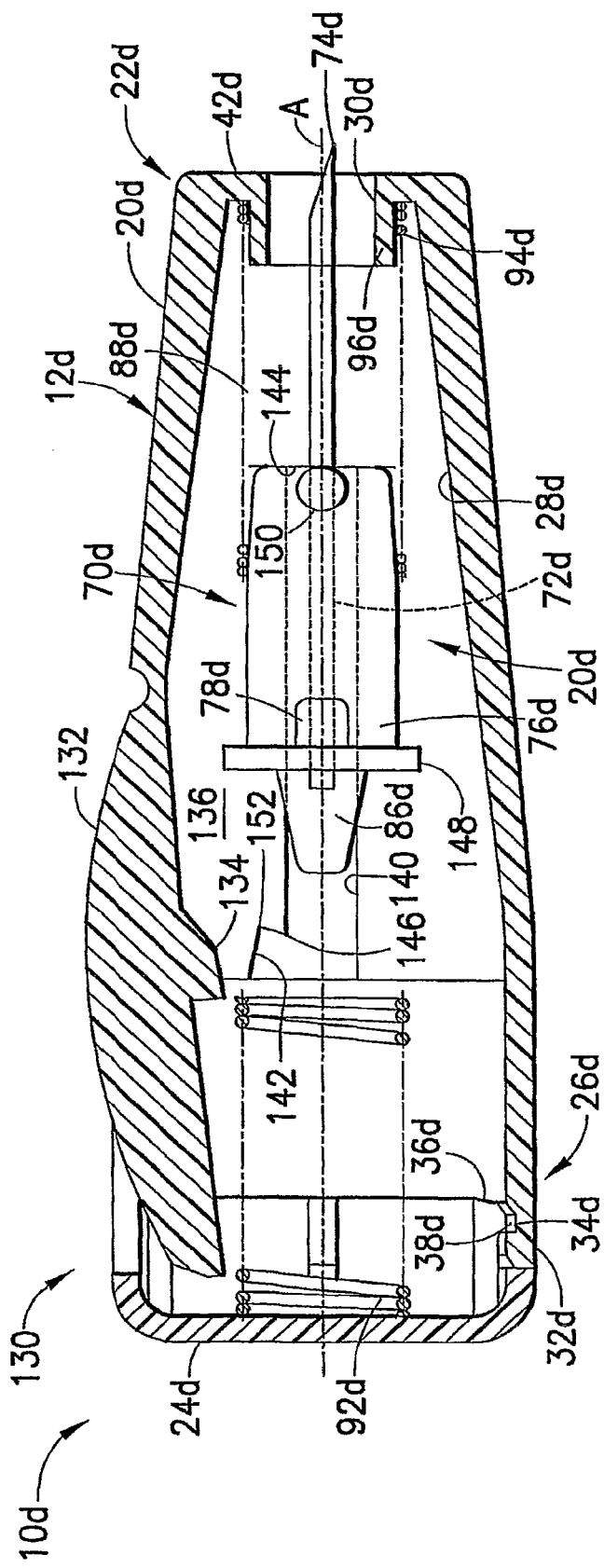
FIG. 23 is a longitudinal cross-sectional view of the lancet device of FIG. 19 showing the lancet device after actuation with the lancet of the device partially exposed for a puncturing procedure.
Figure 24:
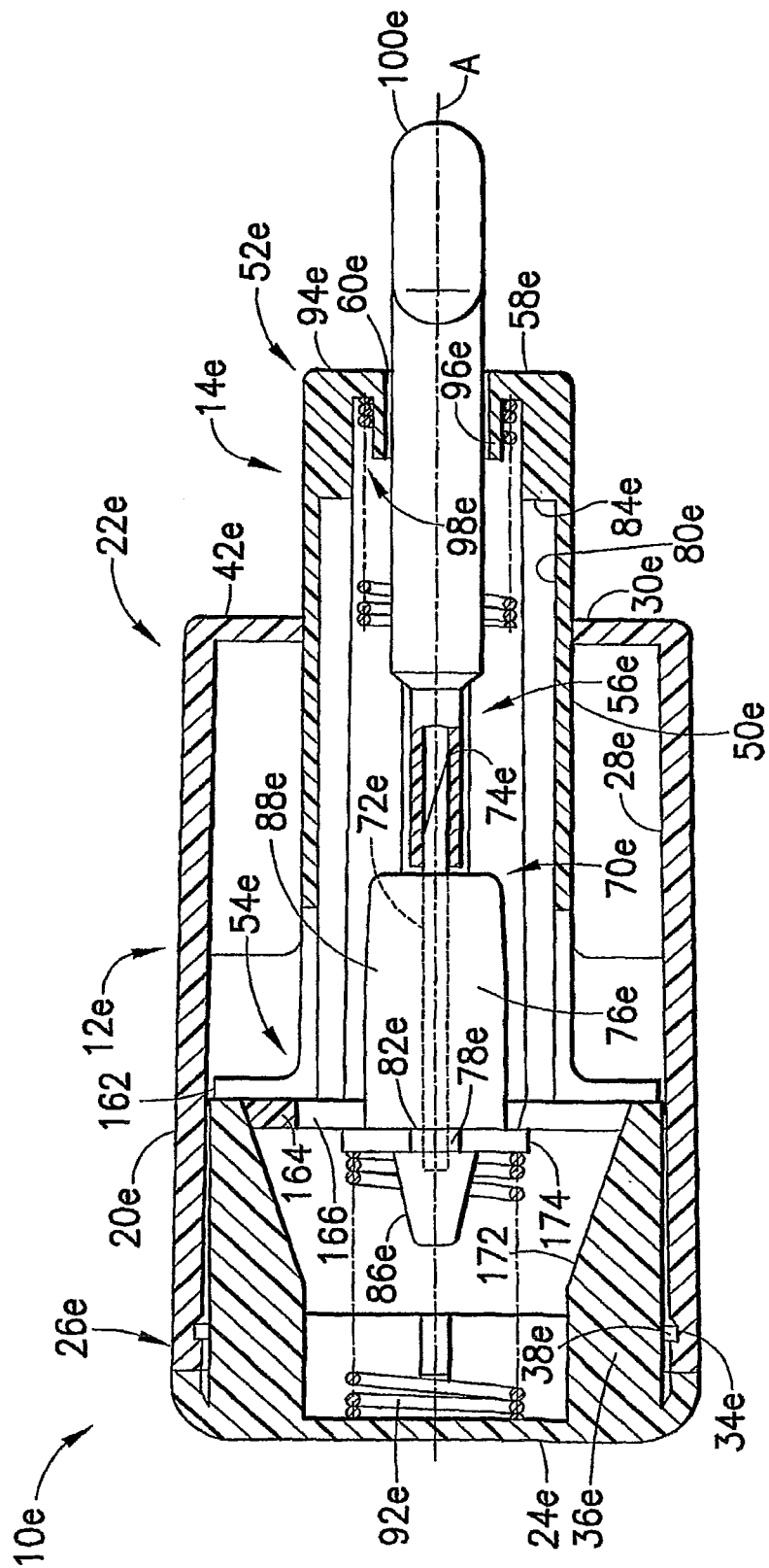
FIG. 24 is a longitudinal cross-sectional view of a fifth embodiment of the lancet device showing the lancet device in the initial, pre-actuated state.
Figure 25:
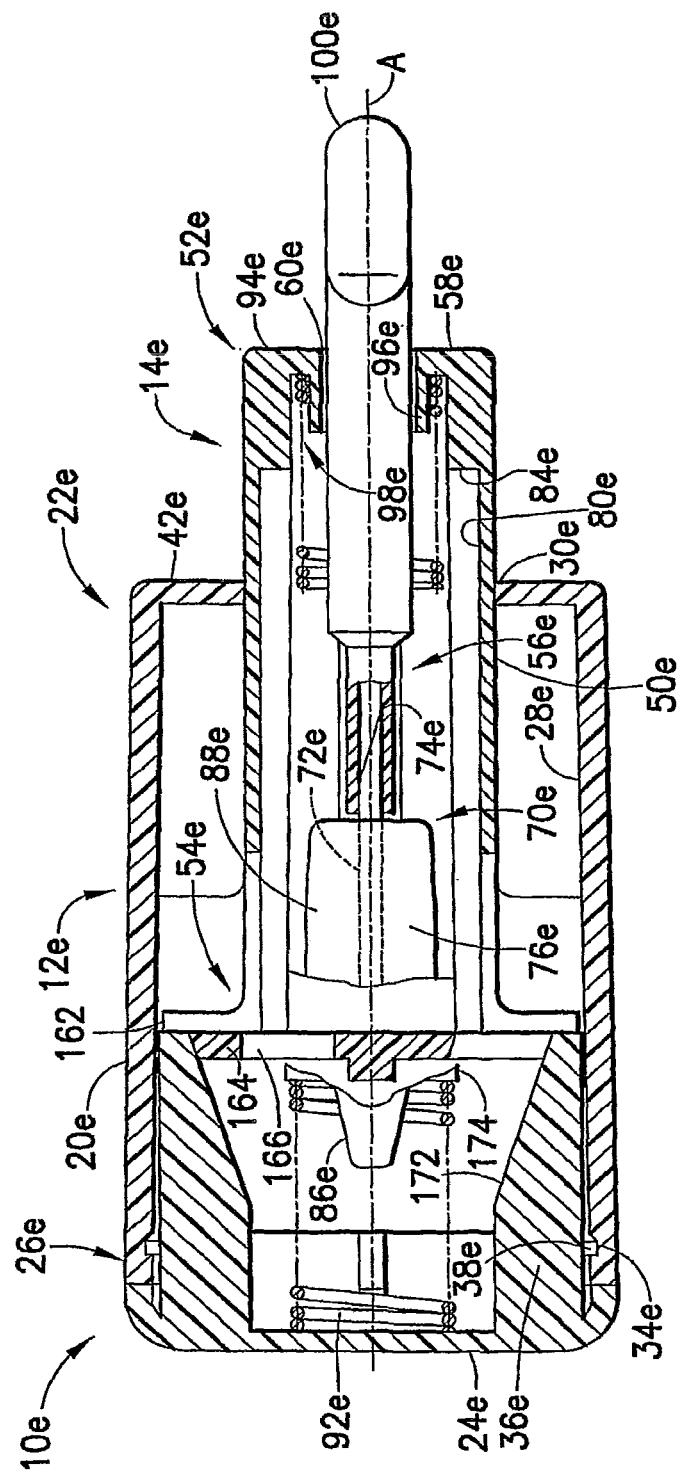
FIG. 25 is longitudinal cross-sectional view of the lancet device of FIG. 24 taken along a perpendicular longitudinal axis to the cross-sectional view in FIG. 24.
Figure 26:
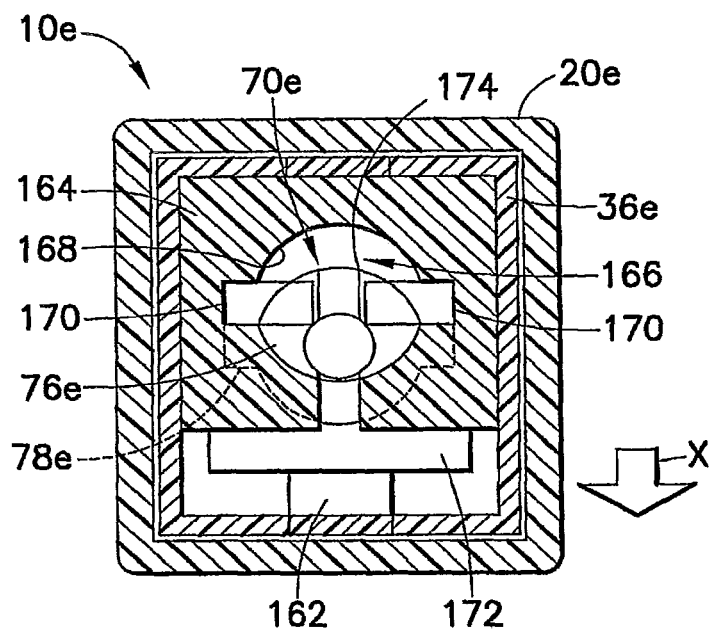
FIG. 26 is a transverse cross-sectional view of the lancet device of FIG. 24 showing the lancet device in the initial stage of actuation with the lancet in an interference engagement within the device.
Figure 27:
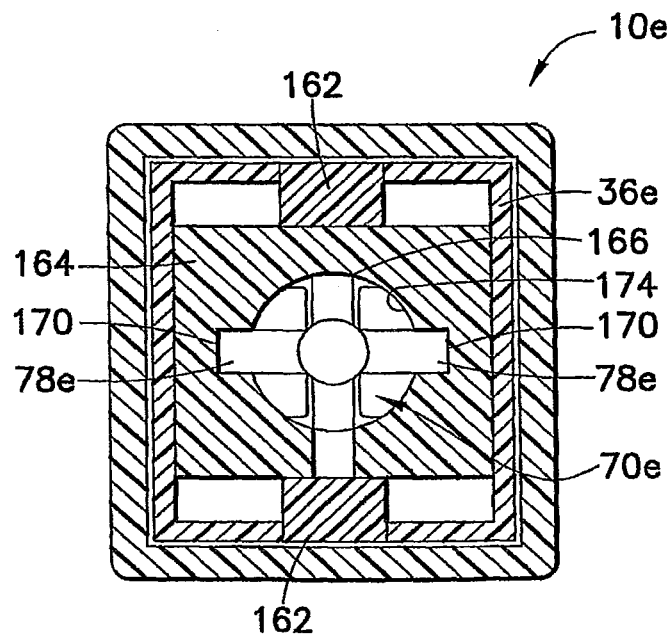
FIG. 27 is a transverse cross-sectional view of the lancet device of FIG. 24 showing the lancet device at the point of actuation with the lancet released of the interference engagement within the device.
Figure 28:
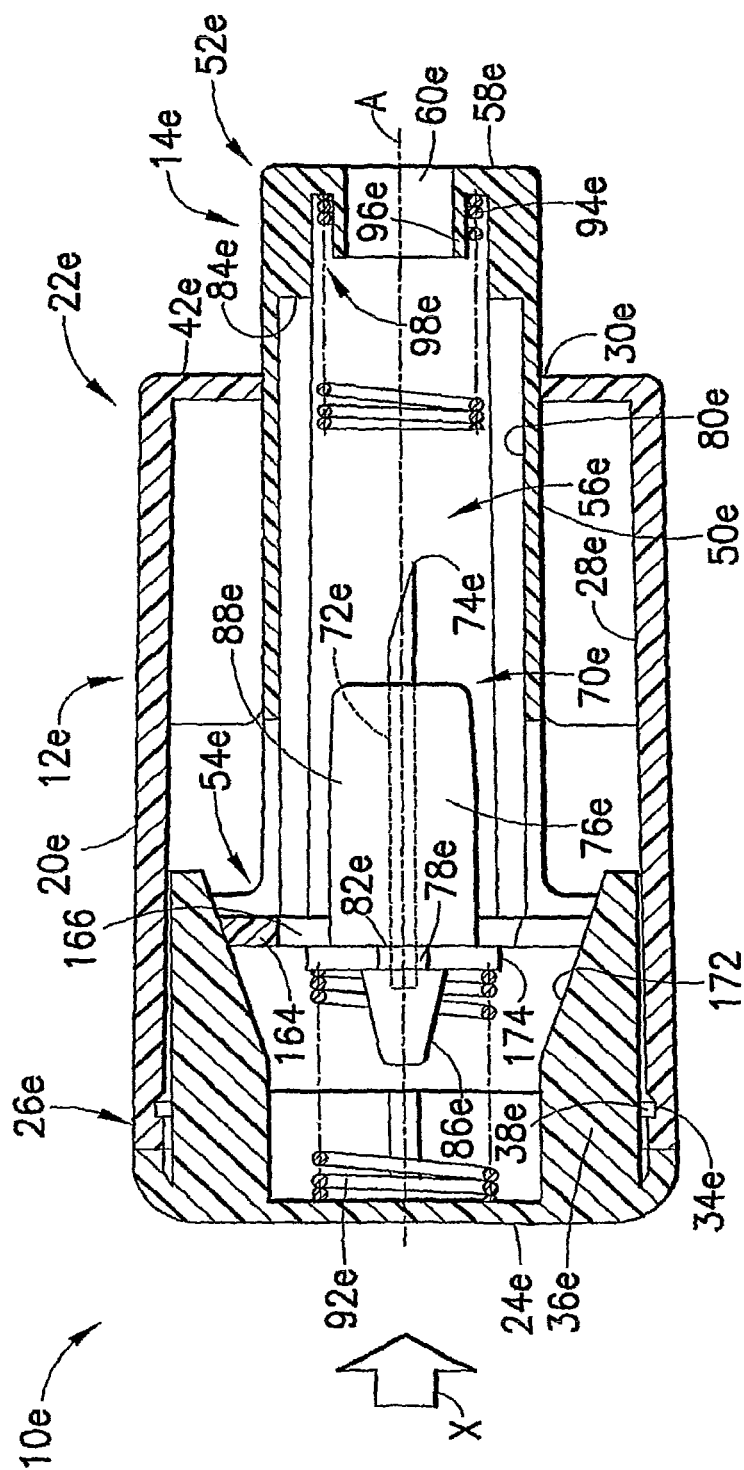
FIG. 28 is a longitudinal cross-sectional view of the lancet device of FIG. 24 showing the lancet device in the initial stage of actuation
Figure 29:
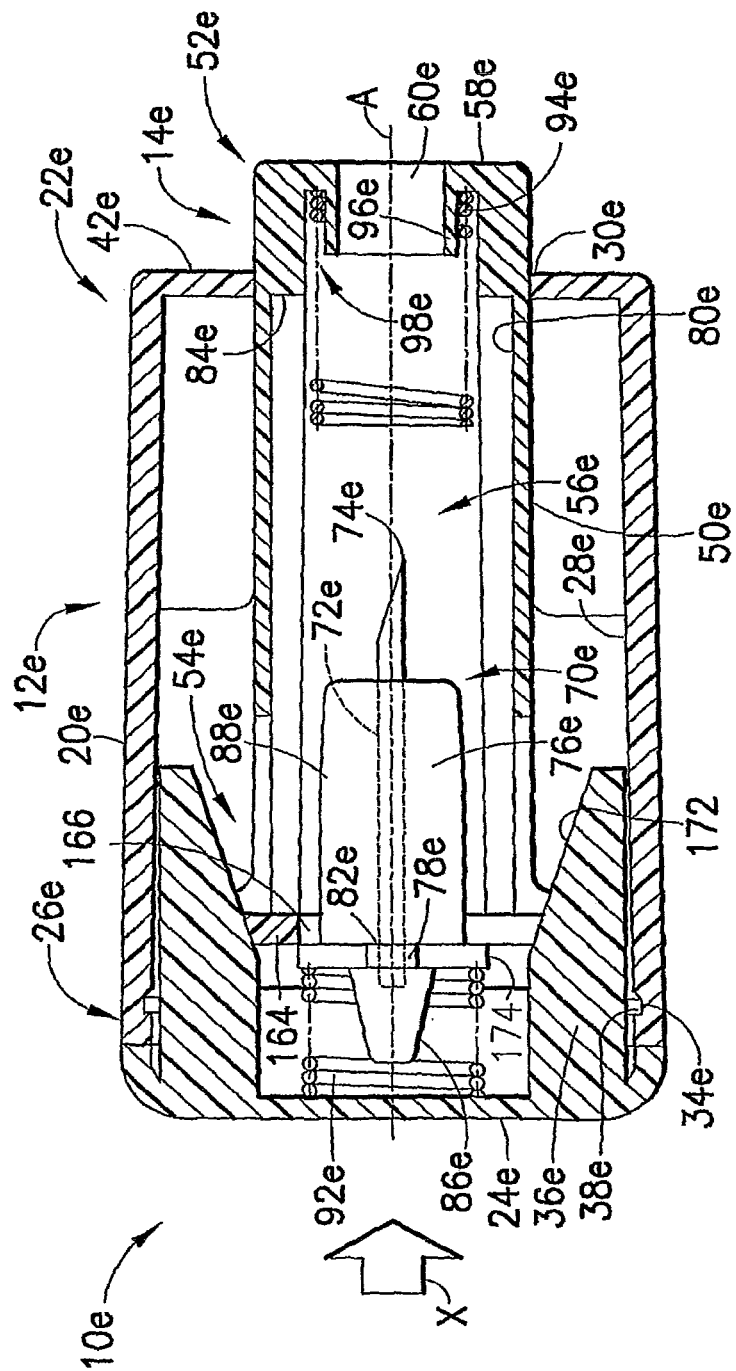
FIG. 29 is a longitudinal cross-sectional view of the lancet device of FIG. 24 showing the lancet device at the point of actuation.
Figure 30:
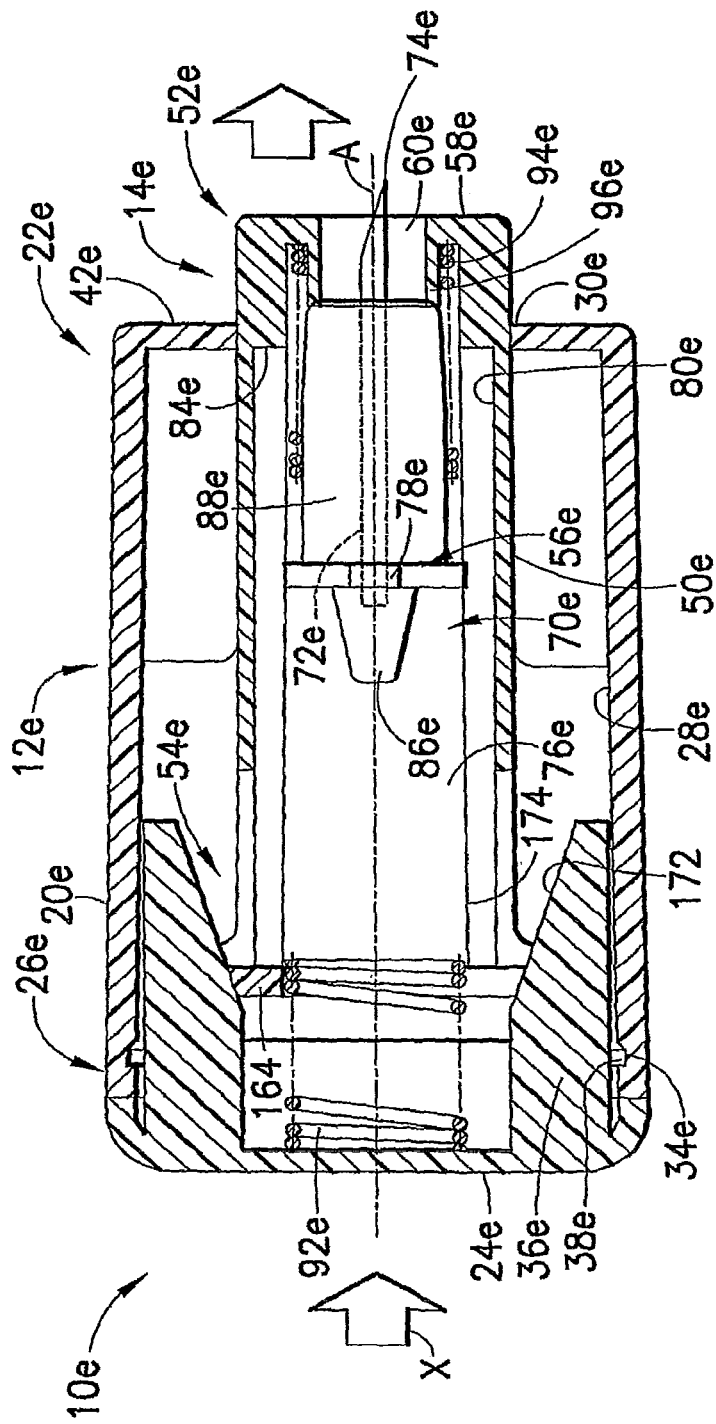
FIG. 30 is a longitudinal cross-sectional view of the lancet device of FIG. 24 showing the lancet device after actuation with the lancet of the device partially exposed for a puncturing procedure.
Figure 31:
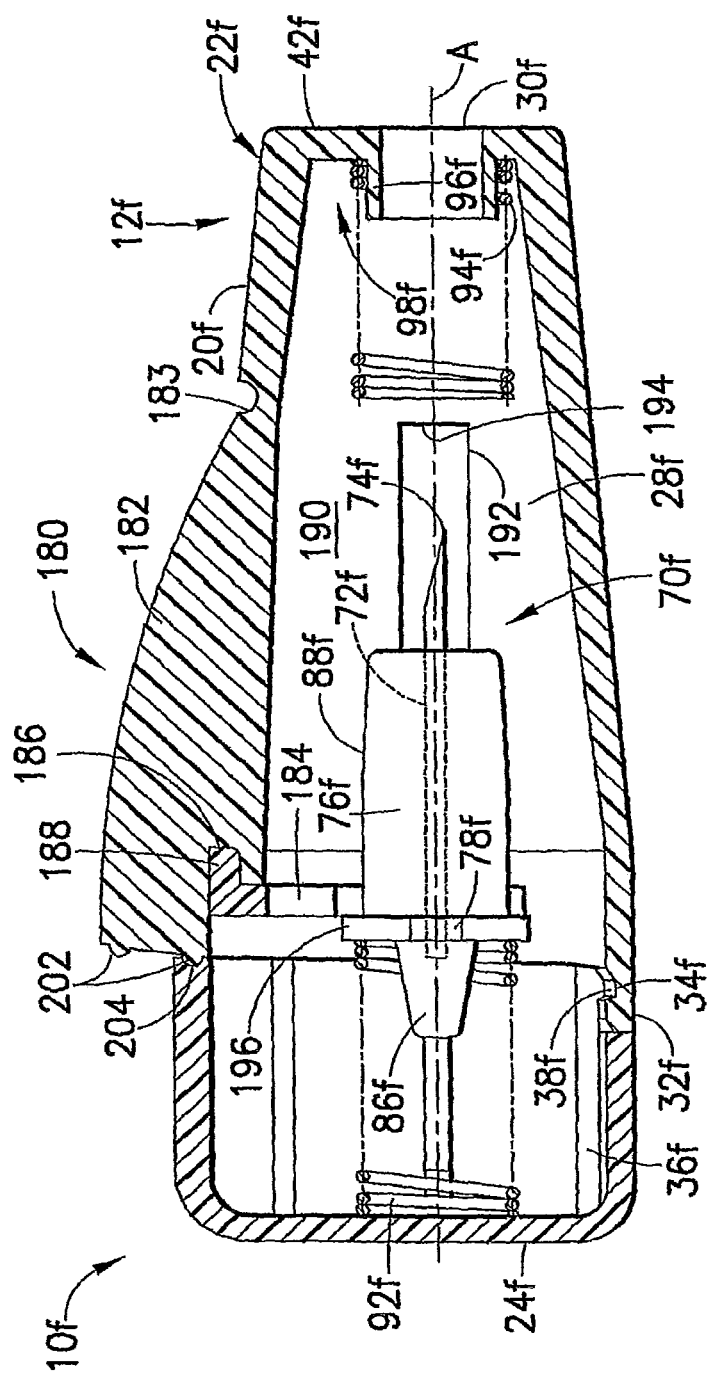
FIG. 31 is a longitudinal cross-sectional view of a sixth embodiment of the lancet device showing the lancet device in the initial, pre-actuated state.
Figure 32:
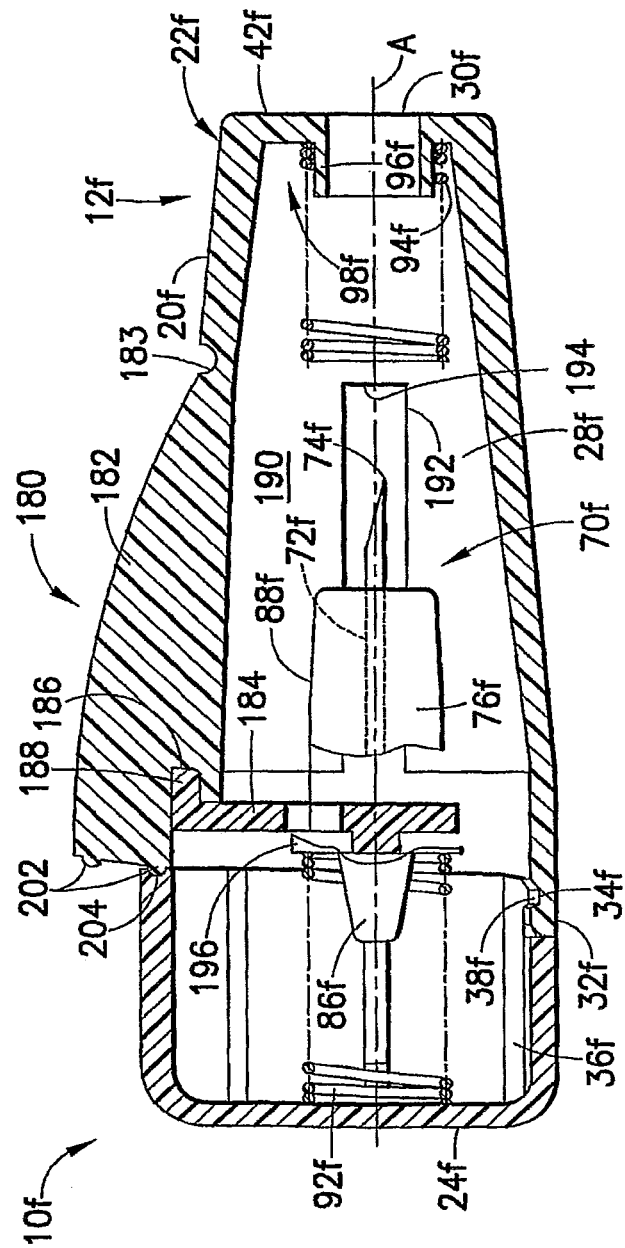
FIG. 32 is a second longitudinal cross-sectional view of the lancet device of FIG. 31 showing the lancet device in the initial, pre-actuated state.
Figure 33:
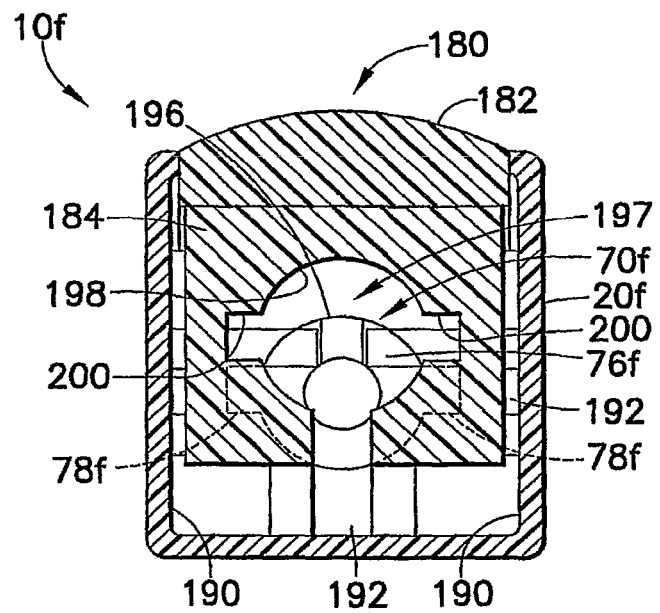
FIG. 33 is a transverse cross-sectional view of the lancet device of FIG. 31 showing the lancet device in the initial stage of actuation with the lancet in an interference engagement within the device.
Figure 34:
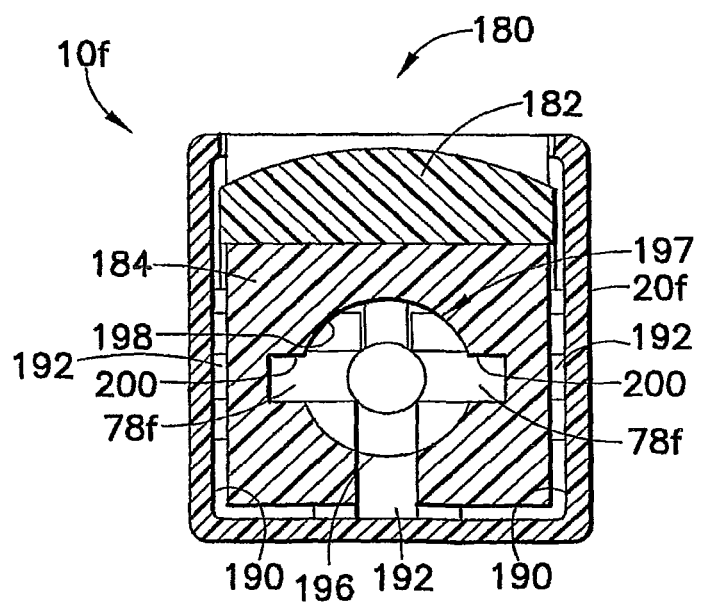
FIG. 34 is a transverse cross-sectional view of the lancet device of FIG. 31 showing the lancet device at the point of actuation with the lancet released of the interference engagement within the device.

For purposes of the description hereinafter, spatial orientation terms, if used, shall relate to the embodiment of the invention as it is oriented in the accompanying drawing figures. However, it is to be understood that the invention may assume many alternative variations and embodiments except where expressly specified to the contrary. It is also to be understood that the specific devices and embodiments illustrated in the accompanying drawing figures and described herein are simply exemplary embodiments of the invention, and wherein like elements are designated with like reference numerals and an accompanying alphabetic designation.

Referring to FIGS. 1-6, a lancet device 10a according to a first embodiment is generally shown. The lancet device 10a generally includes a housing 12a, a shield 14a movably associated with the housing 12a, and a lancet 70a movably disposed in the housing 12a. As described in greater detail herein, shield 14a is movably associated with the housing 12a, and is at least partially disposed within housing 12a. The shield 14a typically extends partially outward from the housing 12a, while the lancet 70a is contained within housing 12a and is axially movable through the shield 14a.

The housing 12a is generally in the form of an elongated body, referred to hereinafter as main body 20a. The main body 20a has a generally cylindrical and hollow configuration. The main body 20a has a distal or forward end portion 22a, and a rear cap 24a forming a proximal or rearward end portion 26a of the main body 20a. The interior of main body 20a is generally open and comprises an internal cavity or bore 28a. The internal cavity 28a is closed at the rearward end due to the presence of rear cap 24a, and includes a front opening 30a defined by a forward end portion 22a of main body 20a, and through which shield 14a extends. Main body 20a and rear cap 24a may be integrally formed. Alternatively, main body 20a and rear cap 24a may be separate elements that are affixed together to form housing 12a, which facilitates assembly of lancet device 10a. As examples, main body 20a and rear cap 24a may be affixed together through an appropriate medical grade adhesive, or connected using inter-engaging structures providing a mechanical engagement therebetween, such as a friction-fit or a snap-fit connection. For example, main body 20a may include an annular rim 32a defining an annular groove 34a, and rear cap 24a may include a mating annular rim 36a having a mating annular lip 38a as mating elements. When main body 20a and rear cap 24a are connected, annular lip 38a extends within the rear open end of main body 20a, with annular lip 38a snap-fitting over annular rim 32a and into annular groove 34a of main body 20. It should be understood that the arrangement of such elements is merely exemplary and may be reversed, and it is contemplated that other inter-fitting mechanical engagement arrangements may be used to connect the main body 20a and rear cap 24a. Main body 20a further comprises an internal ridge 40a, typically a perimetrically-extending ridge 40a forward of annular groove 34a, the purpose and function of which will be described herein. Further, main body 20a of housing 12a may include a forward rim 42a formed as part of forward end portion 22a and which defines front opening 30a.

As noted previously, shield 14a extends outward at least partially from front opening 30a in the forward end portion 22a of main body 20a. Shield 14a is a generally cylindrical, hollow structure comprising a shield body 50a having a distal or forward end 52a and a proximal or rearward end 54a, and defines an internal cavity or bore 56a extending therethrough. The forward end 52a of shield body 50a defines a partial forward end wall 58a defining a forward opening 60a, through which a puncturing element of lancet 70a extends when lancet device 10a is actuated by a user as will be discussed in more detail herein. The forward end wall 58a generally defines a small contact area about forward opening 60a for contacting an intended puncture area on a patient's body. The reduced contact area may be made smaller (i.e., reduced in surface area) by providing a plurality of peripheral indentations (not shown) formed perimetrically in shield 14a. The external surface features of housing 12a and shield 14a may be formed in accordance with the ergonomic features and structure disclosed in co-pending application Ser. No. 11/123,849, filed Nov. 30, 2004, entitled "Lancet Device", and naming Bradley Wilkinson as inventor. The disclosure of the foregoing "Lancet Device" application is incorporated herein by reference thereto.

The shield 14a is axially and slidably movable within housing 12a. The shield 14a and housing 12a may be coaxially associated, with the shield 14a and housing 12a coaxially disposed around a common Central Axis A. The shield 14a and housing 12a may each be generally cylindrically shaped. A shearable element 62a is further associated with shield 14a. In particular, shearable element 62a is disposed at the rearward end Ma of shield body 50a and engages a rear rim 63a of shield body 50a. Shearable element 62a comprises an annular sleeve portion 64a that extends axially in a distal direction along the outer surface of shield body 50a. The annular sleeve 64a receives the rearward end 54a of shield body 50a so as to be positioned between shield body 50a and main body 20a of housing 12a. In particular, the inner surface of annular sleeve 64a engages a proximally-extending portion of the outer surface of shield body 50a at the rearward end 54a of shield body 50a, while the outer surface of shearable element 62a slidably cooperates with the inner surface of main body 20a of housing 12a. Shearable element 62a further typically comprises two opposing and inward-projecting breakable shelves or wings 66a that engage lancet 70a as described further herein. While shearable element 62a is shown with two opposing and inward-extending shelves or wings 66a, it will be appreciated that only one shelf or wing 66a is necessary for interference engagement with the lancet 70a as described herein. Breakable shelves or wings 66a may comprise a weakened area or score line 67a for allowing the shelves 66a to break (i.e., fail) when sufficient downward pressure is applied thereto as discussed herein. Breakable shelves or wings 66a are generally inwardly radially-extending cantilevers which may be made of a similar or dissimilar material compared to that chosen for shield 14a.

Shearable element 62a is adapted to slide in combination with shield body 50a in main body 20a of housing 12a when axial motion is imparted to shield body 50a, for example by axially retracting (i.e., inserting) shield body 50a into main body 20a to actuate the lancet device 10a as described herein. For this purpose and to properly engage the rear rim 63a on the rearward end 54a of shield body 50a, shearable element 62a comprises an abutment recess 68a defined by sleeve portion 64a which engages the proximal or rearward end 54a of shield body 50a, and rear rim 63a in particular. Accordingly, any axial motion applied to shield body 50a to retract (i.e., insert) shield body 50a into main body 20a of housing 12a will be transmitted to shearable element 62a through the interference engagement of rear rim 63a in abutment recess 68a. As a result, shearable element 62a will slide within main body 20a of housing 12a along with shield body 50a when axial motion applied thereto for actuating the lancet device 10a. The captured portion of shield body 50a may be secured in sleeve portion 64a of shearable element 62a so that there is tight engagement between these elements and ensuring that axial motion imparted to shield body 50a will be transmitted to shearable element 62a. For example, a medical grade adhesive or mechanical locking engagement may be provided between the inner surface of sleeve portion 64a and the captured portion (i.e., outer surface) of shield body 50a at the rearward end 54a of shield body 50a to ensure that these elements are secured together and move as a unit in main body 20a of housing 12a. Forward rim 42a of main body 20a of housing 12a is formed to provide an interference engagement with the distal end of sleeve portion 64a of shearable element 62a to prevent shearable element 62a and, consequently, shield body 50a from axially sliding completely out of housing 12a through front opening 30a.

Lancet device 10a further comprises a lancet 70a disposed within the housing 12a, and extending into shield 14a. Lancet 70a includes a puncturing element shown in the form of a lancet 72a. Lancet 72a comprises a puncturing end 74a at the forward end thereof. Lancet 70a is adapted for axial movement through the internal cavity 56a of shield body 50a between an initial position, wherein the puncturing end 74a is disposed within shield body 50a to a puncturing position wherein the puncturing end 74a extends beyond the forward opening 60a of shield body 50a a sufficient distance to cause a puncture wound in a patient's body. Further details regarding the operation of lancet device 10a and lancet 70a are provided hereinafter.

The puncturing end 74a of lancet 72a is adapted for puncturing the skin of a patient, and may be in the form of a pointed end, needle tip, blade edge, and the like. Puncturing end 74a may include a preferred alignment orientation, such as with a pointed end or a blade aligned in a specific orientation. In such an orientation, shield body 50a and/or main body 20a of housing 12a may include target indicia corresponding to the alignment orientation of puncturing end 74a. Indentations (not shown) in the shield body 50a and/or indentations (not shown) in main body 20a may function as such an alignment orientation, as described in co-pending application Ser. No. 11/123,849, previously incorporated by reference.

Lancet 70a further includes a carrier body 76a supporting lancet 72a at the rearward end thereof. The carrier body 76a and shield body 50a may include corresponding guiding surfaces for guiding the movement of lancet 70a in shield body 50a. For example, carrier body 76a may include guide tabs 78a on an external surface thereof, with shield body 50a defining corresponding guide channels 80a extending longitudinally along an inner surface thereof for accommodating guide tabs 78a slidably therein. The carrier body 76 may include a pair of guide tabs 78a on opposing lateral sides thereof as illustrated, or a single guide tab 78a, and shield body 50a may include a corresponding pair of guide channels 80a extending along opposing inner surfaces thereof corresponding to each of the guide tabs 78a, or a single corresponding guide channel 80a. It is contemplated that the arrangement of the guide tabs and channels 78a, 80a may be reversed, and multiple guide tabs-guide channels 78a, 80a (i.e., three or more) may also be used. The guide tabs 78a and guide channels 80a ensure that lancet 70a is properly aligned within shield body 50a, and guides the sliding axial movement of lancet 70a within shield body 50a and, further, may be used to prevent or resist rotational movement of carrier body 76a in shield body 50a. A distal facing surface 82a on guide tabs 78a engages shelves or wings 66a on shearable element 62a in the initial or pre-actuated state of lancet device 10a until the shelves or wings 66a are broken to release lancet 70a. The carrier body 76a further comprises a proximal or rearward end spring guide 86a and a distal or forward end spring guide 88a for engaging a drive spring and retraction spring, respectively, of lancet device 10a as described herein. Spring guides 86a, 88a may be formed integral with the carrier body 76a or be provided as distinct, separate elements and secured to the body of carrier body 76a by means customary in the medical field as, for example, with medical grade adhesive or direct mechanical attachment.

Movement of the lancet 70a through the lancet device 10a is achieved through a biasing force provided by a drive spring 92a. Drive spring 92a is adapted to exert a biasing force against lancet 70a to drive lancet 70a through the lancet device 10a toward the puncturing position, and is disposed between the rearward end of the housing 12a and the lancet 70a. Rear cap 24a may include structure for alignment of and/or for maintaining drive spring 92a in the proper orientation on rear cap 24a. For example, rear cap 24a may include an internal alignment structure (not shown) for correctly positioning the drive spring 92a. The lancet 70a, as indicated previously, includes proximal spring guide 86a which engages the opposite end of drive spring 92a in the initial or pre-actuated state of lancet device 10a. In the initial state of lancet device 10a, drive spring 92a extends between rear cap 24a and distal spring guide 86a of carrier body 76a. When the lancet 70a is in the initial, pre-actuated state, drive spring 92a is in a substantially unloaded, relaxed condition and exerts little to no biasing force on lancet 70a. Upon compressing or "loading" the drive spring 92a, the lancet device 10a is placed into an armed or loaded state ready for a puncturing procedure as described in detail herein.

A retraction or return spring 94a may further be provided at the forward or distal end of the lancet device 10a, for retracting the lancet 70a within the shield body 50a after the lancet 70a has moved distally to the puncturing position wherein the puncturing element 74a extends outward from the distal or forward end 54a of shield body 50a a sufficient distance to cause a puncture wound in the patient. Retraction spring 94a is adapted to be engaged by distal spring guide 88a extending forward from carrier body 76a during the forward movement of lancet 70a, as described herein. The forward or distal end wall 58a of shield body 50a further comprises an axially rearward, or proximally-extending internal sleeve 96a which defines a distal end pocket 98 for receiving retraction spring 94a. The retraction spring 94a is disposed in distal end pocket 98a throughout the operation sequence of lancet device 10a in a puncturing procedure. The retraction spring 94a may be secured in distal end pocket 98a through use of a medical grade adhesive or by mechanically securing retraction spring 94a in distal end pocket 98a. The drive and retraction springs 92a, 94a are typically compression springs capable of storing potential energy when in a compressed state.

Lancet device 10a may further include a protective tab or cover 100a for protectively covering the forward end of the lancet 70a and, in particular, the puncturing end 74a of lancet 72a. The tab or cover 100a protectively covers puncturing end 74a to maintain sterility thereof prior to use. The tab or cover 100a is typically a relatively thin and elongated structure that extends from carrier body 76a through the forward opening 60a in shield body 50a for grasping by a user of the lancet device 10a. Tab or cover 100a may be integrally formed with the body of carrier body 76a, for example, by being integrally formed with carrier body 76a during a plastic molding process. The connection between tab or cover 100a and carrier body 76a may include a weakened area in the form of a perimeter groove or score line, along which the tab or cover 100a is intended to break to remove the cover 100a from carrier body 76a. The tab or cover 100a, as depicted, extends forward from distal spring guide 88a of carrier body 76a. Tab or cover 100a is sized to extend axially through retraction spring 94a. Various configurations of the tab or cover 100a are described in co-pending application Ser. No. 11/123,849, previously incorporated by reference.

The respective elements of the lancet device 10a are all typically formed of molded plastic material, such as a medical grade plastic material. The lancet 72a may be constructed of any suitable material adapted for puncturing the skin, and is typically a surgical grade metal such as stainless steel.

Use and actuation of lancet device 10a will now be described with continued reference to FIGS. 1-6. Lancet device 10a is typically initially provided with cover 100a extending distally from carrier body 76a, and through forward opening 60a in the forward end wall 58a of shield body 50a. In the initial, unarmed state of lancet device 10a, the drive spring 92a is substantially uncompressed (i.e., unloaded) and in a relaxed state. Drive spring 92a extends from the inner side of rear cap 24a to the carrier body 76a and, more particularly, is disposed about proximal spring guide 86a of carrier body 76a. To use the lancet device 10a in a puncturing procedure, the drive spring 92a must be compressed and placed into a compressed, armed state to provide the biasing force needed to move the lancet 70a through housing 12a and shield 14a. Further, in the initial state, the drive spring 92a acts on spring guide 86a substantially only to position lancet 70a within main body 20a of housing 12a. More particularly, drive spring 92a positions carrier body 76a at a relatively fixed and stationary position within main body 20a of housing 12a, wherein the lancet 70a occupies a generally fixed position relative to main body 20a of housing 12a and shield body 50a of shield 14a. Further, drive spring 92a acting on spring guide 86a of carrier body 76a positions the carrier body 76a such that guide tabs 78a extending laterally from carrier body 76a contact cantilevered shelves or wings 66a on shearable element 62a, which further serves to position shearable element 62a and shield body 50a at a substantially fixed position relative to main body 20a. In particular, the drive spring 92a acts on carrier body 76a to position carrier body 76a such that the distal surface 82a on guide tabs 86a is in interference engagement with shelves 66a, and positions the shearable element 62a and shield body 50a at a generally fixed position relative to main body 20a. Accordingly, until the user is ready to use the lancet device 10a, shearable element 62a and shield body 50a are kept at a substantially constant relative position with respect to main body 20a.

To use the lancet device 10a, the user grasps opposing sides of housing 12a, such as between a finger and thumb, and removes breakable cover 100a. Cover 100a is removed typically by moving cover 100a in a combined twisting and pulling motion in forward opening 60a defined in forward end wall 58a of shield body 50a to break the frangible connection with carrier body 76a. Once the frangible connection is broken, the cover 100a may be removed through the forward opening 60a. The forward end wall 58a of shield body 50a may then be placed in contact with a location on the patient's body where it is desired to cause a puncture injury to initiate blood flow. If provided, target indicia may be aligned with the desired location of puncture.

Once placed against the body, the user exerts a downwardly directed force on main body 20a of housing 12a forcing shield body 50a of shield 14a to retract (i.e., depress) into housing 12a. In particular, the user applies a downward directed force in the direction of Arrow X, thereby applying a force against the user's body (i.e., skin surface). Such force establishes an opposing force on forward end wall 58a of shield body 50a causing shield body 50a to retract axially and proximally within main body 20a of housing 12a. As shield body 50a retracts into main body 20a, rearward end 54a of shield body 50a moves proximally (i.e., rearward) toward rear cap 24a. The interference engagement between abutment recess 68a on shearable element 62a and the rear rim 63a at the rearward end 54a of shield body 50a causes shearable element 62a to move in combination with shield body 50a toward rear cap 24a. Substantially simultaneously, the interference engagement between guide tabs 78a and shelves or wings 66a begins to exert compressive pressure or force on drive spring 92a. In particular, as the user applies downward force on housing 12a, shield body 50a and shearable element 62a move rearward and transmit the opposing force to drive spring 92a through the interference engagement between distal end surface 82a on guide tabs 78a and shelves 66a, thereby beginning to compress drive spring 92a between rear cap 24a and carrier body 76a.

As the entire lancet 70a continues to move rearward, the interference engagement between guide tabs 78a and shelves 66a compresses drive spring 92a between rear cap 24a and carrier body 76a and, more particularly, between proximal spring guide 86a and rear cap 24a. While the shelves or wings 66a are intentionally formed to be broken (i.e., frangible), the shelves 66a are formed with sufficient strength to withstand the force required to axially compress drive spring 92a between proximal spring guide 86a and rear cap 24a a pre-selected distance without breaking. Further downward movement of main body 20a of housing 12a eventually causes the proximal spring guide 86a to contact or "bottom out" against the inner side of rear cap 24a. At this point, drive spring 92a substantially reaches its maximum compression between proximal spring guide 86a and rear cap 24a and the lancet device 10a is now "armed" or "loaded" sufficiently to carry out a puncturing procedure. Optionally, spring guide 86a does not need to contact or "bottom out" against the inner side of rear cap 24a, and drive spring 92a may have sufficient stored potential energy to carry out the actuation of lancet device 10a.

Once the proximal spring guide 86a contacts the inner side of rear cap 24a, continued downward force applied to main body 20a of housing 12a is applied entirely to breakable shelves or wings 66a through the interference engagement with guide tabs 78a. In particular, once the proximal spring guide 86a contacts rear cap 24a, the user's entire downward applied force is transmitted from main body 20a (i.e., rear cap 24a) to carrier body 76a and, accordingly, guide tabs 78a. The interference engagement between guide tabs 78a and shelves 66a focuses the downward applied force on the shelves 66a, which will cause the shelves 66a to yield, shear, or break (i.e., fail) in a distal or forward direction at weakened area 67a and into internal cavity 56a of shield body 50a. At the moment the shelves or wings 66a break, the restraining or compression force previously applied to drive spring 92a due to the interference engagement between guide tabs 78a and shelves 66a is released, releasing the stored potential energy in drive spring 92a to allow the drive spring 92a to move lancet 70a forward in shield body 50a. Additionally, with the interference engagement broken between the guide tabs 78a and shelves 66a removed, the shearable element 62a and shield body 50a are free to retract rearward to engage annular rim 36a on rear cap 24a where their further rearward movement thereof is halted. As the shearable element 62a and shield body 50a move toward annular rim 36a, shearable element 62a rides over top of annular ridge 40a on the inner surface of main body 20a of housing 12a. The engagement of shearable element 62a with annular ridge 40a increases the frictional engagement between the shearable element 62a and main body 20a of housing 12a, thereby substantially fixing the position of shearable element 62a and shield body 50a relative to main body 20a and inhibiting the shield body 50a from moving forward again in main body 20a. The frictional engagement between the outer surface of shearable element 62a and annular ridge 40a operates substantially as a frictional lock or brake to substantially prevent forward movement of shield body 50a in main body 20a after the shearable element 62a and shield body 50a retract fully into main body 20a and engage rear cap 24a.

With the stored potential energy in compressed drive spring 92a released, the drive spring 92a biases the lancet 70a away from rear cap 24a and through internal cavity 56a in shield body 50a. In particular, with the interference engagement between guide tabs 78a and shelves 66a removed, the biasing force of drive spring 92a propels lancet 70a downward and distally away from the rear cap 24a axially through main body 20a of housing 12a and shield body 50a of shield 14a. During such movement, corresponding guide tabs 78a and guide channels 80a guide lancet 70a axially through shield body 50a. The biasing force acting on lancet 70a is preferably sufficient to cause the puncturing end 74a of lancet 72a to project a sufficient distance and with sufficient kinetic energy from the forward opening 60a in shield body 50a to cause a puncture wound in the desired location on a patient's body. Moreover, during the propelling movement of lancet 70a, proximal spring guide 86a on carrier body 76a of lancet 70a releases from drive spring 92a which remains connected to rear cap 24a.

Further, as the lancet 70a moves forward in the propelling movement, distal spring guide 88a engages the rearward end of retraction spring 94a. The biasing force provided by drive spring 92a is at least in part applied to retraction spring 94a by engagement of distal spring guide 88a with the rearward end of retraction spring 94a which causes the retraction spring 94a to compress toward distal end pocket 98a. The retraction spring 94a is designed such that it may be compressed in whole or in part by the biasing force of drive spring 92a propelling lancet 70a, but still permits puncturing end 74a of lancet 72a to extend through forward opening 60a in shield body 50a a sufficient distance and with sufficient force to puncture the skin of the patient and initiate blood flow. Distal spring guide 88a is sized to provide an abutment surface for abutting against internal sleeve 96a supporting retraction spring 94a to prevent lancet 70a from axial movement entirely out of shield body 50a through forward or front opening 60a.

As indicated previously, retraction spring 94a is typically a compression spring and will have sufficient resilience, to return to a relaxed, unloaded state within shield body 50a after the lancet 70a extends to the puncturing position. Accordingly, once the retraction spring 94a is compressed it will provide a return biasing force on the lancet 70a by engagement with the distal spring guide 88a on carrier body 76a. The retraction spring 94a thereby acts between the forward end wall 58a of the shield body 50a and distal spring guide 88a on carrier body 76a to cause sufficient or complete retraction of the lancet 70a into shield body 50a. In particular, retraction spring 94a applies a return biasing force that retracts the puncturing end 74a of lancet 72a entirely within shield body 50a. Moreover, as the retraction spring 94a returns to a relaxed or unloaded state within shield body 50a, the lancet 70a is returned to a static position within shield body 50a, wherein lancet 70a is disposed at a relatively fixed and stationary position within shield body 50a. Once retraction spring 94a returns to a relaxed or uncompressed state, the retraction spring 94a maintains the lancet 70a disposed within the shield body 50a with puncturing end 74a shielded within shield body 50a, and preventing further movement of lancet 70a to the puncturing position. The lancet device 10a is therefore safely protected from re-use and may be properly discarded, such as in an appropriate medical waste container.

Referring to FIGS. 7-12, a second embodiment of a lancet device 10b is generally illustrated, and comprises the same basic components as lancet device 10a described previously. Generally, lancet device 10b comprises a housing 12b, a shield 14b movably associated with the housing 12b, and a lancet 70b movably disposed in housing 12a and movable through shield 14b. As the foregoing basic components of lancet device 10b are substantially similar to the corresponding components of lancet device 10a, only distinct differences between these components will be discussed herein, along with the use and sequence of operation of lancet device 10b.

In contrast to lancet device 10a, lancet device 10b does not comprise a structure corresponding to shearable element 62a discussed previously. Lancet device 10b comprises the shield 14a having a shield body 50b with a rear ledge or rim 102 at shield proximal end 54b. The rear ledge or rim 102 is adapted for interference engagement with forward rim 42b at the forward end portion 22b of main body 20a of housing 12a. The interference engagement of rear ledge 102 with forward rim 42b is provided to prevent the shield body 50b from axially sliding completely out of housing 12b through front opening 30b defined in forward rim 42b prior to actuating lancet device 10b. Rear rim 102 is sized such that it may contact and slidably engage the inner surface of main body 20b when shield body 50b is retracted (i.e., depressed) into main body 20b, as will occur when the lancet device 10b is actuated by a user.

A further difference over lancet device 10a discussed previously lies in the interfering structure between lancet 70b and shield 14b used to place lancet device 10b into an armed or loaded state, and thereafter cause actuation of lancet device 10b. In lancet device 10b, shield body 50b comprises inward-extending shelves, wings, or internal tabs 104, which take the place of breakable shelves or wings 66a on shearable element 62a in lancet device 10a. The internal tabs 104 are desirably formed integrally with the shield body 50b, but may also be part of an additional, separate structure associated with shield body 62a, for example associated with rear rim 102 and extending into central cavity or bore 56b of shield body 50b. While shield body 50b is shown with two opposing and inward-extending internal tabs 104, it will be appreciated that only one internal tab 104 is necessary for engagement with the lancet 70b in a similar manner to that described previously in connection with the breakable shelves or wings 66a on shearable element 62a.

In lancet device 10a, guide tabs 78a form the structure on lancet 70a for an interference engagement with breakable shelves or wings 66a, which initially just contact shelves 66a under the position effect of drive spring 92a in the initial or pre-actuated state of lancet device 10a. In lancet device 10b, guide tabs 78b are further provided or formed with cutting elements 106 which may be cutting blades, edges, and the like. Cutting elements 106 may be formed integrally with guide tabs 78b or, alternatively, be separate cutting structures secured to guide tabs 78b by means customary in the medical device field, such as direct mechanical or adhesive attachment. The cutting elements 106 are adapted to cut, shear, or plastically deform internal tabs 104 in the internal cavity 56b of shield body 50b during actuation of lancet device 10b to permit movement of lancet 70b through shield body 50b, and thereby conduct a puncturing procedure. Other than the foregoing structural differences, lancet device 10b is substantially similar in all other respects to the structure of lancet device 10a described previously.

With continued reference to FIGS. 7-12, use and operation of lancet device 10b will now be discussed. Prior to use, cover 100b extending distally from carrier body 76b is removed by breaking the frangible connection with carrier body 76b in the manner described previously and withdrawing cover 100b from forward opening 60b in forward end wall 58b of shield body 50b. The forward end wall 58b of shield body 50b may then be placed in contact with a target location on a patient's body. In the initial state of lancet device 10b, the drive spring 92b is substantially uncompressed (i.e., unloaded) and in a relaxed state. Drive spring 92b extends from proximal spring guide 86a of carrier body 76a to rear cap 24b. As discussed previously, in the initial state of lancet device 10b, drive spring 92a is in a relaxed condition and acts on spring guide 86b substantially to position lancet 70b at a stationary position within main body 20b of housing 12a, wherein the lancet 70b occupies a generally fixed position relative to main body 20b. Additionally, drive spring 92b acts on spring guide 86b on carrier body 76b to position carrier body 70a in main body 20b such that guide tabs 78b and more particularly, cutting elements 106 are in interference engagement with tabs or shelves 104 in the internal cavity 56b of shield body 50b. The interference engagement between cutting elements 106 and internal tabs 104 further operates to place shield body 50b at a generally fixed and stationary position relative to main body 20b. Accordingly, until the user is ready to use lancet device 10b, shield body 50b is kept substantially at a generally fixed and stationary position relative to main body 20a by virtue of the interference engagement between guide tabs 78b and internal tabs 104 in shield body 50b.

To use the lancet device 10b, the user grasps opposing sides of housing 12b and exerts downwardly directed force on main body 20. This force causes an opposing force on forward end wall 58b of shield body 50b, causing shield body 50b to retract axially within main body 20b. As shield body 50b retracts into main body 20b, rearward end 54a of shield body 50a moves proximally (i.e., rearward) toward rear cap 24b. Due to the interference engagement between guide tabs 78b and internal tabs or shelves 104 and, more particularly, between cutting elements 106 on guide tabs 78b and internal tabs or shelves 104, lancet 70b also moves rearwardly toward rear cap 24b. As the shield body 50b moves rearward, the opposing force is applied to drive spring 92b through the interference engagement between cutting elements 106 on guide tabs 78a and internal tabs or shelves 104, thereby compressing drive spring 92b between rear cap 24b and carrier body 76b. While internal tabs 104 are intended to cut-through or plastically deformed by cutting elements 106, they are formed with sufficient strength to withstand being cut-through or sheared-off by cutting elements 106 under the opposing force required to axially compress drive spring 92b between proximal spring guide 86b and rear cap 24b. In other words, internal tabs or shelves 104 are formed to withstand the force required to compress drive spring 92b a predetermined distance prior to the desired point of triggering. Further downward movement of housing 12b eventually causes proximal spring guide 86b to contact the inner side of rear cap 24a. At this point, drive spring 92ba substantially reaches its maximum compression with a maximum level of stored potential energy. Lancet device 10b is now in an armed or loaded state sufficient to carry out a puncturing procedure.

Once the proximal spring guide 86b contacts rear cap 24b, the downward force applied to main body 20b of housing 12b is applied entirely to the interference engagement between cutting elements 106 and internal tabs 104. In particular, once proximal spring guide 86b contacts rear cap 24b, the user's entire downward applied force is transmitted from main body 20b (i.e., rear cap 24b) to carrier body 76b and, accordingly, guide tabs 78b and cutting elements 106. The downward cutting force on the internal tabs 104 is now sufficient to cut-through or plastically deform internal tabs 104. At the moment the internal tabs 104 are cut-through or plastically deformed, the opposing force applied to compress drive spring 92b is released, thereby allowing drive spring 92b to move lancet 70b forward in shield 14b. Additionally, with the interference engagement between guide tabs 78b and internal tabs 104 removed, shield body 50b is able to retract further rearward under the downward force still typically applied by the user to housing 12b. The shield body 50b ultimately moves rearward to a position engaging annular rim 36b on rear cap 24b where further rearward movement is halted. As the shield body 50b moves toward annular rim 36b on rear cap 24b, rear rim 102 on the rearward end 54b of shield body 50b rides over top of annular ridge 40b. The annular ridge 40b thereafter forms a locking structure to inhibit or prevent subsequent forward movement of shield 50b.

With the potential energy stored in drive spring 92b by compression thereof released, the drive spring 92b biases lancet 70b away from rear cap 24b and through shield body 50b. During such propelling movement, the corresponding guide tabs 78b and guide channels 80b guide lancet 70b axially through shield body 50b. The biasing force applied to lancet 70a is preferably sufficient to cause the puncturing end 74b of lancet 72b to project a sufficient distance and with sufficient force from the forward opening 60b in shield body 50b to cause a puncture wound at the target location on the patient's body. Moreover, during the propelling movement of lancet 70b, proximal spring guide 86b on carrier body 76b releases from drive spring 92b which remains connected to rear cap 24b. Internal sleeve 96b at the forward end wall 58b defines a distal stop for engaging distal spring guide 88b and prevents lancet 70b from axial movement entirely out of shield body 50b through forward opening 60b.

As the lancet 70b moves forward in the propelling movement, distal spring guide 88b engages retraction spring 94b. The biasing force applied to lancet 70b by drive spring 92b is at least in part applied to retraction spring 94b by engagement of distal spring guide 88b with retraction spring 94b, which causes the retraction spring 94b to compress toward distal end pocket 98b. The retraction spring 94a permits puncturing end 74b of lancet 72b to extend through forward opening 60b in shield body 50b a sufficient distance and with sufficient kinetic energy to puncture the skin of the patient and initiate blood flow, and thereafter return lancet 70b to a substantially fixed and stationary position within shield 14b. In particular, as the retraction spring 94b returns to a relaxed or unloaded state within shield body 50b, the lancet 70a is retracted in shield 14b and returned to a substantially fixed and stationary positioned within shield body 14b. Thereafter, the engagement of retraction spring 94b with distal spring guide 88b maintains the lancet 70b at a generally fixed and stationary position within shield body 50b. This maintains puncturing end 74b shielded within shield body 50b, and prevents further movement of lancet 70b to the puncturing position.

Referring to FIGS. 13-18, a third embodiment of a lancet device 10c is generally illustrated, and comprises the same basic components as lancet devices 10a, 10b described previously. Generally, lancet device 10c comprises a housing 12c, a shield 14c movably associated with the housing 12c, and a lancet 70c movably disposed in housing 12c. As the foregoing basic components of lancet device 10c are substantially similar to the corresponding components of lancet devices 10a, 10b only distinct differences between these components will be discussed herein, along with the general use and sequence of operation of lancet device 10c.

In lancet devices 10a, 10b, lancets 70a, 70b are initially positioned at substantially fixed and stationary positions in housings 12a, 12b by drive springs 92a, 92b in the initial, pre-actuated states of these devices. In lancet devices 10a, 10b, drive springs 92a, 92b are initially in a relaxed, unloaded condition and act upon lancets 70a, 70b to position lancets 70a, 70b relative to housings 12a, 12b. Lancet devices 10a, 10b are only placed in an armed or loaded state when shields 14a, 14b are retracted (i.e., depressed) into housings 12a, 12b under the force applied by a user, which in turn causes lancets 70a, 70b to act upon drive springs 92a, 92b and compress and load the respective drive springs 92a, 92b with potential energy.

Lancet device 10c is initially provided in an armed or loaded state, with lancet 70c ready to be biased to a puncturing position by a compressed drive spring 92c. In this initial armed state, drive spring 92c is in a compressed (i.e., loaded) state, ready to bias the lancet 70c through a puncturing procedure upon release. In particular, lancet device 10c is provided with drive spring 92c compressed between proximal spring guide 86c on carrier body 76c and rear cap 24c. The lancet 70c is secured against forward movement into shield 14c by a locking or actuation structure 110 extending between housing 12c and lancet 70c. Actuator 110 prevents release of lancet 70c and, correspondingly, maintains compression of drive spring 92c until a user of the lancet device 10c is ready to carry out a puncturing procedure.

Actuator 110 generally comprises a sleeve portion 112 and one or more pivotal splints or tabs 114, for example elastic splints, extending from the sleeve portion 112. Sleeve portion 112 is disposed in an annular wall recess 116 defined in the inner surface of main body 20c of housing 12c. Main body 20c is formed with a generally thicker annular wall in lancet device 10c in comparison to lancet devices 10a, 10b. Sleeve portion 112 may be secured in wall recess 116 by a medical grade adhesive and/or preferably by being captured axially between wall recess 116 and annular rim 36c on rear cap 24c and thereby frictionally held in wall recess 116. Actuator 110 is depicted with two generally inward-extending splints or tabs 114 engaging lancet 70c. While this configuration is desirable, only one elastic splint 114 for engaging lancet 70c is typically required, and additional splints 114 in excess of two may be also be provided.

The splints 114 extend generally rearward or in a proximal direction in main body 20c and engage guide tabs 78c on carrier body 76c of lancet 70c. Splints 114 are angled inward, in this instance, at approximately a 45° angle relative to Central Axis A to engage guide tabs 76c in the initial state of lancet device 10c. In particular, ends 118 of splints 114 engage guide tabs 78c on carrier body 76c to prevent lancet 70c from releasing from the initial, armed state of lancet device 10c and thereby maintain drive spring 92c in a compressed state until lancet device 10c is actuated by a user. Splints 114 are each connected by a hinge connection 120 to sleeve portion 112. The hinge connection 120 may be a living hinge as illustrated as an exemplary embodiment of this structure. Ends 118 of splints 114 engage a corner of guide tabs 78c, such that distal movement of carrier body 76c distally with respect to housing 12c in absence of shield 14c would cause splints 114 to generally compress between hinge connection 120 and the point of contact between guide tabs 78c. As with lancet devices 10a, 10b, lancet device 10c is actuated when a user depresses housing 12c to retract (i.e., depress) shield 14c therein. However, shield 14c is now adapted to release actuator 110 between housing 12c and lancet 70c, thereby releasing compressed drive spring 92c to bias the lancet 70c through a puncturing procedure.

To facilitate actuation of lancet device 10c, shield 14c is adapted to engage and release actuator 110. For this purpose, shield body 50c may be formed with a tapered rear rim 122 at shield proximal end 54c. The tapered rear rim 120 is generally tapered in the same direction as splints 114 to engage the distal or forward facing sides of splints 114. The point of engagement for the tapered rear rim 122 is on splints 114 at a location between hinge connection 120 and the point of contact between guide tabs 78c. The tapered rear rim 122 may define a taper of about 45° to correspond to the inward taper of splints 114. In the initial, armed state of lancet device 10c, the tapered rear rim 122 is (in contact with splints 114 so that any rearward movement of shield 14c into housing 12a will immediately act upon the actuator 110 and splints 114 in particular. While the rear rim 122 is illustrated with a defined taper, it will be appreciated that such taper may be omitted and shield body 50c formed as a cylindrical structure with a flat or blunted rear rim 122.

With continued reference to FIGS. 13-18, use and operation of lancet device 10c will now be discussed. As with previous embodiments, cover 100c extending distally from carrier body 76c is first removed by breaking the frangible connection with carrier body 76c and withdrawing cover 100c from forward opening 60c in forward end wall 58c of shield body 50c. The forward end wall 58c of shield body 50c may then be placed in contact with the target location on the patient's body. As indicated, lancet device 10c is initially provided in an armed state with lancet 70c ready to initiate a puncturing procedure when compressed drive spring 92c is released.

To carry out a puncturing procedure, the user grasps opposing sides of housing 12c and exerts downwardly directed force in the direction of Arrow X on main body 20c forcing shield body 50c to retract into main body 20c. This force causes an opposing force on forward end wall 58c of shield body 50c, causing shield body 50c to retract axially within main body 20c. As shield body 50c retracts into main body 20c, tapered rear rim 122 on rearward end 54c of shield body 50c and in engagement with splints 114 begins to move splints 114 radially outward toward sleeve portion 112. Continued rearward movement of shield body 50c causes the splints 114 to continue their radial outward movement away from lancet 70c until the splints 114 disengage from guide tabs 78c and release the interference engagement therewith. The configuration of actuator 110 converts the axial movement of shield body 50c into pivotal radial outward movement of splints 114 to effectuate actuation of lancet device 10c.

With the potential energy in drive spring 92c released, drive spring 92c biases the lancet 70c away from rear cap 24c and through shield body 5cb. During such propelling movement, corresponding guide tabs 78c on carrier body 76c and guide channels 80c within shield body 50c guide lancet 70c axially through shield body 50c. The biasing force imparted to lancet 70c is preferably sufficient to cause the puncturing end 74c of lancet 72c to project a sufficient distance and with sufficient force from the forward opening 60c of shield body 50c to cause a puncture wound in the desired location on the patient's body. Moreover, during the propelling movement of lancet 70c, proximal spring guide 86c on carrier body 76c releases from drive spring 92c which remains connected to rear cap 24c. Distal spring guide 88c provides an abutment surface for engaging internal sleeve 96c supporting retraction spring 94c to prevent lancet 70c from axial movement entirely out of shield body 50c through forward opening 60c.

As the lancet 70c moves forward in the propelling movement, distal spring guide 88c engages retraction spring 94c. The biasing/propelling force provided by drive spring 92c is at least in part applied to retraction spring 94c by engagement of distal spring guide 88c with retraction spring 94c, which causes the retraction spring 94c to compress toward distal end pocket 98c. The retraction spring 94c permits puncturing end 74c of lancet 72c to extend through forward opening 60c in shield body 50c a sufficient distance and with sufficient force to puncture the skin of the patient and initiate blood flow, and thereafter return lancet 70c to a substantially fixed and stationary position within shield 14b. In particular, as the retraction spring 94c returns to a relaxed or unloaded state within shield body 50c, the lancet 70c is retracted in shield 14c and returned to a generally stationary and fixed position within shield body 50c. Thereafter, the engagement of retraction spring 94c with distal spring guide 88c maintains the lancet 70c at a stationary and relatively fixed position within shield body 50c and maintains puncturing end 74c shielded within shield body 50c preventing further movement of lancet 70c to the puncturing position.

Referring to FIGS. 19-23, a fourth embodiment of a lancet device 10d is generally illustrated, and generally comprises a housing 12d and a lancet 70d disposed in housing 12d. Lancet device 10d differs from lancet devices 10a-c discussed previously, as lancet device 10d is not actuated through the retraction (i.e., depression) of a shield element into housing 12d. However, lancet device 10d is similar to lancet device 10c discussed immediately above because lancet device 10d is initially provided in an armed or loaded state, with lancet 70d ready to be biased to the puncturing position by drive spring 92d upon release of an interfering structure. In this initial, armed state, drive spring 92d is in a compressed (i.e., loaded) state, ready to bias the lancet 70d through a puncturing procedure upon repositioning lancet 70d with respect to an interfering structure or engagement between housing 12d and lancet 70d. However, the configuration of the housing 12d, lancet 70d, and drive spring 92d differ from previous embodiments and these differences will now be described.

Housing 12d of lancet device 10d comprises an elongated main body 20d that generally defines a cylindrical and hollow configuration. The main body 20d has a distal or forward end portion 22d, and a rear cap 24d forming a proximal or rearward end portion 26d of the main body 20d. The interior of housing 12d is generally open and comprises an internal cavity 28d. The internal cavity 28d is closed at the rearward end due to rear cap 24d, and includes a front opening 30d defined in forward end portion 22d of main body 20d, and through which lancet 70d at least partially extends when lancet device 10d is actuated. Main body 20d and rear cap 24d may be integrally formed. Typically, main body 20d and rear cap 24d are separate elements that are affixed together to form housing 12d, as illustrated, which facilitates assembly of lancet device 10d. As examples, main body 20d and rear cap 24d may be affixed together through an appropriate medical grade adhesive, and/or may be connected using inter-engaging structures providing a mechanical engagement therebetween, such as a friction-fit or a snap-fit construction. For example, main body 20d may include an annular rim 32d defining an annular groove 34d, and the rear cap 24a may include a mating annular rim 36d having a mating annular lip 38d as mating elements in much the same manner as described previously.

In contrast to previous embodiments, distal or forward end portion 22d of main body 20d comprises an axially rearward-extending internal sleeve 98d that defines a distal end pocket 98d for receiving and supporting retraction spring 94d. In previous embodiments, the retraction spring(s) were disposed in a distal end pocket formed as part of the forward end wall of the actuating shield structure. This structure is now provided at the forward end portion 22d of main body 20d of housing 12d. Additionally, main body 20d of housing 12d further comprises an actuation structure or actuator 130 for causing actuation of lancet 70d and corresponding release of drive spring 92d. Actuator 130 generally comprises an actuating button or lever 132 that is typically pivotally associated with main body 20d. The pivotal association with main body 20d may be in the form of a living hinge or equivalent structure and lever 132 may thus be integrally formed with main body 20d. A tab member 134 depends from an inner side of actuating lever 132 for engaging lancet 70d and causing actuation of the same. In particular, lever 132 is pivotally connected to main body 20d so that the lever 132 may be depressed inward into internal cavity 28d in main body 20d, such that tab member 134 interacts with lancet 70d to cause actuation or release of lancet 70d.

Main body 20d of housing 12d includes opposing inner sidewalls 136 each defining an internal guide channel 138 for guiding movement of lancet 70d within main body 20d. Guide channels 138 may be formed as grooves or recesses in the inner sidewalls 136, or be formed in a structure extending inward from the respective sidewalls 136. Guide channels 138 are generally L-shaped and comprise a longitudinally extending main channel 140 and a generally transversely extending side channel 142. Main channel 140 extends distally forward from an area proximate to tab member 134 to a location proximate to retraction spring 94d. Main channel 140 defines an abutment surface or stop 144 in guide channels 138 to provide a stop for carrier body 76d of lancet 70d to prevent axial movement of the lancet 70d entirely out of main body 20d through front opening 30d.

Side channel 142 is contiguous with main channel 140 and extends approximately oblique to transverse to main channel 140. Side channel 142 extends upward in a direction towards lever 132. While side channel 142 is formed generally oblique to main channel 140, side channel 142 and main channel 140 define a tapered corner or vertex 146 at their intersection. The corner 146 defines an angle of less than about 90°. The opposing side channels 142 in main body 20d are used to initially receive guide tabs 78d on carrier body 76d for maintaining carrier body 76d in a dynamically stable and balanced position, thereby opposing the force acting on guide tabs 78d by drive spring 92d, and restraining compressed drive spring 92d. Corner 146 is used to define the transition between main channel 140 and side channel 142. Movement of guide tabs 78d towards side channels 142 allows carrier body 76d to transition from a position of dynamic stability to a position of dynamic instability. Accordingly, side channels 142 initially maintain the positioning of guide tabs 78d, with guide tabs 78d in interference engagement with corners or vertexes 146 to maintain the positioning of guide tabs 78d until lancet device 10d is to be actuated.

Lancet 70d is formed in a generally analogous manner as previous embodiments and comprises a lancet 72d with a puncturing end 74d at the forward end thereof, and a carrier body 76d supporting lancet 72d at the rearward end thereof. The carrier body 76d comprises a pair of guide tabs 78d on an external surface thereof that engage guide channels 138. Lancet 70d is adapted for axial movement through the internal cavity 28d of main body 20d between an initial position wherein guide tabs 78d are disposed in side channels 142 and the puncturing end 74a is disposed entirely within main body 20d, to a puncturing position wherein the puncturing end 74d extends beyond the front opening 30d in main body 20d a sufficient distance to cause a puncture wound on a patient's body while guide tabs 78d remain disposed in main channels 140. Further details regarding the operation of lancet device 10d and the movement of lancet 70d are provided hereinafter.

Carrier body 76d further comprises a proximal or rear rim 148 at the rearward end thereof. Rim 148 defines the forward end of proximal spring guide 86d and typically has a diameter larger than the diameter of distal spring guide 88d of carrier body 76d. Rim 148 is provided as a contact structure or surface on lancet 70d for engagement by tab member 134 to cause actuation of lancet device 10d. The diameter of rim 148 is also typically sized to be at least equal to the diameter of drive spring 92*d* and provides a contact structure or surface that restrains compressed drive spring 92*d* in the initial state of lancet 70*d*. During actuation of lancet device 10*d*, drive spring 92*d* acts against rear rim 148 to bias lancet 70*d* to the puncturing position, as described herein. Moreover, carrier body 76*d* additionally comprises two opposing posts 150 cooperating with guide channels 138, and main channels 140 in particular. Posts 150 engaged in guide channels 138 permit at least a limited amount of pivotal movement by carrier body 76*d* about an axis passing through posts 150, and maintain lancet 70*d* associated with guide channels 138 until guide tabs 78*d* align with main channels 140 during the actuation sequence of lancet device 10*d*.

In the initial state of lancet device 10*d*, drive spring 92*d* is at least partially compressed between rear rim 148 on carrier body 76*d* and rear cap 24*d*, and typically has sufficient stored potential energy to conduct a skin-puncturing procedure. The rearward or proximal end of drive spring 92*d* is typically secured to rear cap 24*d* in the manner discussed previously in this disclosure. The forward or distal end of drive spring 92*d* is associated with carrier body 76*d* and may be secured to rear rim 148 by similar means discussed previously, as by suitable adhesive or direct mechanical attachment. Drive spring 92*d* generally defines an off-axis or off-center spring arrangement, wherein drive spring 92*d* extends at upward angle toward lever 132. Drive spring 92*d* is stabilized in the off-center and compressed (i.e., loaded) arrangement by engagement of guide tabs 78*d* in side channels 142 of guide channels 138. Corners 146 define an interfering engagement and point of transition for guide tabs 78*d* to maintain drive spring 92*d* in a compressed (i.e., loaded) state and in the off-center configuration. The acute angle defined by corner 146 defines a receiving notch 152 for guide tabs 78*d* to prevent guide tabs 78*d* from readily releasing from side channels 142 until intended actuation by a user. Thus, engagement of guide tabs 78*d* in guide channels 138 forms an interfering structure to secure lancet 70*d* against forward movement in main body 20*d* and, correspondingly, maintains compression of drive spring 92*d* until a user of the lancet device 10*d* is ready to carry out a puncturing operation.

With continued reference to FIGS. 19-23, use and operation of lancet device 10*d* will now be discussed. As with previous embodiments, a cover (not shown) extending distally from carrier body 76*d* may be provided with carrier body 76*d*. As with previous embodiments, such a cover is removed by breaking the frangible connection with carrier body 76*d* and withdrawing the cover from front opening 30*d* in main body 20*d*. The forward end rim 42*d* of main body 20*d* may then be placed in contact with the target location on a patient's body. As indicated previously, lancet device 10*d* is initially provided in an armed state with lancet 70*d* ready initiate a puncturing procedure when compressed drive spring 92*d* is released.

To carry out a puncturing procedure, the user grasps opposing sides of housing 12*d* and exerts downwardly directed force on lever 132 pivotally connected to main body 20*d*, causing lever 132 to depress into internal cavity 28*d* of main body 20*d*. As lever 132 is depressed into main body 20*d*, tab member 134 interacts with rear rim 148 on carrier body 76*d*. In particular, the downward force applied to lever 132 causes tab member 134 to move rear rim 148 downward in the internal cavity 28*d*. As rear rim 148 of carrier body 76*d* moves downward in internal cavity 28*d* of main body 20*d*, the carrier body 76*d* will substantially simultaneously pivot about posts 150 in main channel 140 of guide channels 138. Also substantially simultaneously, guide tabs 78*d* received in side channels 142 slide downward in side channels 142 until passing corners 146 which has the effect of moving carrier body 76*d* from a first state of being dynamically balanced to a second state of being dynamically unbalanced, thereby allowing drive spring 92*d* to propel carrier body 76*d* through main body 20*d* until the puncturing end 74*d* of lancet 72*d* projects through front opening 30*d* in main body 20*d*. The downward movement of guide tabs 78*d* in side channels 142 has the optional effect of further compressing drive spring 92*d*.

As the lever 132 is continued to be depressed into main body 20*d*, guide tabs 78*d* eventually clear corners 146 and disengage from side channels 142. At this point, guide tabs 78*d* align with main channel 140 of guide channels 138 and are free to move forward therein under the biasing force of drive spring 92*d*. Correspondingly, with the engagement between guide tabs 78*d* and corners 146 released, the drive spring 92*d* is free to bias lancet 70*d* to the puncturing position. With the stored potential energy in drive spring 92*d* released, drive spring 92*d* thereafter biases the lancet 70*d* away from rear cap 24*d* and through main body 20*d*. During such propelling movement, the engagement of guide tabs 78*d* in guide channels 138 guides lancet 70*d* axially through main body 20*d*. The distal biasing energy imparted to lancet 70*d* is preferably sufficient to cause the puncturing end 74*d* of lancet 72*d* to project a sufficient distance and with sufficient force from the front opening 30*d* in main body 20*d* to cause a puncture wound in the desired location on the patient's body. Moreover, during the propelling movement of lancet 70*d*, proximal spring guide 86*d* on carrier body 76*d* releases from drive spring 92*d* which remains connected to rear cap 24*d*. The engagement of posts 150 with stops 144 in guide channels 138 prevents lancet 70*d* from axial movement entirely out of main body 20*d* through front opening 30*d*.

As the lancet 70*d* moves forward in the propelling movement, distal spring guide 88*d* engages retraction spring 94*d*. The biasing force of drive spring 92*d* is at least in part applied to retraction spring 94*d* by engagement of distal spring guide 88*d* with retraction spring 94*d*, which causes the retraction spring 94*d* to compress toward distal end pocket 98*d*. The retraction spring 94*d* permits puncturing end 74*d* of lancet 72*d* to extend through front opening 30*d* in main body 20*d* a sufficient distance and with sufficient force to puncture the skin of the patient and initiate blood flow, and thereafter return lancet 70*d* to a generally fixed and stationary position within housing 12*d*. In particular, as the retraction spring 94*d* returns to a relaxed or unloaded state within main body 20*d*, the lancet 70*d* is retracted in main body 20*d* and returned to a generally fixed and stationary position within main body 20*d*. Thereafter, the engagement of retraction spring 94*d* with distal spring guide 88*d* maintains the positioning of lancet 70*d* within main body 20*d* with puncturing end 74*d* of lancet 72*d* shielded within housing 12*d*, and prevents further movement of lancet 70*d* to the puncturing position.

Referring to FIGS. 24-30, a fifth embodiment of a lancet device 10*e* is generally illustrated, and comprises the same basic components or elements as lancet devices 10*a-c* described previously. Generally, lancet device 10*e* comprises a housing 12*e*, a shield 14*e* movably associated with the housing 12*e*, and a lancet 70*e* movably disposed in housing 12*e*. As the basic components of lancet device 10*e* are substantially similar to the corresponding components of lancet devices 10*a-c* discussed previously, only distinct differences between these general components will be discussed herein, along with the use and sequence of operation of lancet device 10e.

The sequence of operation of lancet device 10e generally follows the sequence of operation of lancet devices 10a-c, wherein lancet device 10e is armed and actuated through the retraction (i.e., depression) of shield 14e into housing 12e. Generally, in lancet device 10e, arming and actuation of lancet device 10e occurs as a result of proximal or rearward end 54e of shield body 50e of shield 14e engaging a structure within housing 12e that causes compression (i.e., loading) of drive spring 92e and, upon release of such compression, drive spring 92e biases lancet 70e through a propelling movement resulting in puncturing end 74e of lancet 72e projecting from shield 14e for puncturing procedure the skin of a patient, as discussed in more detail herein.

In lancet device 10e, shield 14e comprises a shield body 50e with a rear ledge or rim 162 at shield proximal end 54e. The rear ledge or rim 162 is generally adapted for contact or engagement with a slide plate 164 disposed in housing 12e to cause actuation of lancet device 10e as described in detail herein. Slide plate 164 forms the structure for compressing drive spring 92e alluded to previously. Rear ledge or rim 162 is also adapted to engage forward rim 42e of main body 20e of housing 12e to prevent shield body 50e from axially sliding completely out of housing 12e through front opening 30e defined in the forward end wall 58e of shield body 50e. Rear rim 162 is sized such that it may slide along the inner surface of main body 20b when shield body 50e is retracted (i.e., depressed) into main body 20e, as will occur when the lancet device 10b is actuated by a user.

Slide plate 164 forms the internal structure in main body 20e of housing 12e which is used to cause compression of drive spring 92e thereby storing potential energy in drive spring 92e which, upon release, is used to bias lancet 70e to the puncturing position. Slide plate 164 is disposed in main body 20e of housing 12e to be in contact with rear rim 162 of shield body 50e. Slide plate 164 is associated with rear rim 162 of shield body 50e so that slide plate 164 may move rearward with shield body 50e as shield body 50e is retracted (i.e., depressed) into main body 20e of housing 12e to arm and actuate lancet device 10e. Slide plate 164 defines a generally centrally-located keyhole or key opening 166 that is sized and shaped to generally conform to the transverse cross-sectional shape of carrier body 76e of lancet 70e, to allow the cross-section of carrier body 76e to pass therethrough during actuation of lancet device 10e. In particular, keyhole 166 comprises a central, typically circular-shaped portion 168 and two contiguous laterally-extending notches 170, which define a shape that permits the transverse cross-section of carrier body 76e to pass therethrough during actuation of lancet device 10e, as discussed further herein.

A further difference in lancet device 10e when compared to lancet devices 10a-c discussed previously lies in the formation of rear cap 24e, and the interaction therewith by slide plate 164 and shield body 50e to cause arming and actuation of lancet device 10e. As in previous embodiments, rear cap 24e comprises an annular rim 36e that engages an annular rear rim 32e of main body 20e of housing 12e. In particular, annular lip 38e on annular rim 36e engages annular groove 34e defined in annular rim 32e to join rear cap 24e to main body 20e. However, in lancet device 10e, annular rim 36e is elongated and extends distally a greater distance into main body 20e of housing 12e, so as to be positioned proximate to the rear rim 162 of shield body 50e in the initial state of lancet device 10e. Annular rim 36e defines a tapered internal cam surface 172, which is shaped to impart a specific cam motion to slide plate 164 due to contact therewith and ultimately cause arming and actuation of lancet device 10e as described hereinafter.

In the initial state of lancet device 10e, drive spring 92e is associated with lancet 70e, with the drive spring 92e extending from the inner side of rear cap 24e to carrier body 76e. In lancet device 10e, carrier body 76e is further formed with a proximal or rear rim 174 at the rearward end thereof. Rim 174 generally defines the forward end of proximal spring guide 86e and typically has a diameter larger than the diameter of distal spring guide 88e and typically at least equal to the diameter of the forward end of drive spring 92e. Rim 174 defines a contact structure or surface on carrier body 76e that is used to compress drive spring 92e to place the lancet device 10e into a loaded or armed state. Once the drive spring 92e is released, thereby releasing the potential energy stored therein during the compression of drive spring 92e, the drive spring 92e will act against rear rim 174 to bias lancet 70e to the puncturing position. Guide tabs 78e are typically formed integrally with rear rim 174 and extend laterally therefrom.

With the various distinguishing components of lancet device 10e now set forth, use and operation of lancet device 10e will now be described with continued reference to FIGS. 24-30. Prior to use, cover 100e extending distally from carrier body 76e is removed by breaking the frangible connection with carrier body 76e, and withdrawing cover 100e from forward opening 60e in forward end wall 58e of shield body 50e in the manner described previously. The forward end wall 58e of shield body 50e may then be placed in contact with a target location on a patient's body. In the initial, unarmed state of lancet device 10e, the drive spring 92e is substantially uncompressed (i.e., unloaded) and extends from rear rim 174 on carrier body 76e to rear cap 24e. In the initial, unarmed state of lancet device 10e, drive spring 92e is in a relaxed condition and acts on rear rim 174 on carrier body 76e to position lancet 70e at a generally fixed and stationary position within main body 20e of housing 12e, wherein the lancet 70e occupies a substantially fixed position relative to main body 20e and shield body 50e. Additionally, the drive spring 92e acting on rear rim 174 causes the carrier body 76e to engage (i.e., contact) the rear side of slide plate 164. In particular, drive spring 92e in its relaxed or unloaded initial state, causes the front side or surface of rear rim 174 and front surface 82e of guide tabs 78e to be in substantial contact with the rear side or surface of slide plate 164. Moreover, in the initial state of lancet device 10e, slide plate 164 is positioned in contact with the rear rim 162 of shield body 50e so that rear rim 174 and guide tabs 78e of carrier body 76e are offset vertically from the keyhole 166 defined in slide plate 164. Accordingly, in the initial state of lancet device 10e, rear rim 174 and guide tabs 78e are in interference engagement with the rear side of slide plate 164.

To use the lancet device 10e, the user grasps opposing sides of housing 12e and exerts downwardly directed force on main body 20e thereof in the direction of Arrow X. This force causes an opposing force on forward end wall 58e of shield body 50e, causing shield body 50e to retract (i.e., depress) axially within main body 20e. As shield body 50e retracts into main body 20e, rearward end 54e of shield body 50e moves proximally (i.e., rearward) toward rear cap 24e. In particular, rear rim 162 at the rearward end 54e of shield body 50e moves rearward while simultaneously interacting with cam surface 172. Further, as rear rim 162 of shield body 50e moves rearwardly in main body 20e, slide plate 164 also begins to move rearwardly in combination with the rear rim 162 toward rear cap 24e, due to the engagement between slide plate 164 and rear rim 162. Additionally, lancet 70e will move rearward with shield body 50e and slide plate 164 due to the offset interference engagement between rear rim 174 and guide tabs 78e and slide plate 164. The rearward movement of lancet 70e will further begin to compress drive spring 92e, due to the engagement of drive spring 92e with the rear side of rear rim 174 on carrier body 76e.

The downward movement imparted to housing 12e also causes the slide plate 164 to interact with tapered cam surface 172 defined by annular rim 36e of rear cap 24e. Due to the tapered shape of cam surface 172 from the forward or distal end of annular rim 36e toward the Central Axis A of lancet device 10e, slide plate 164 moves downward in internal cavity 28e of main body 20e as the slide plate 164 is retracted in main body 20e. Accordingly, as shield body 50e is retracted (i.e., depressed) into main body 20e of housing 12e, slide plate 164 moves rearwardly and downward in main body 20e, and this combined movement occurs substantially simultaneously. Additionally, continued rearward movement of shield body 50e has the effect of compressing the drive spring 92e and storing the potential energy necessary to bias the lancet 70e to the puncturing position.

Once the slide plate 164 moves downward to a position where the transverse cross-sectional shape of the carrier body 76e defined at the location of rear rim 174 and guide tabs 78e on carrier body 76e matches the corresponding profile of keyhole 166, the interfering engagement restraining the drive spring 92e is removed and the potential energy stored in drive spring 92e is released. With the stored potential in drive spring 92e released and providing a biasing force acting on lancet 70e, the drive spring 92e biases the lancet 70e away from rear cap 24b and through shield body 50e. During such propelling movement, the corresponding guide tabs 78e and guide channels 80b guide lancet 70b axially through shield body 50e. The biasing force acting on lancet 70e is preferably sufficient to cause the puncturing end 74e of lancet 72e to project a sufficient distance and with sufficient force from the forward opening 60e in shield body 50e to cause a puncture wound at the target location on the patient's body. Moreover, during the propelling movement of lancet 70e, proximal spring guide 86e on carrier body 76e releases from drive spring 92e which remains connected to rear cap 24e.

As the lancet 70e moves forward in the propelling movement, distal spring guide 88e engages retraction spring 94e. The biasing/propelling force provided by drive spring 92e is at least in part applied to retraction spring 94e by engagement of distal spring guide 88e with retraction spring 94e, which causes the retraction spring 94e to compress toward distal end pocket 98e. The retraction spring 94e permits puncturing end 74e of lancet 72e to extend through forward opening 60e in shield body 50e a sufficient distance and with sufficient force to puncture the skin of the patient and initiate blood flow, and thereafter returns lancet 70e to a substantially fixed and stationary position within shield 14e. Distal spring guide 88e provides an abutment surface for engaging internal sleeve 96e in shield body 50e supporting retraction spring 94e to prevent lancet 70e from axial movement entirely out of shield body 50e through forward opening 60e. As the retraction spring 94e returns to a relaxed or unloaded state within shield body 50e, the lancet 70e is retracted in shield 14e and returned to a substantially fixed and stationary positioned within shield body 14e. Thereafter, the engagement of retraction spring 94e with distal spring guide 88e maintains the lancet 70e at a generally fixed position within shield body 50e. This engagement further maintains puncturing end 74e shielded within shield body 50e, and prevents further movement of lancet 70e to the puncturing position.

Referring to FIGS. 31-37, a sixth embodiment of a lancet device 10f is generally illustrated, and generally comprises a housing 12f and a lancet 70f disposed in housing 12f. Lancet device 10f is similar in structure to lancet device 10d discussed previously but includes a plate for actuating the device in a similar manner to lancet device 10e discussed immediately above. As with lancet device 10d, lancet device 10f is not actuated through the retraction (i.e., depression) of a shield element into housing 12f, and is initially provided in an armed or loaded state, with lancet 70f ready to be biased to the puncturing position by drive spring 92f upon release of an interfering structure. The interfering structure in lancet device 10f is a plate similar that described previously and additional details of which specific to the present embodiment will be provided herein.

In the initial, armed state of lancet device 10f, drive spring 92f is in a compressed (i.e., loaded) state, ready to bias the lancet 70f through a puncturing procedure upon release. As the configuration of the housing 12f, lancet 70f, and drive spring 92f are generally similar to lancet device 10d discussed previously, the following discussion will build upon the previously discussed structure of lancet device 10d.

Housing 12f of lancet device 10f comprises an elongated main body 20f that generally defines a cylindrical and hollow configuration. The main body 20f has a distal or forward end portion 22f, and a rear cap 24f forming a proximal or rearward end portion 26f of the main body 20f. The interior of housing 12f is generally open and comprises an internal cavity 28f. The internal cavity 28f is closed at the rearward end due to rear cap 24f, and includes a front opening 30f defined in forward end portion 22f of main body 20f, and through which lancet 70f extends when lancet device 10f is actuated. Main body 20f and rear cap 24f may be integrally formed. Typically, main body 20f and rear cap 24f are separate elements that are affixed together to form housing 12f, in the manner described previously, but may also be integral also in the manner described.

In lancet device 10f, distal or forward end portion 22f of main body 20d comprises an axially rearward-extending internal sleeve 96f which defines a distal end pocket 98f for receiving and supporting retraction spring 94f. Forward rim 42f at the forward end portion 22f of main body 20f is adapted to be placed in contact with a patient's body during use of lancet device 10f. Additionally, main body 20f comprises an actuation structure or actuator 180 for causing actuation of lancet 70f and corresponding release of compressed drive spring 92f. Actuator 180 generally comprises an actuating button or lever 182 that is pivotally associated with main body 20f. The pivotal association with main body 20f may be in the form of a living hinge 183 or equivalent structure and lever 182 may thus be integrally formed with main body 20f. Actuator 180 further comprises a plate member 184, which depends from an inner side of actuating lever 182 and extends downward into internal cavity 28f of main body 20f of housing 12f. Plate member 184 is oriented substantially transverse to the Central Axis A of main body 20f in the initial state of actuating lever 182. Plate member 184 may be formed integrally with lever 182 or be provided as a separate component from lever 182 and be joined thereto. For example, lever 182 may define a recess 186 that accepts a tab 188 extending from plate member 184 to connect plate member 184 to lever 182. Tab 188 may be secured in recess 186 via friction fit and/or with an adhesive. The pivotal connection be lever 182 and main body 20f is provided so that plate member 184 may interact with lancet 70*f* and, further, drive spring 92*f* to release the compressed drive spring 92*f* and cause actuation of lancet device 10*f*.

Main body 20*f* of housing 12*f* comprises opposing inner sidewalls 190 each defining an internal guide channel 192 for guiding movement of lancet 70*f* within main body 20*f*. Guide channels 192 may be formed as longitudinally extending grooves or recesses in the inner sidewalls 190, or may be formed as part of a raised structure extending inward from sidewalls 190. The guide channels 192 are adapted to receive to receive guide tabs 78*f* on carrier body 76*f* to guide movement of lancet 70*f* within main body 20*f*. Guide channels 190 each define an end surface or stop 194, which may be use to provide a stop for guide tabs 78*f* to prevent lancet 70*f* from axial movement entirely out of main body 20*f* through front opening 30*f* after the lancet device 10*f* is actuated. However, desirably distal spring guide 88*f* may be formed to provide an abutment surface for engaging internal sleeve 96*f* in shield body 50*f* supporting retraction spring 94*f* to prevent lancet 70*f* from axial movement entirely out of shield body 50*f* through forward opening 60*f*.

Lancet 70*f* is formed in a generally analogous manner to lancet 70*d* of lancet device 10*d* discussed previously, with carrier body 76*f* including two outward extending guides tabs 76*f* and supporting a lancet 72*f* with a puncturing end 74*f* at the forward end thereof. As in previous embodiments, guide tabs 78*f* extending laterally outward from carrier body 76*f* engage guide channels 190 in main body 20*f*. Carrier body 76*f* further comprises a proximal or rear rim 196 at the rearward end thereof. Rim 196 generally defines the forward end of proximal spring guide 86*f* and typically has a diameter larger than the diameter of distal spring guide 88*f* on carrier body 76*f*, and typically at least equal to the diameter of the forward end of drive spring 92*f*. Rim 196 is provided as a contact structure or surface on lancet 70*f* for interference engagement with plate member 184 to prevent actuation of lancet device 10*f*, and maintain compression of drive spring 92*f* in the initial, pre-actuated state of lancet device 10*f*. As indicated, the diameter of rim 196 is also typically sized to be at least equal to the diameter of drive spring 92*f* and provides a contact structure or surface that maintains drive spring 92*f* in a compressed state in the initial, pre-actuated state of lancet device 10*f*. During actuation of lancet device 10*f*, drive spring 92*f* will act against rim 196 to bias lancet 70*f* to the puncturing position, as described further herein. In general, lancet 70*f* is adapted for axial movement through the internal cavity 28*f* of main body 20*f* between an initial position wherein plate member 184 is in interference engagement with the lancet 70*f*, thereby holding or maintaining drive spring 92*f* in a compressed or loaded state, to a puncturing position where the puncturing end 74*f* of lancet 72*f* extends beyond the front opening 30*f* in main body 20*f* a sufficient amount to cause a puncture wound on a patient's body.

Plate member 184 defines a generally centrally-located keyhole or key opening 197 that is sized and shaped to match the transverse cross-sectional shape or outline of carrier body 76*f* of lancet 70*f* to allow the carrier body 76*f* to pass therethrough during actuation of lancet device 10*f*. In particular, keyhole 197 comprises a central, typically circular-shaped portion 198 and two contiguous laterally extending notches 200 which define a shape that permits the carrier body 76*f* to pass therethrough during actuation of lancet device 10*f*.

With the general components of lancet device 10*f* now set forth, use and operation of lancet device 10*f* will now be described with continued reference to FIGS. 31-37. Prior to use, cover 100*f* extending distally from carrier body 76*f* is removed by breaking the frangible connection with carrier body 76*f*, and withdrawing cover 100*f* from the front opening 30*f* in main body 20*f* in the manner described previously. In the initial, pre-actuated state of lancet device 10*f*, plate member 184 is positioned relative to carrier body 76*f* such that the rear rim 196 and guide tabs 78*f* on carrier body 76*f* are offset from keyhole 197 and, therefore, in interference engagement with the rear side of plate member 184. In particular, the transverse cross-sectional shape defined by the carrier body 76*f* at the location of rear rim 196 and guide tabs 78*f* is offset, typically vertically offset, from keyhole 197. As a result, drive spring 92*f* is held in a compressed, loaded state between rear rim 196 on carrier body 76*f* and rear cap 24*f*. The rearward or proximal end of drive spring 92*f* may be secured to rear cap 24*f* in the manner discussed previously in this disclosure. The forward or distal end of drive spring 92*f* may be associated with the proximal spring guide 86*f* and rear rim 196 of carrier body 76*f* in the manner described previously, and may be secured to rear rim 196 by suitable means such as by adhesive and/or direct mechanical attachment.

To carry out a puncturing procedure, the user grasps opposing sides of housing 12*f* and places the forward rim 42*f* of main body 20*f* in contact with a target location on a patient's body. The user then exerts downward pressure in the direction of Arrow X on lever 182, causing lever 182 to pivot (i.e., depress) into internal cavity 28*f* of main body 20*f*. As lever 182 pivots downward in internal cavity 28*f*, plate member 184 also moves downward in internal cavity 28*f* while initially maintaining an interference engagement with lancet 70*f* and thereby continuing to maintain the drive spring 92*f* in a compressed state. In particular, plate member 184 initially maintains an interference engagement with lancet 70*f*, wherein the forward side or surface of rear rim 196 and forward side or surface of guide tabs 78*f* on carrier body 76*f* are in interference engagement with the rearward side or surface of plate member 184 thereby maintaining the drive spring 92*f* compressed between rear rim 196 and rear cap 24*a*. As the lever 182 is continued to be depressed into main body 20*a*, keyhole 197 in plate member 184 eventually aligns with a matching transverse cross-sectional shape defined by carrier body 76*f* at the location of the rear rim 196 and guide tabs 78*f*, thereby permitting the carrier body 76*f* to pass through keyhole 197. As the interference engagement between the rear rim 196 and guide tabs 78*f* and plate member 184 is released, the stored potential energy in drive spring 92*e* is also released and used to move the lancet 70*f* to the puncturing position.

Figure 35:
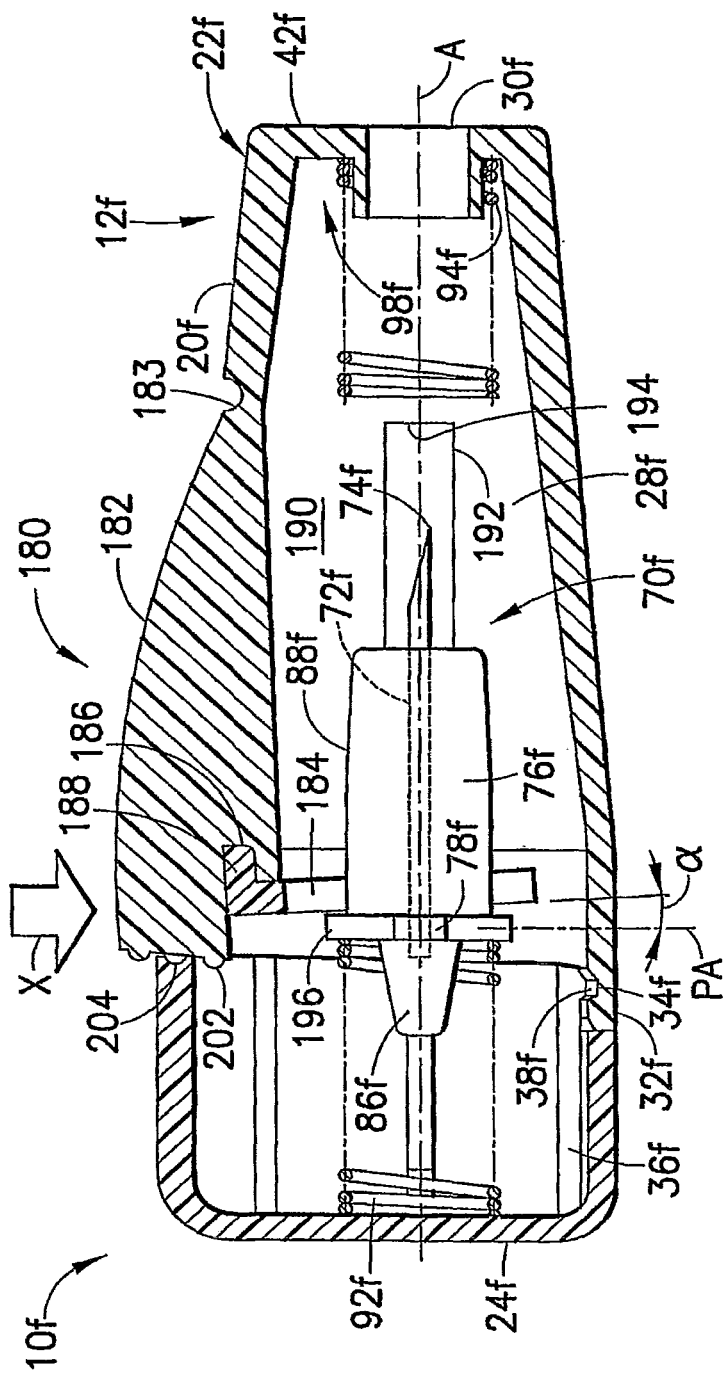
FIG. 35 is a longitudinal cross-sectional view of the lancet device of FIG. 31 showing the lancet device in the initial stage of actuation.
Figure 36:
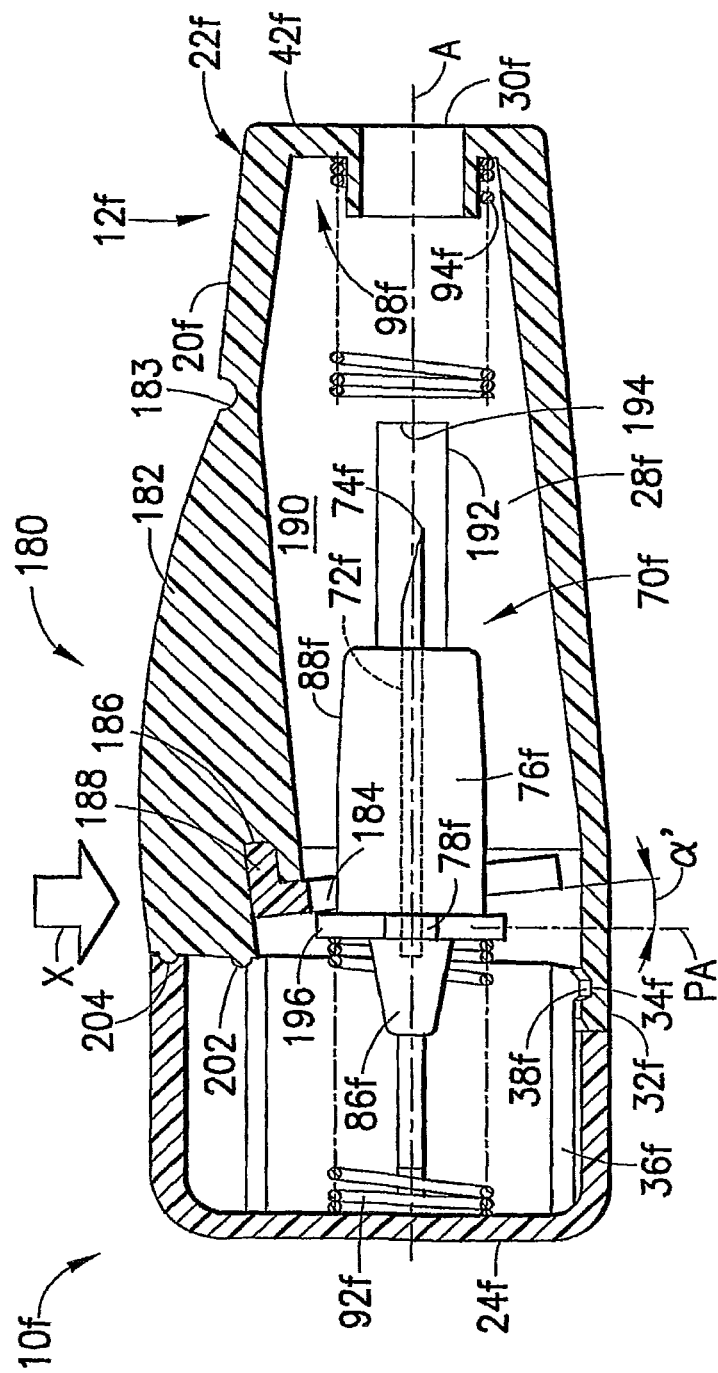
FIG. 36 is a longitudinal cross-sectional view of the lancet device of FIG. 31 showing the lancet device at the point of actuation.
Figure 37:
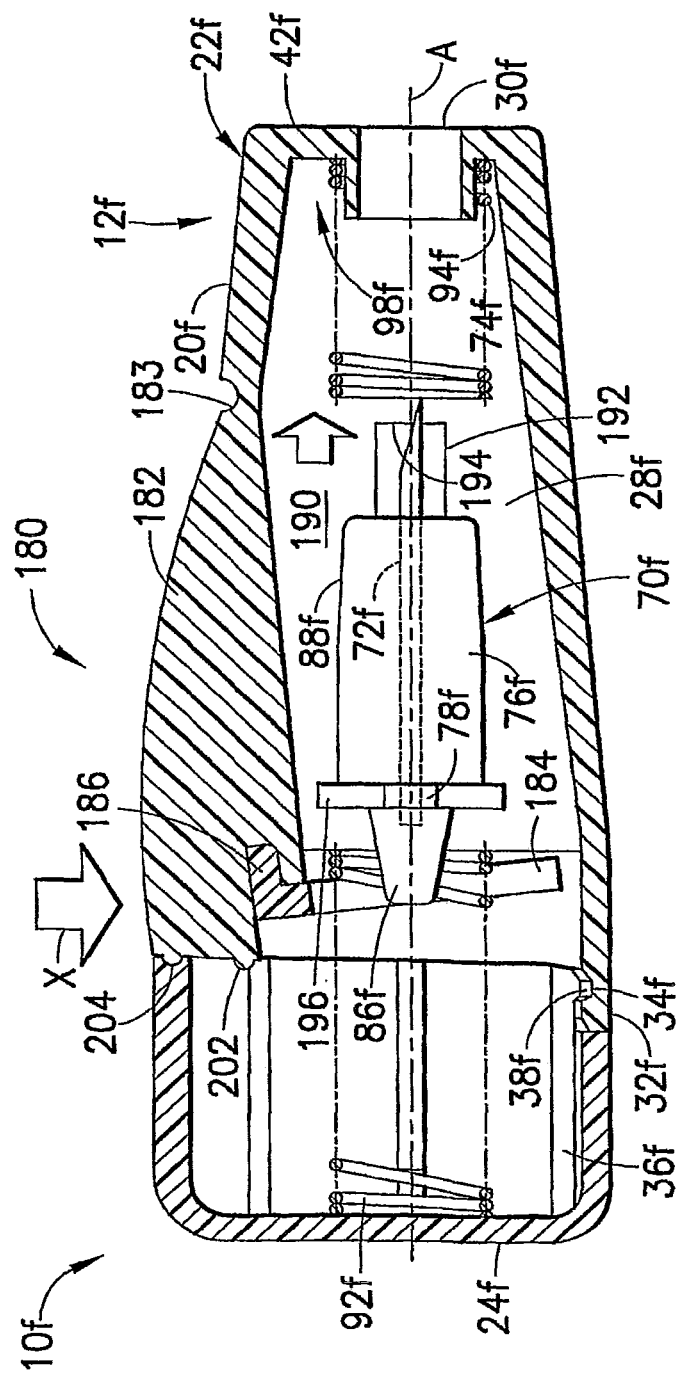
FIG. 37 is a longitudinal cross-sectional view of the lancet device of FIG. 31 showing the lancet device after actuation with the lancet moving within the device toward a puncturing position.
Figure 38:
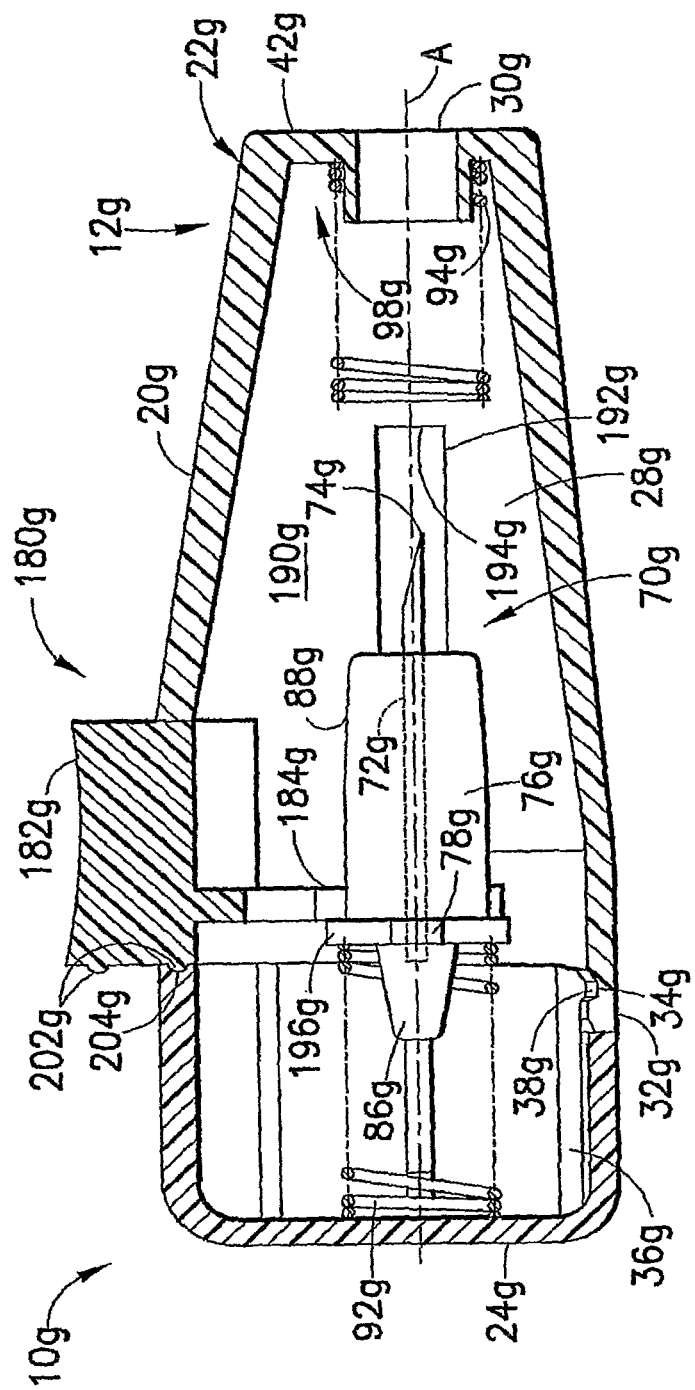
FIG. 38 is a longitudinal cross-sectional view of a seventh embodiment of the lancet device showing the lancet device in the initial, pre-actuated state.
Figure 39:
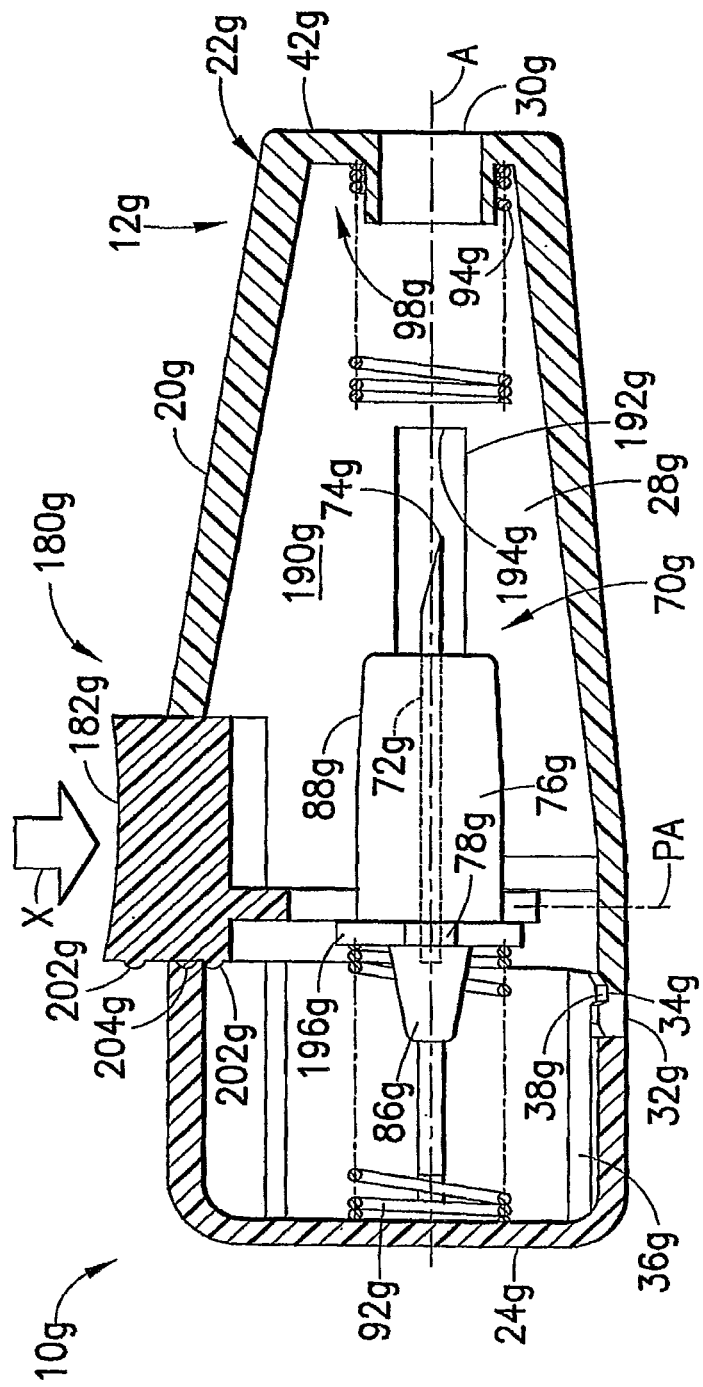
FIG. 39 is a longitudinal cross-sectional view of the lancet device of FIG. 38 showing the lancet device in the initial stage of actuation with the lancet in an interference engagement within the device.
Figure 40:
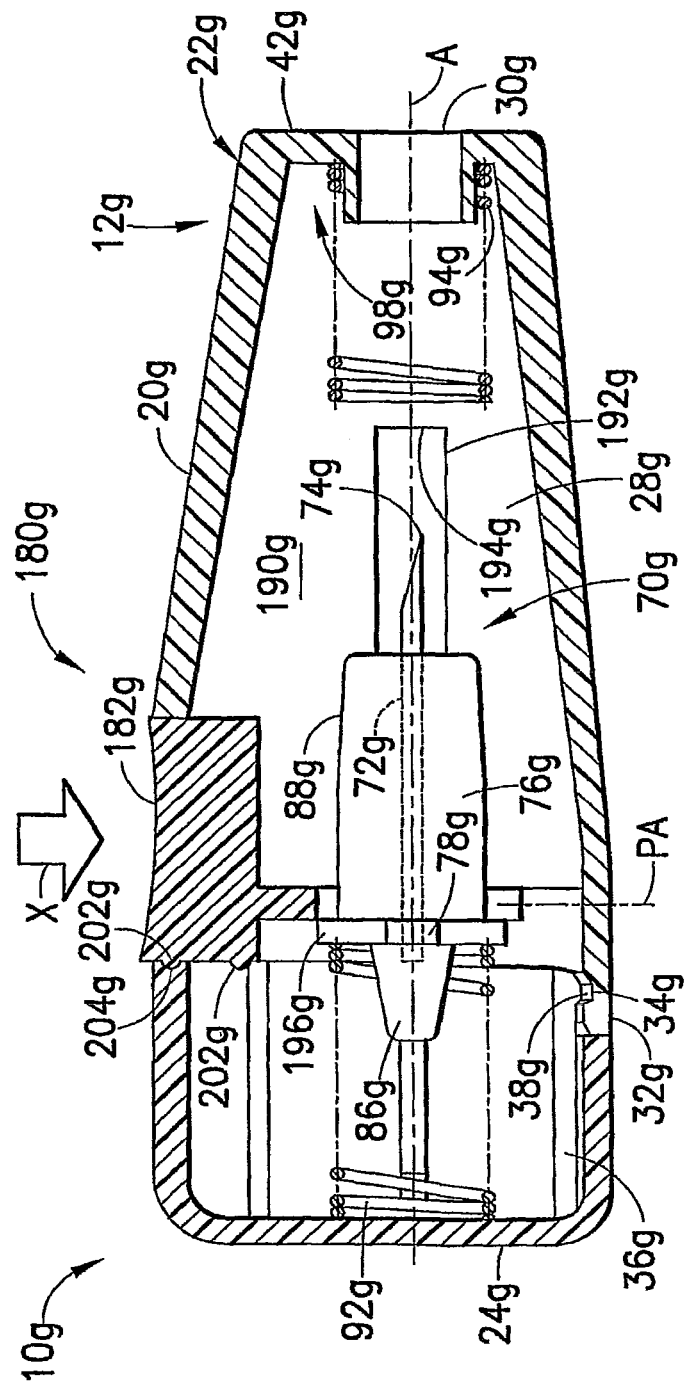
FIG. 40 is a transverse cross-sectional view of the lancet device of FIG. 38 showing the lancet device at the point of actuation with the lancet released of the interference engagement within the device.
Figure 43:
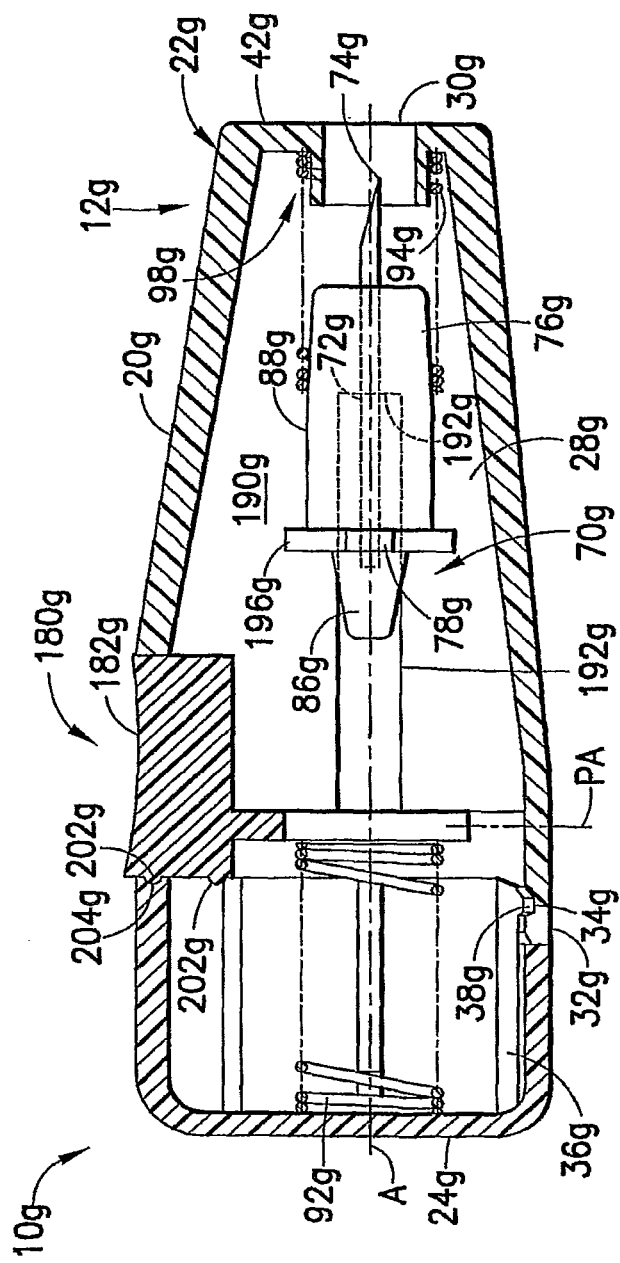
FIG. 43 is a longitudinal cross-sectional view of the lancet device of FIG. 38 showing the lancet device in the final state after actuation.

As shown in FIGS. 35-37, the pivotal movement of lever 182 results in a corresponding pivotal movement by plate member 184. As a result, as plate member 184 is pivoted downward into main body 20*f*, the plate member 184 begins to define an angle α with an axis perpendicular PA to the Central Axis A of lancet device 10*f* and housing 12*f* in particular. As the lever 182 is further depressed into main body 20*f*, the angle formed by plate member increases to angle α'. The angular orientation of plate member 184 causes keyhole 197 to be at a slight angular orientation relative to Central Axis A. As a result, as plate member 184 moves downward and slightly forward in main body 20*f*, keyhole 197 does not align exactly along Axis PA but at an angle to this axis. Due to the angular "offset" between keyhole 197 and the Central Axis A of main body 20*f*, the matching transverse cross-sectional shape defined by carrier body 76*f* at the location of the rear rim 196 and guide tabs 78*f* will not pass easily through keyhole 197 unless the size of keyhole 197 is increased to compensate for the angular orientation of plate member 184. Therefore, in lancet device 10f it is desirable to increase the size of keyhole 197 to compensate for the forward angular movement of plate member 184. Alternatively, plate member 184 could be positioned in a track such that pivotal movement of lever 182 translates into linearly tracked movement of plate member 184. Plate member 184 would still allow for providing clearance for rear rim 196 and guide tabs 78f to pass through keyhole 197.

With the stored potential in drive spring 92f released and providing a biasing force acting on lancet 70f, the drive spring 92f biases the lancet 70f away from rear cap 24f and through main body 20f. During such propelling movement, the engagement of guide tabs 78f in guide channels 192 guides lancet 70f axially through main body 20f. The biasing force applied to lancet 70f is preferably sufficient to cause the puncturing end 74f of lancet 72f to project a sufficient distance and with sufficient force from the front opening 30f in main body 20f to cause a puncture wound in the desired location on the patient's body. Moreover, during the propelling movement of lancet 70f, proximal spring guide 86f on carrier body 76f releases from drive spring 92f which remains connected to rear cap 24f. As the lancet 70f moves forward in the propelling movement, distal spring guide 88f engages retraction spring 94f. The biasing/propelling force of drive spring 92f is at least in part applied to retraction spring 94f by engagement of distal spring guide 88f with retraction spring 94f, which causes the retraction spring 94f to compress toward distal end pocket 98f. The retraction spring 94f is adapted to permit puncturing end 74f of lancet 72f to extend through front opening 30f in main body 20f a sufficient distance and with sufficient force to puncture the skin of the patient and initiate blood flow, and thereafter return lancet 70f to a substantially fixed and stationary position within housing 12f. As indicated, distal spring guide 88f desirably provides an abutment surface for engaging internal sleeve 96f supporting retraction spring 94f to prevent lancet 70f from axial movement entirely out of main body 20f of housing 12f through front opening 30f. As the retraction spring 94f returns to a relaxed or unloaded state within main body 20f, the lancet 70f is retracted in main body 20f and returned to a substantially fixed and stationary positioned within main body 20f. Thereafter, the engagement of retraction spring 94f with distal spring guide 88f maintains the lancet 70f within main body 20f, with the puncturing end 74f of lancet 72f shielded within housing 12f and preventing further movement of lancet 70f to the puncturing position.

Referring to FIGS. 38-43, a seventh embodiment of a lancet device 10g is shown and which is a variation of lancet device 10f described immediately previously. Lancet device 10g is similar in all respects to lancet device 10f described immediately above, except for comprising a different configuration of actuation structure or actuator 180g, which will now be detailed. Actuator 180g of lancet device 10g replaces the pivoting lever 182 of actuator 180 of lancet device 10f with a depressible button 182g, which allows plate member 184g to be depressed into main body 20g directly along Axis PA, such that plate member 184g no longer pivots into main body 20g and thereby form an angle with Axis PA, as was the case with the lever 182 and depending plate member 184 of actuator 180 in lancet device 10f. Other than the foregoing difference between actuator 180g of lancet device 10g and actuator 180 of lancet device 10f, all other aspects of lancet device 10g are identical to lancet device 10f described previously.

As further shown in the FIGS. 31-43 associated with lancet devices 10f, 10g, actuation structures or actuators 180, 180g of these devices comprise a structure for engaging main bodies 20f, 20g of housing 12f, 12g such that, once actuation structures or actuators 180, 180g are depressed, the actuators 180, 180g are prevented from returning to their initial positions. In actuators 180, 180g, one or more detents 202, 202g are provided on a proximal or rearward end of lever 182 and a proximal or rearward end of button 182g, respectively. Detents 202, 202g are adapted to engage in a snap-fit or friction-fit manner with a mating recess 204 defined in main bodies 20f, 20g. Recesses 204, 204g in main bodies 20f, 20g are provided opposite to the proximal or rearward end of lever 182 and the proximal or rearward side of button 182g, respectively. In operation, as lever 182 and button 182g are depressed into main bodies 20f, 20g, respectively, detents 202, 202g successively engage the mating recesses 204, 204g in main bodies 20f, 20g. The mating engagement of detents 202, 202g in mating recesses 204, 204g prevents lever 182 and button 182g from returning to their initial positions. The use of multiple detents 202, 202g allows lever 182 and button 182g to be moved in discrete downward steps or stages to the actuating position, where keyholes 196, 196g defined in plate members 184, 184g align with the matching or corresponding transverse cross-sectional shape of carrier bodies 76f, 76g to permit lancets 70f, 70g to move to the puncturing position.

Referring to FIGS. 44-52, an eighth embodiment of a lancet device 10h is generally illustrated, and generally comprises a housing 12h and a lancet 70h disposed in housing 12h. Lancet device 10h differs from lancet devices 10a-c, e discussed previously, as lancet device 10h is not actuated through the retraction (i.e., depression) of a shield element into housing 12h. However, lancet device 10h is similar to lancet devices 10d, 10f, and 10g discussed previously because lancet device 10h is initially provided in an armed or loaded state, with lancet 70h ready to be biased to the puncturing position by drive spring 92h upon release or removal of an interfering engagement or structure, and likewise comprises a depressible actuation structure or actuator for releasing or removing the interference engagement. Additionally, lancet device 10h incorporates a cutting and shearing concept such as that utilized in lancet devices 10a, 10b to remove the interference engagement. As in previous embodiments, in the initial armed state of lancet device 10h, drive spring 92h is in a compressed (i.e., loaded) state, ready to bias the lancet 70h to a puncturing position in skin-puncturing operation upon removal of an interference engagement.

Housing 12h of lancet device 10h comprises an elongated main body 20h that generally has a cylindrical and hollow configuration. The main body 20h has a distal or forward end portion 22h, and a rear cap 24h forming a proximal or rearward end portion 26h of the main body 20h. The interior of main body 20h is generally open and defines an internal cavity 28h. The internal cavity 28h is closed at the rearward end due to the presence of rear cap 24h and includes a front opening 30h defined in forward end portion 22h of main body 20h, and through which lancet 70h extends when lancet device 10h is actuated. Main body 20h and rear cap 24h may be integrally formed. Typically, main body 20h and rear cap 24h are separate elements that are affixed together to form housing 12h, as illustrated, which facilitates assembly of lancet device 10h. As examples, main body 20h and rear cap 24h may be affixed together through an appropriate medical grade adhesive, and/or may connected using inter-engaging structures providing a mechanical engagement therebetween, such as a friction-fit or a snap-fit construction. For example, main body 20h may comprise an annular rim 32h that cooperates with an annular rim 36h on rear cap 24h and which is recessed to accept annular rim 32h. An adhesive, such as a medical grade adhesive, may be used to secure annular rim 32h with annular rim 36h. As with lancet devices 10d, 10f, and 10g, distal or forward end portion 22h of main body 20h comprises an axially rearward-extending sleeve 96h which defines a distal end pocket 98h for receiving and supporting retraction spring 94h.

Additionally, main body 20h of housing 12h further comprises a pivoting actuation structure or actuator 206 in a generally analogous manner to lancet device 10d described previously, for causing actuation of lancet 70h and corresponding release of drive spring 92h. Actuation structure or actuator 206 generally comprises an actuating lever 208 that is pivotally movable relative to main body 20h, and is desirably located at the rear end portion 26h of main body 20h proximate to rear cap 24h. Actuating lever 208 may extend distally or forward from rear cap 24h and be connected to rear cap 24h by a living hinge or equivalent structure. Lever 208 may thus be integrally formed with rear cap 24h. The lever 208 may alternatively be associated with main body 20h. For example, lever 208 may be formed as part of the rear end portion 26h of main body 20h, or even formed as part of the forward end portion 22h of main body 20h and extend rearward or proximally toward rear cap 24h. In contrast to previous embodiments, lever 208 comprises two opposed and depending sidewalls 210. Sidewalls 210 terminate with a cutting edge or blade 212. Cutting edge 212 may be an integral, sharp edge on sidewalls 210 or be provided as a separate cutting blade secured to the ends of sidewalls 210. Lever 208 is generally adapted to be depressed into the internal cavity 28h of main body 20h so that cutting edges 212 may cut or sever an interfering engagement within in main body 20h restraining drive spring 92h, and thereby cause actuation of lancet device 10h as described in detail herein.

Figure 46:
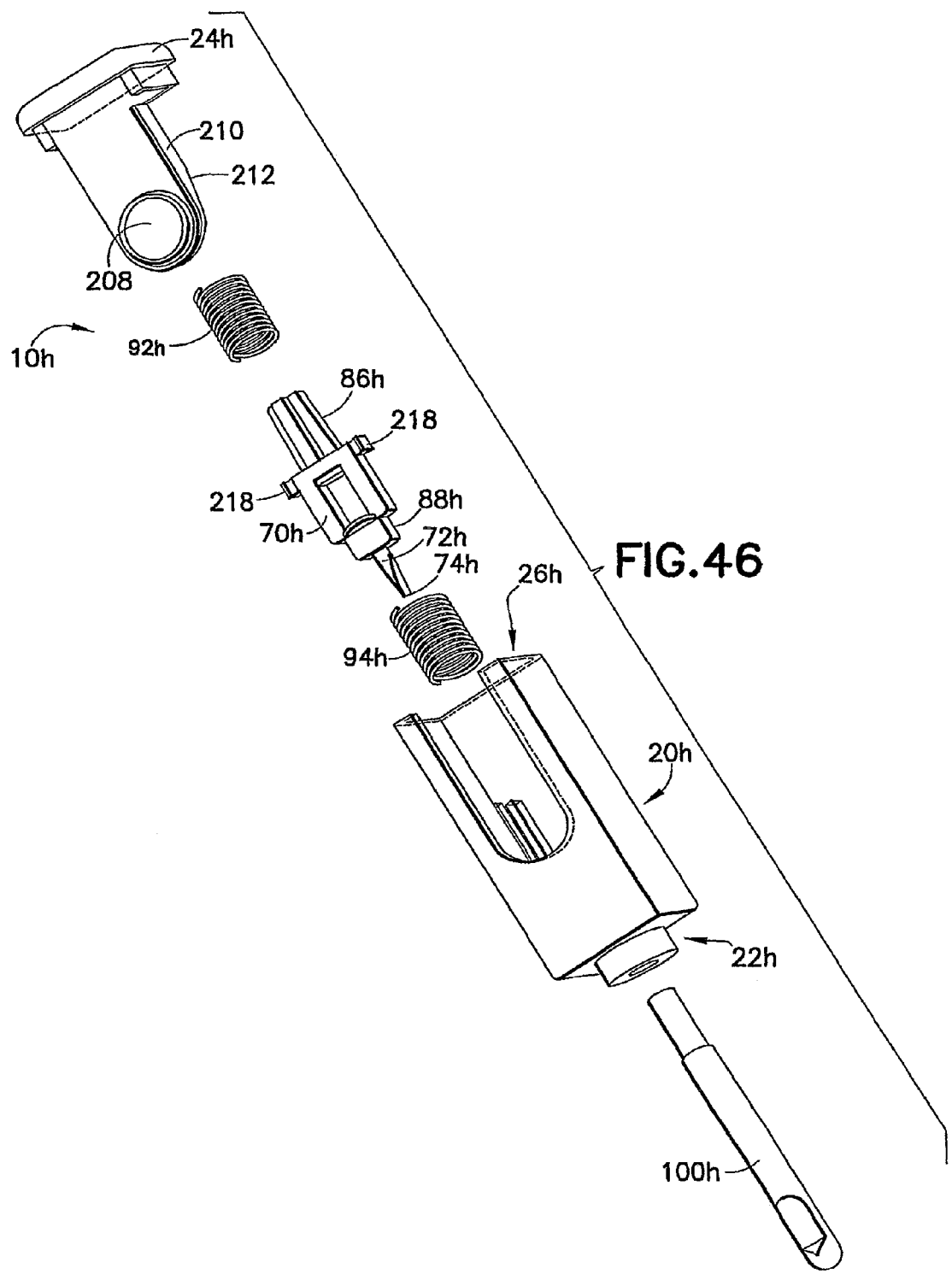
FIG. 46 is an exploded perspective view of the lancet device of FIG. 44.
Figure 47:
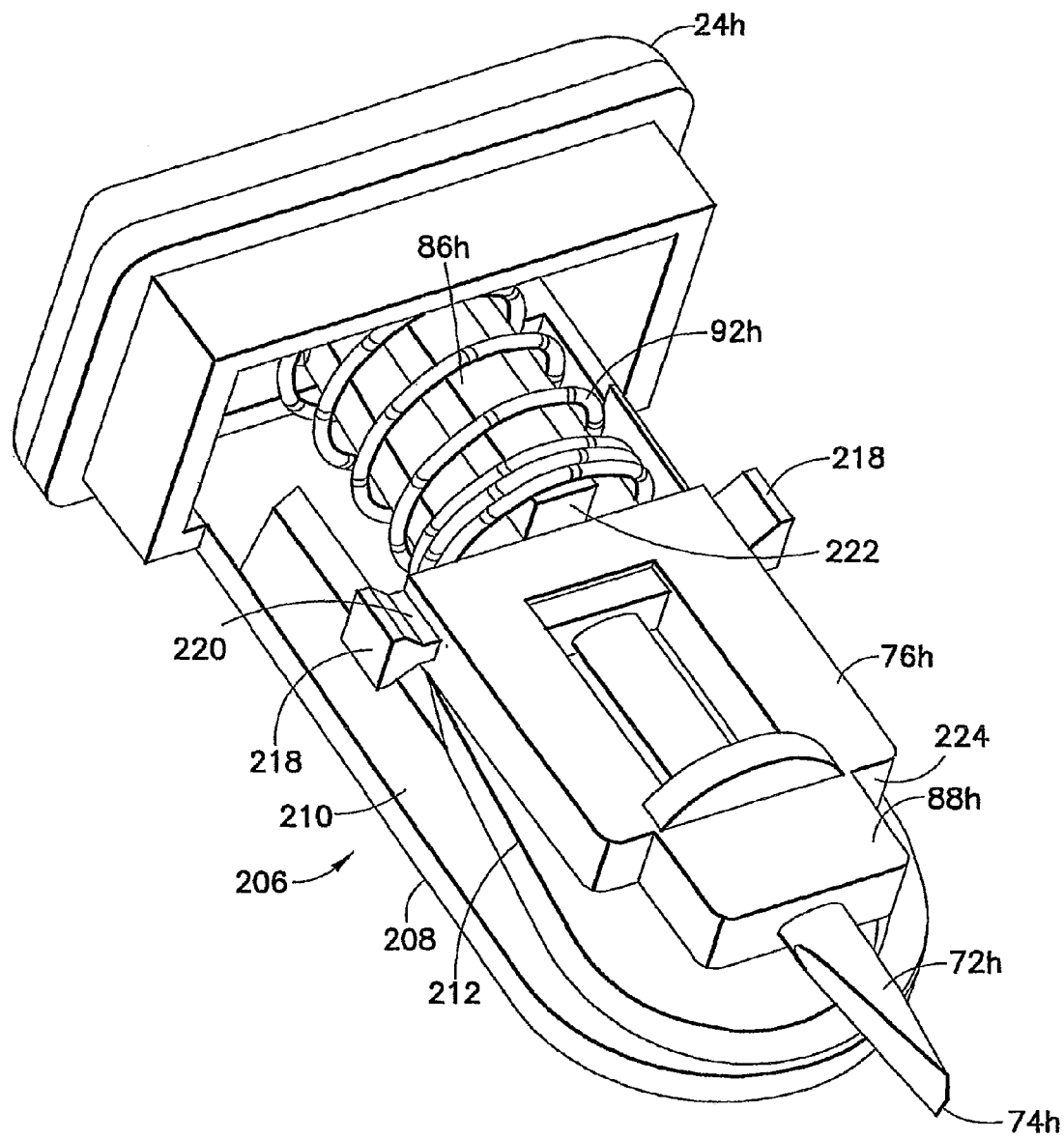
FIG. 47 is a perspective view of a portion of the lancet device of FIG. 44 showing an actuator, a drive spring, and the lancet of the device.
Figure 48:
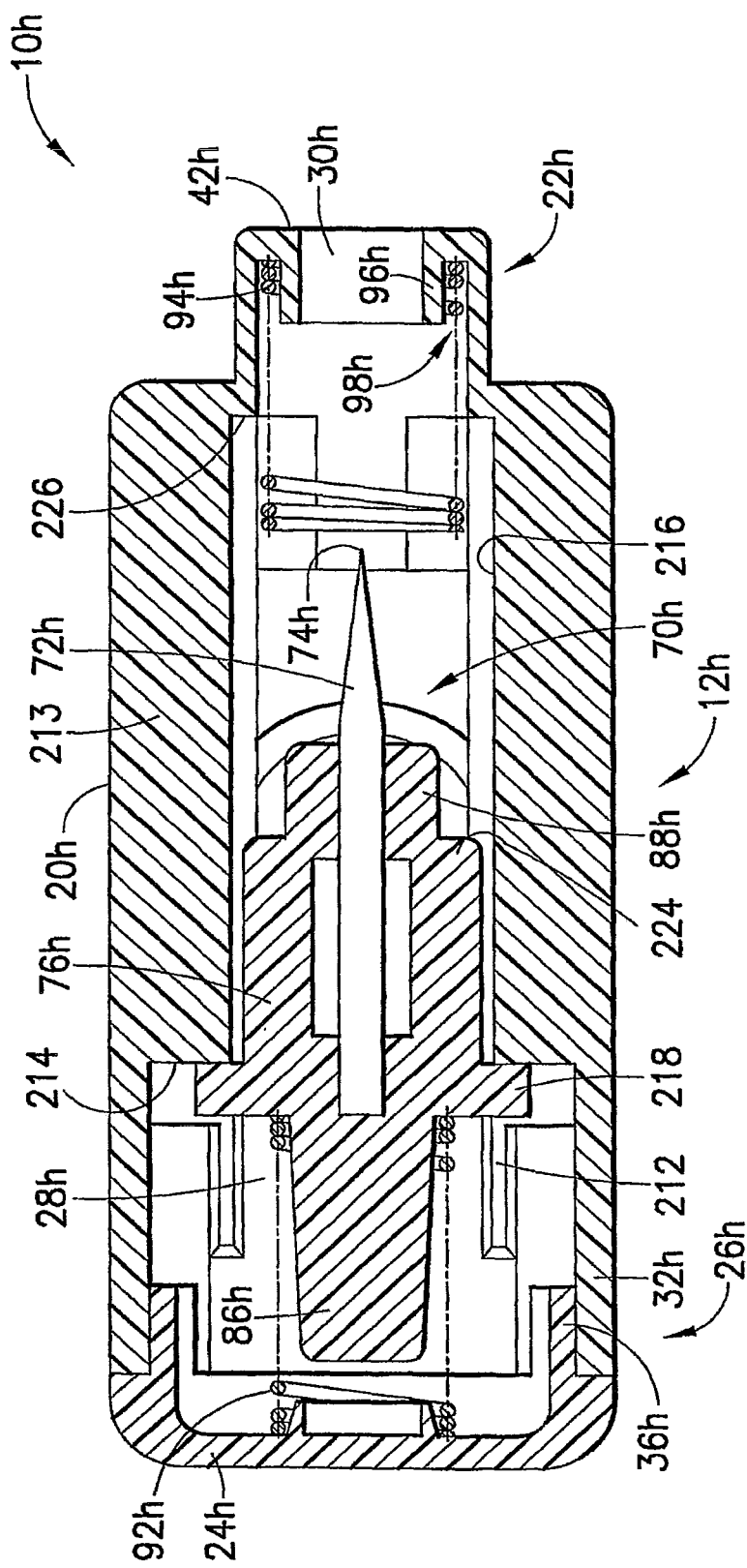
FIG. 48 is a longitudinal cross-sectional view of the lancet device of FIG. 44 showing the lancet device in the initial, pre-actuated state.
Figure 49:
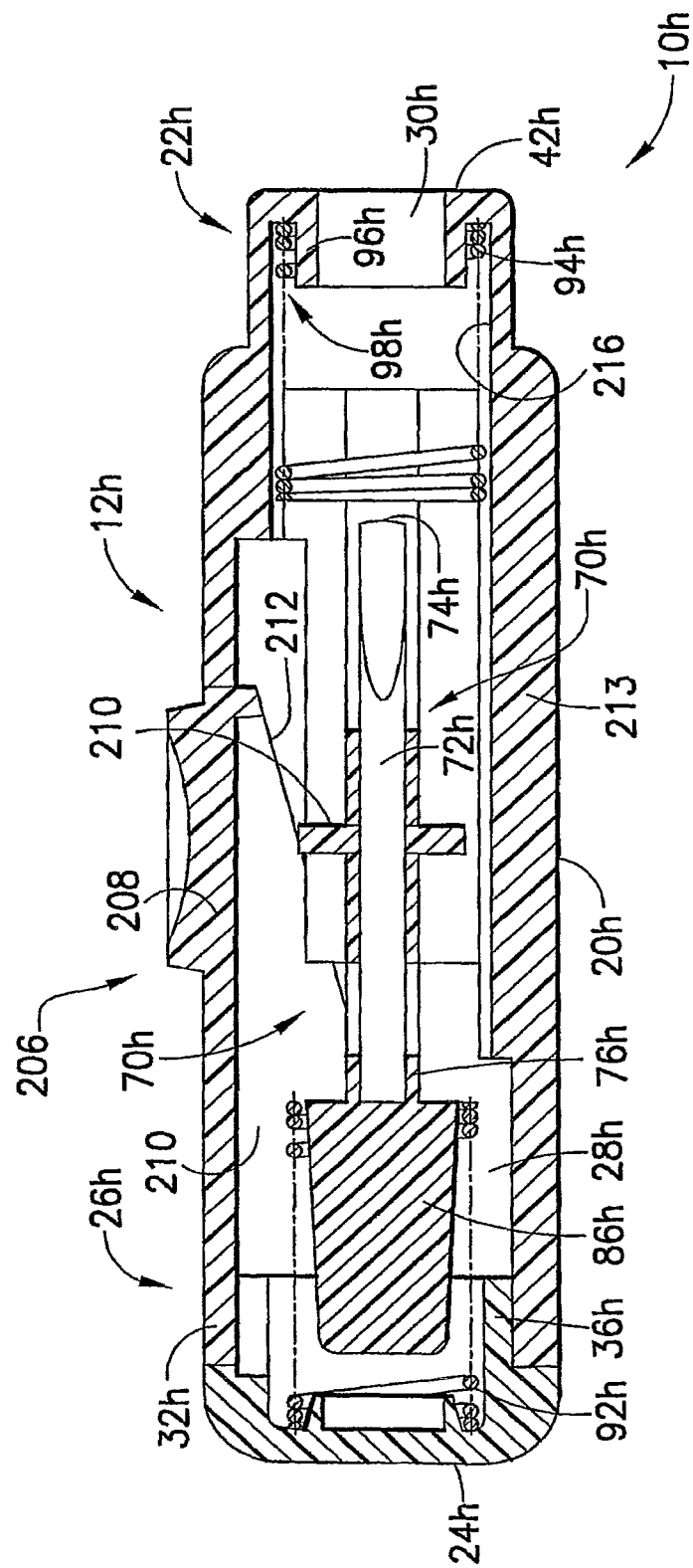
FIG. 49 is a longitudinal cross-sectional view of the lancet device of FIG. 44 taken along a perpendicular longitudinal axis to the cross-sectional view in FIG. 48.
Figure 50:
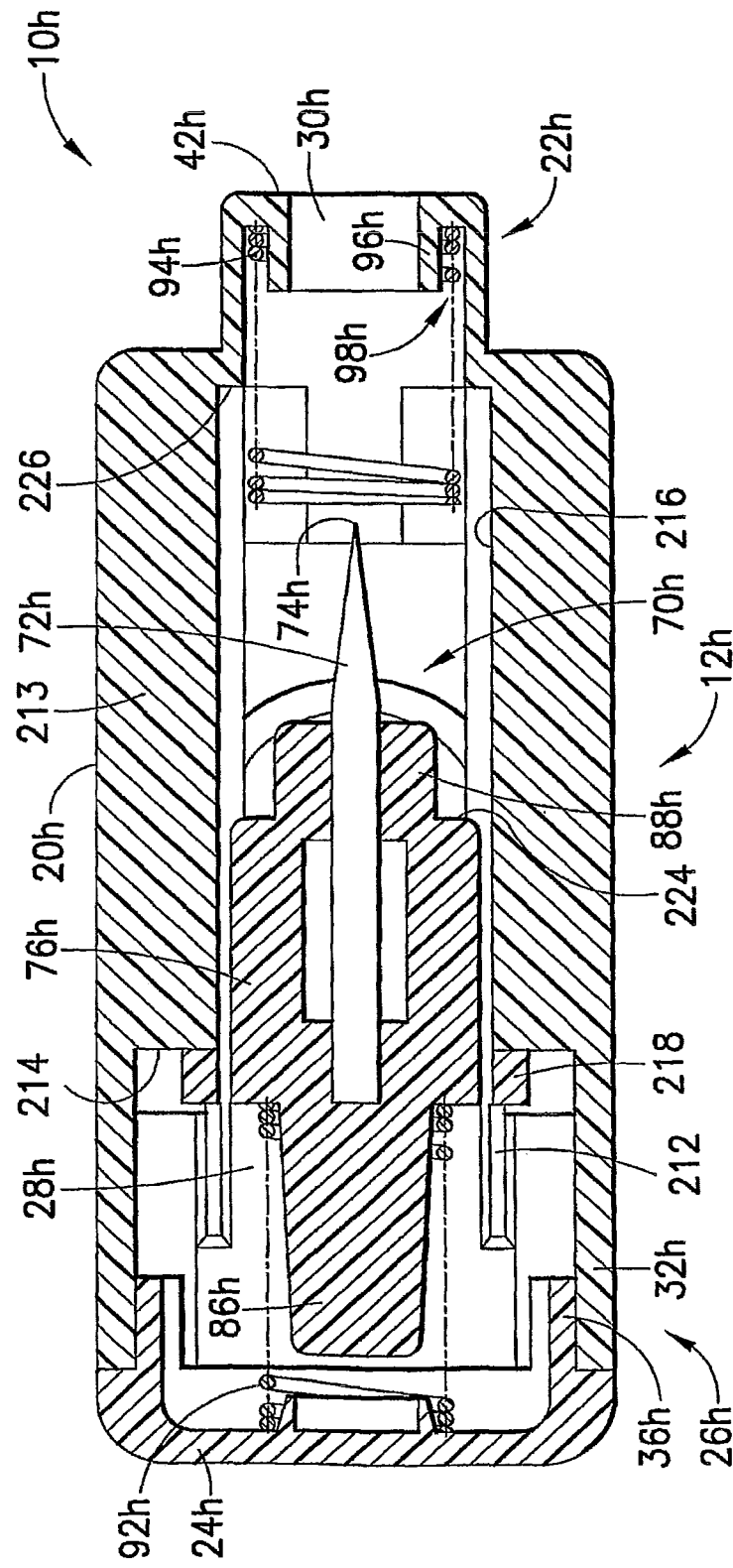
FIG. 50 is a longitudinal cross-sectional view of the lancet device of FIG. 44 showing the lancet device at the point of actuation.
Figure 51:
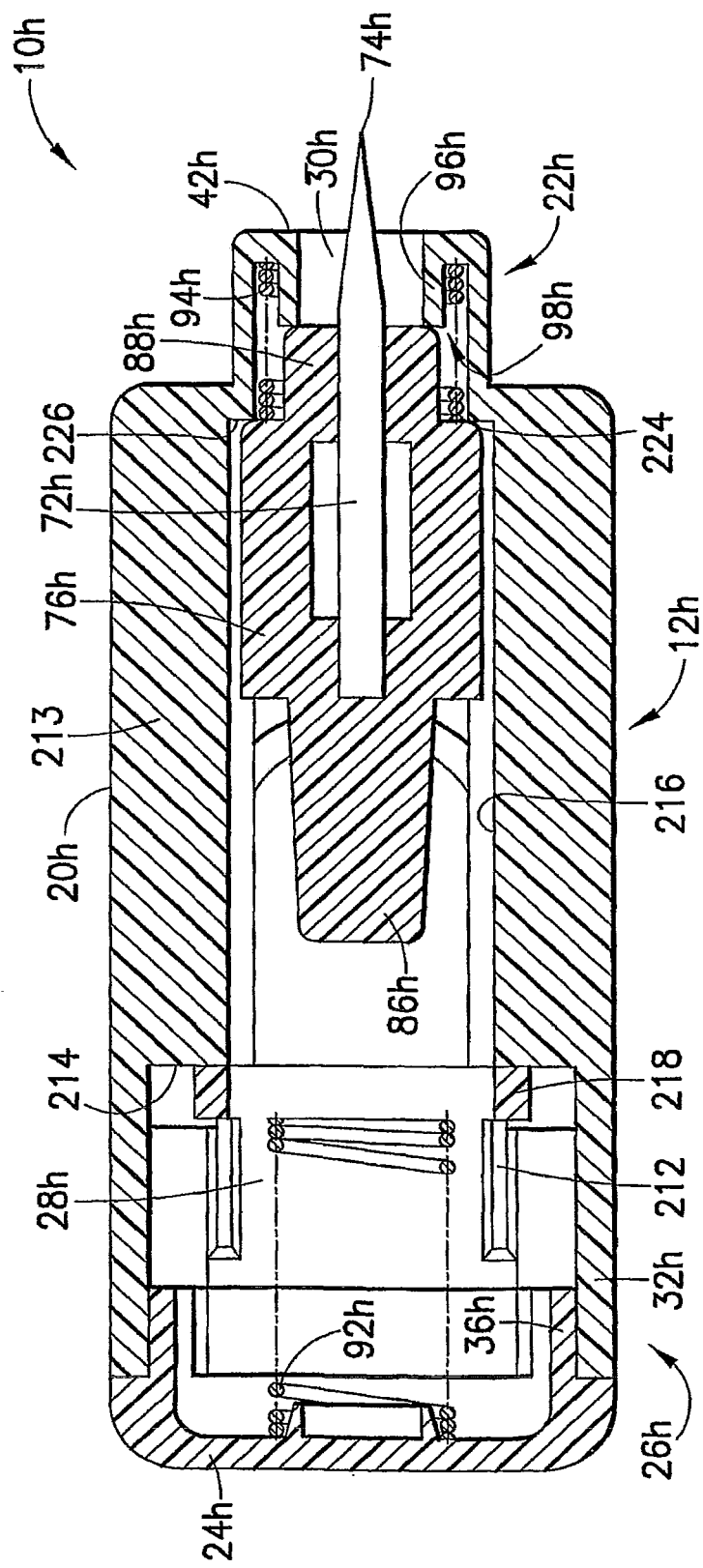
FIG. 51 is a longitudinal cross-sectional view of the lancet device of FIG. 44 showing the lancet device after actuation with the lancet of the device partially exposed for a puncturing procedure.
Figure 52:
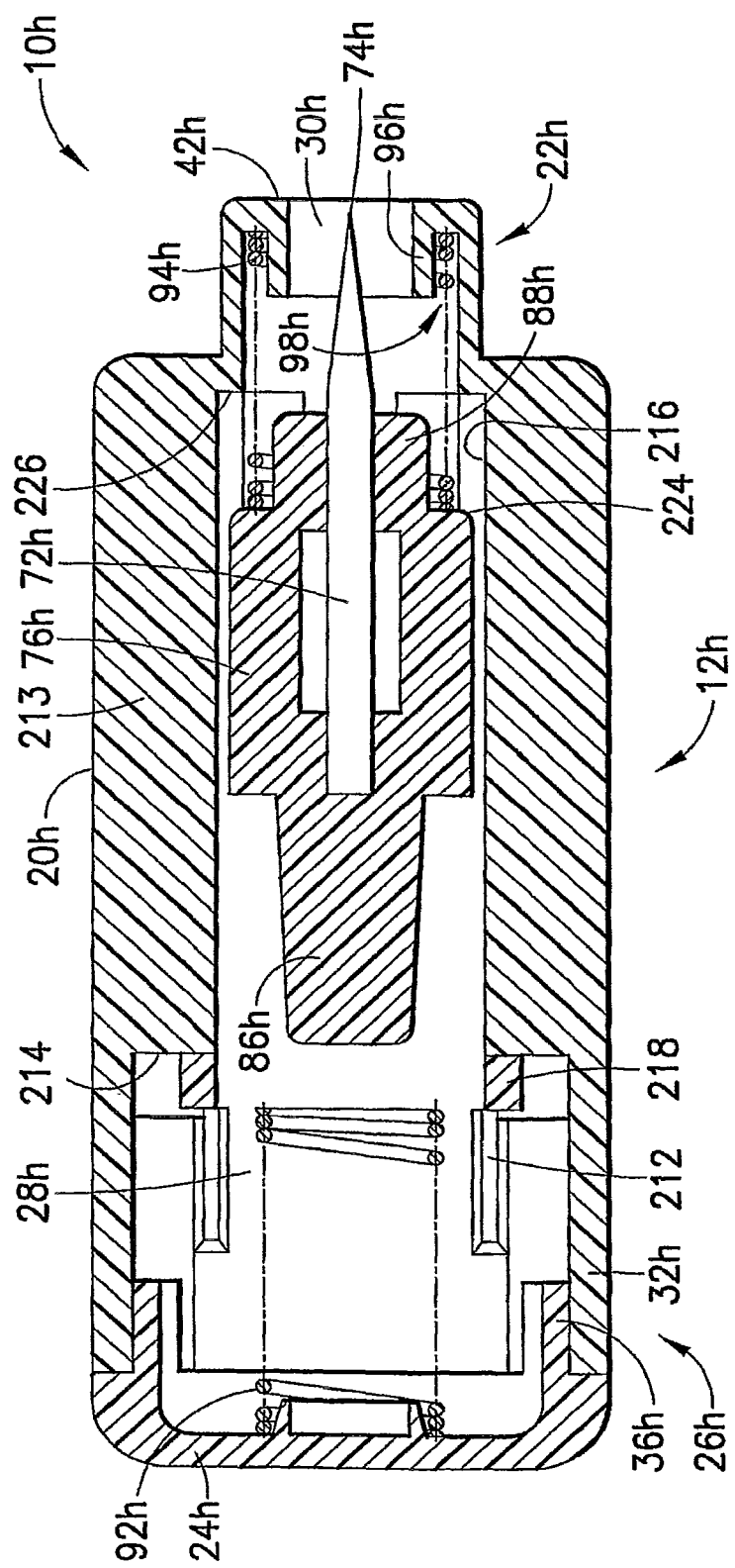
FIG. 52 is a longitudinal cross-sectional view of the lancet device of FIG. 44 showing the lancet device in the final state after actuation.

Main body 20h of housing 12h may be formed with a generally rectangular cross-section as illustrated in FIG. 46 and comprise opposing inner sidewalls 213 each defining an internal shelf or ledge 214. Lancet 70h is generally adapted to engage shelves 214 for restraining compressed drive spring 92h and, upon depression of lever 208 into main body 20h, a structure on lancet 70h is cut or severed to release the interference engagement of lancet 70h with shelves 214 and, thus, release the biasing force of drive spring 92h. Main body 20h defines a main guide channel 216 that accommodates lancet 70h and guides movement of lancet 70h within main body 20h.

Lancet 70h is formed in a generally analogous manner as previous embodiments and comprises a lancet 72h with a puncturing end 74h at the forward end thereof, and a carrier body 76h supporting lancet 72h at the rearward end thereof. The carrier body 76h now comprises a pair of outward extending tab members 218 which generally take the place of the guide tabs discussed previously in this disclosure. Tab members 218 are adapted for interference engagement with shelves 214 for positioning lancet 70h in housing 12h and main body 20h in particular. The interference engagement between tab members 218 and shelves 216 further serves to restrain compressed drive spring 92h. Tab members 218 are adapted to be cut or severed by cutting edge 212 on sidewalls 210 upon depression of lever 208 into main body 20h. For this purpose, tab members 218 may define a tapered cross-section forming a narrow neck or weakened area 220 which may be cut through by cutting edge 212 on sidewalls 210. Neck area 220 may take other forms, such as a score line, but is generally adapted to be easily cut or sheared through (i.e., cause failure of) by cutting edge 212 when lever 208 is depressed into main body 20h of housing 12h. Carrier body 76h further comprises a proximal or rearward end spring guide 86h and a distal or forward end spring guide 88h for engaging drive spring 92h and retraction spring 96h, respectively, of lancet device 10h. Spring guides 86h, 88h may be formed integral with the body of carrier body 76h or be provided as distinct, separate elements and secured to the body of carrier body 76h in the manner described previously.

In operation, lancet 70h is adapted for axial movement through the main guide channel 216 of main body 20h between an initial position wherein tab members 218 are in interference engagement with shelves 214 defined by main body 20h and the puncturing end 74h of lancet 72h is disposed entirely within main body 20d, to a puncturing position wherein carrier body 76h is disposed in main guide channel 216 with the puncturing end 74h extending beyond front opening 30h of main body 20h a sufficient distance to cause a puncture wound in a patient's body. In the initial, pre-actuated state of lancet device 10h, drive spring 92h is at least partially compressed between rear cap 24h and carrier body 76h and typically has sufficient stored potential energy to conduct a skin-piercing procedure. The rearward or proximal end of drive spring 92h is typically secured to rear cap 24h in the manner discussed previously in this disclosure. The forward or distal end of drive spring 92h is associated with carrier body 76h and disposed about proximal spring guide 86h, and may be secured to carrier body 76h by similar means discussed previously, as by suitable adhesive or direct mechanical attachment. As shown, for example, in FIG. 47, drive spring 92h directly engages carrier body 76h, and the carrier body 76h may further comprise two outward-extending tabs or flanges 222 against which the forward end of drive spring 92h is engaged to provide additional surfaces for transmitting the biasing force of drive spring 92h to lancet 70h to move the lancet 70h to the puncturing position.

With continued reference to FIGS. 44-52, use and operation of lancet device 10h will now be discussed. As with previous embodiments, a cover (not shown) extending distally from carrier body 76h may be provided with carrier body 76h. As with previous embodiments, such a cover would be removed by breaking the frangible connection with carrier body 76h and withdrawing the cover from front opening 30h in main body 20h. Forward end rim 42h of main body 20h may then be placed in contact with the target location on the patient's body. As indicated previously, lancet device 10h is initially provided in an armed state, with lancet 70h ready to initiate a puncturing procedure when compressed drive spring 92h is released.

To carry out a puncturing procedure, the user grasps opposing sides of housing 12h and exerts downwardly directed force in the direction of Arrow X on lever 208, causing lever 208 to pivot (i.e., depress) into internal cavity 28h of main body 20h. As lever 208 is depressed into main body 20h, depending sidewalls 210 and, more particularly, cutting edge 212 at the end of each depending sidewall 210 contacts tab members 218 at the reduced cross-sectional, weakened area 220 on tab members 218. As the lever 208 is continued to be depressed into main body 20h, cutting edge 212 on sidewalls 210 begins to cut through the neck area 220 on each tab member 218. Once the tab members 218 are completely cut-through, the interference engagement between tab members 218 and shelves 214 defined by sidewalls 213 of main body 20h is removed, releasing the drive spring 92b to bias lancet 70h to the puncturing position. With the biasing force of drive spring 92h released, drive spring 92h thereafter biases the lancet 70h away from rear cap 24h and through main guide channel 216. The biasing force imparted to lancet 70h is preferably sufficient to cause the puncturing end 74h of lancet 72h to project a sufficient distance and with sufficient force from the front opening 30h in main body 20h to cause a puncture wound in the desired location on the patient's body. Moreover, during the propelling movement of lancet 70h, proximal spring guide 86h on carrier body 76h releases from drive spring 92h which remains connected to rear cap 24h.

As the lancet 70h moves forward in the propelling movement, distal spring guide 88h engages retraction spring 94h. The biasing/propelling force provided by drive spring 92h is at least in part applied to retraction spring 94h by engagement of distal spring guide 88h with retraction spring 94h, which causes the retraction spring 94h to compress toward distal end pocket 98h. The retraction spring 94h permits puncturing end 74h of lancet 72h to extend through front opening 30h in main body 20h a sufficient distance and with sufficient force to puncture the skin of the patient and initiate blood flow, and thereafter return lancet 70h to a substantially fixed and stationary position within housing 12h. Carrier body 76h is desirably formed with a shoulder 224 formed at the base of distal spring guide 88h, and which is configured to engage an abutment surface or stop 226 defined by sidewalls 213 of main body 20h in main guide channel 216 to prevent lancet 70h from axial movement entirely out of main body 20h through front opening 30h. The stop 226 is defined rearward of rearward-extending internal sleeve 96h supporting retraction spring 94h. As the retraction spring 94h returns to a relaxed or unloaded state within main body 20h, the lancet 70h is retracted in main body 20h and returned to a substantially fixed and stationary positioned within main body 20h. Thereafter, the engagement of retraction spring 94h with distal spring guide 88h maintains the lancet 70h shielded within housing 12h, and prevents further movement of lancet 70h to the puncturing position, in the manner discussed in detail previously. In this disclosure, various elements have been identified as being adapted to be "cut", "sheared", "yielded", "fractured" to cause release and actuation of lancet device 10. These terms may all be grouped under a common heading of a "failure" item or element which is intended to fail when force is applied thereto in whatever form, for example blunt force or a cutting force.

Figure 55:
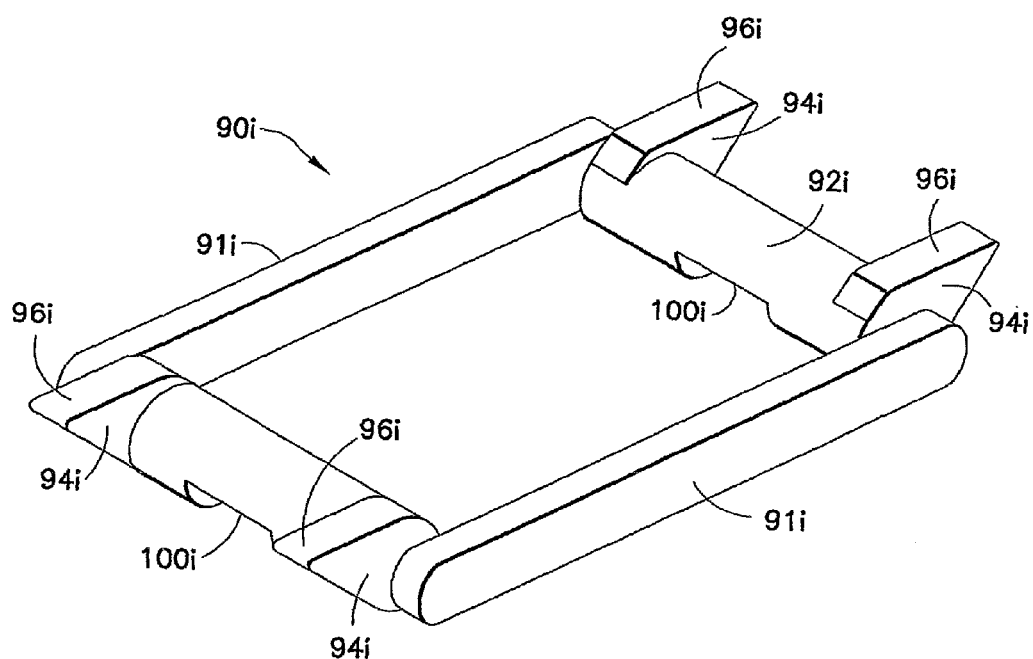
FIG. 55 is a perspective view of the retaining hub shown in FIGS. 54A-54C
Figure 56:
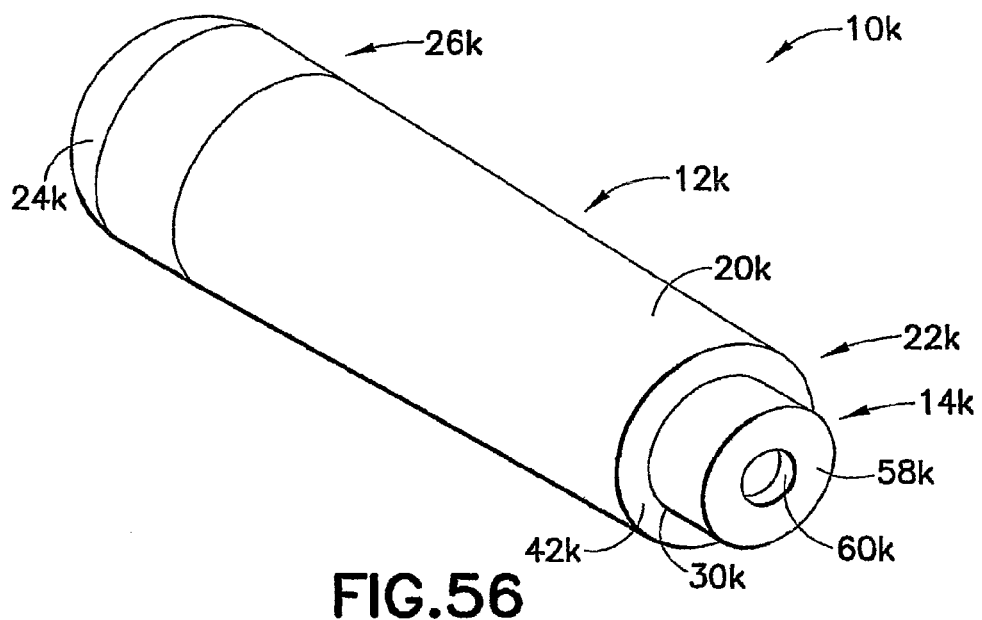
FIG. 56 is a perspective view of a final embodiment of the lancet device.

Referring to FIGS. 53-55, a modification to a lancet device disclosed in U.S. patent application Ser. No. 11/270, 330, filed Nov. 30, 2004, and entitled "Contact Activated Lancet Device", the entire disclosure of which is incorporated herein by reference, is shown. Lancet device 10 disclosed in the foregoing incorporated reference document may include a modified version of a retaining hub 90i. FIG. 53 shows the retaining hub 90i as part of the lancet device 10 disclosed in the incorporated reference document, the disclosure of which will be used to describe the location and operation of retaining hub 90i. Retaining hub 90i generally defines an annular shape and is adapted to maintain the lancet 70 in an initial armed position retracted within housing 12. Retaining hub 90i typically includes two opposed and elongated support members 91i connected by two pivotal cam elements 92i to form the annular shape of retaining hub 90i. Cam elements 92i each include two outward-extending shafts 93i engaged pivotally with the opposed support members 91i. Cam elements 92i each further include at least one typically wedge-shaped contact element 94i defining an upper contact surface 96i on the upper surface thereof. Cam elements 92i each further define a generally centrally located recess or cut-out 100i defined in a bottom side thereof. The purpose of recess 100i is described herein in connection with the operation of retaining hub 90i in lancet device 10. As shown in FIGS. 54 and 55, the cam elements 92i desirably each include two contact elements 94i disposed generally at opposite ends of the cam elements 92i, with the recess 100i defined in the bottom side of the cam elements 92i between the contact elements 94i.

In lancet device 10, retaining hub 90i and lancet 70 are in interference engagement with each other, such that retaining hub 90i retains the lancet 70 in an initial armed state retracted within housing 12. For example, fingers 82 on carrier element 76 may rest on the upper side of cam elements 92i, thereby providing interference engagement between the lancet 70 and the retaining hub 90i. Moreover, upper contact surface 96i on the contact elements 94i may be adapted for contacting engagement with structure within housing 12. For example, rear cap 24 of housing 12 may include structure extending therein, such as internal contact 46 integrally formed and extending on at least one, and desirably on two opposing inner sidewalls thereof. As retaining hub 90i typically includes two contact elements 94i on each cam element 92i, two internal contacts 46 may be provided on each of the two opposing inner sidewalls of the housing 12. Each internal contact 46 includes a distal engagement cam surface 47 for contacting engagement with the corresponding contact surface 96i on contact elements 94i.

During usual operation of the lancet device 10, axial movement of shield body 50 toward rear cap 24, causes the retaining hub 90i to be displaced rearwardly toward rear cap 24, with fingers 82 of the carrier element 76 resting upon the cam elements 92i. Such rearward movement of retaining hub 90i causes the contact surfaces of engagement cam surfaces 47 of the internal contacts 46 within rear cap 24 to engage and co-act with the corresponding contact surfaces 96i on the contact elements 94i of cam elements 92i. Such engagement and continued downward movement of internal contacts 46 causes the cam elements 92i to pivot on or rotate about shafts 93i with respect to support members 91i. Due to the generally wedge-shaped profile of the contact elements 94i, the pivotal movement of cam elements 92i has the effect of further compressing drive spring 102 by further "lifting" fingers 82, at least until the point where rear nub 86 on carrier element 76 contacts the inner side of rear cap 24. At this point, continued axial displacement of shield body 50 toward rear cap 24 pivots cam elements 92i to a position where recess 100i defined in the bottom side of cam elements 92i has rotated to a position generally aligned with fingers 82 at which point the interference engagement between fingers 82 and cam elements 92i is released by such alignment. The biasing force of drive spring 102 then propels lancet 70 downward away from the rear cap 24 axially through housing 12 and shield body 50, with guide tabs 78 passing axially through the annular opening defined by retaining hub 90i.

Referring to FIGS. 56-67, a final embodiment of a lancet device 10k is generally shown. Lancet device 10k generally includes a housing 12k, a shield 14k movably associated with the housing 12k, and a lancet 70k movably disposed in housing 12k. Shield 14k is movably associated with housing 12k, and is at least partially disposed within housing 12k. Shield 14k extends outward from housing 12k, while the lancet 70 is contained within housing 12k and is typically axially movable through the shield 14k.

Housing 12k comprises an elongated main body 20k having a generally cylindrical and hollow configuration. Main body 20k has a distal or forward end portion 22k, and a rear cap 24k forming a proximal or rearward end portion 26k of the main body 20k. The interior of main body 20k is generally open and comprises an internal cavity or bore 28k. The internal cavity 28k is closed at the rearward end due to the presence of rear cap 24k, and includes a front opening 30k defined by forward end portion 22k of main body 20k, and through which shield 14k extends. Main body 20k and rear cap 24k may be integrally formed. Alternatively, main body 20k and rear cap 24k may be separate elements that are affixed together to form housing 12k in the general manner described previously in this disclosure. Main body 20k further includes a forward rim 42k formed as part of forward end potion 22k and which defines front opening 30k.

Shield 14k is typically a generally cylindrical, hollow structure comprising a shield body 50k having a distal or forward end 52k and a proximal or rearward end 54k, and defines an internal cavity or bore 56k extending therethrough. Forward end 52k of shield body 50k defines a partial forward end wall or rim 58k defining a forward opening 60k, through which a puncturing element of lancet 70k extends when lancet device 10k is actuated by a user. Forward end wall 58k typically defines a small contact area about forward opening 60k for contacting an intended puncture area on a patient's body. The reduced contact area may be made smaller (i.e., reduced in surface area) by providing a plurality of peripheral indentations (not shown) formed perimetrically in shield 14k. The external surface features of housing 12k and shield 14k may be formed in accordance with the ergonomic features and structure disclosed in application Ser. No. 11/123,849 incorporated by reference previously in this disclosure. Rearward end 54k of shield body 50k defines a rear rim 63k.

Shield 14k is typically axially and slidably movable within housing 12k. Shield 14k and housing 12k may be coaxially associated, with shield 14k and housing 12k coaxially disposed around a common Central Axis A. Shield 14k and housing 12k may each be generally cylindrical-shaped. A rotation element or cam follower, typically a guide plate 262 is further associated with shield 14k. In particular, guide plate 262 is disposed at the rearward end 54k of shield body 50k and engages rear rim 63k of shield body 50k. Plate 262 is a generally annular-shaped structure and defines a central opening 263 with two opposed clearance slots 264 and two opposed guide slots 266. Clearance slots 264 and guide slots 266 are orientated along axes that are generally orthogonal to one another. An outer periphery or perimeter of plate 262 is formed with two opposed cam guide recesses 268 for receiving and engaging a cam structure adapted to cause rotation of plate 262 to cause actuation of lancet device 10k as described further herein. Plate 262 is typically in rotational sliding engagement or contact with rear rim 63 of shield body 50k to permit rotation thereof relative to rear rim 63. In particular, plate 262 comprises a bottom side 270 in contact with rear rim 63k and an upper side 272 facing away from rear rim 63k. Due to the contact between the bottom side 270 of plate 262 and rear rim 63, plate 262 is adapted to slide together with shield body 50k in main body 20k when axial motion is imparted to shield body 50k, for example by axially retracting (i.e., depressing) shield body 50k into main body 20k to actuate lancet device 10k as described herein. Accordingly, any axial motion applied to shield body 50k to retract (i.e., depress) shield body 50k into main body 20k of housing 12k will be transmitted to plate 262 through the contact engagement of rear rim 63k and plate 262.

Lancet device 10k further comprises a lancet 70k disposed within the housing 12k, and extending into shield 14k. Lancet 70k includes a puncturing element shown in the form of a lancet 72k. Lancet 72k comprises a puncturing end 74k at the forward end thereof. Lancet 70k is generally adapted for axial movement through the internal cavity 56k of shield body 50k between an initial position, wherein the puncturing end 74k is disposed within shield body 50k, to a puncturing position wherein the puncturing end 74k extends beyond the forward opening 60k of shield body 50k a sufficient distance to cause a puncture wound in a patient's body. The puncturing end 74k of lancet 72k is adapted for puncturing the skin of a patient, and may be in the form of a pointed end, needle tip, blade edge, and the like. Puncturing end 74k may include a preferred alignment orientation, such as with a pointed end or a blade aligned in a specific orientation. In such an orientation, shield body 50k and/or main body 20k of housing 12k may include target indicia corresponding to the alignment orientation of puncturing end 74k. Indentations (not shown) in the shield body 50k and/or indentations (not shown) in main body 20k may function as such an alignment orientation, as described previously in this disclosure.

Lancet 70k comprises a carrier body 76k supporting lancet 72k at the rearward end thereof. Carrier body 76k and shield body 50k may include corresponding guiding surfaces for guiding the movement of lancet 70k in shield body 50k. For example, carrier body 76k may include guide tabs 78k on an external surface thereof, with shield body 50k defining corresponding guide channels 80k extending longitudinally along an inner wall thereof for accommodating guide tabs 78k slidably therein upon actuation of lancet device 10k. Carrier body 76k may include a pair of elongated guide tabs 78k on opposing lateral sides thereof as illustrated, or a single elongated guide tab 78k, and shield body 50k may include a corresponding pair of guide channels 80k extending along opposing inner surfaces thereof corresponding to each of the guide tabs 78k, or a single corresponding guide channel 80k. The engagement of guide tabs 78k in guide channels 80k in the initial, pre-actuated state of lancet device 10k ensures that lancet 70k is prevented from substantial rotation in shield body 50k during the actuation sequence of lancet device 10k, wherein plate 262 is set into sliding rotational movement relative to rear rim 63k as described herein. Upon actuation, engagement of guide tabs 78k in guide channels 80k guides movement of lancet 70k to the puncturing position.

Figure 60:
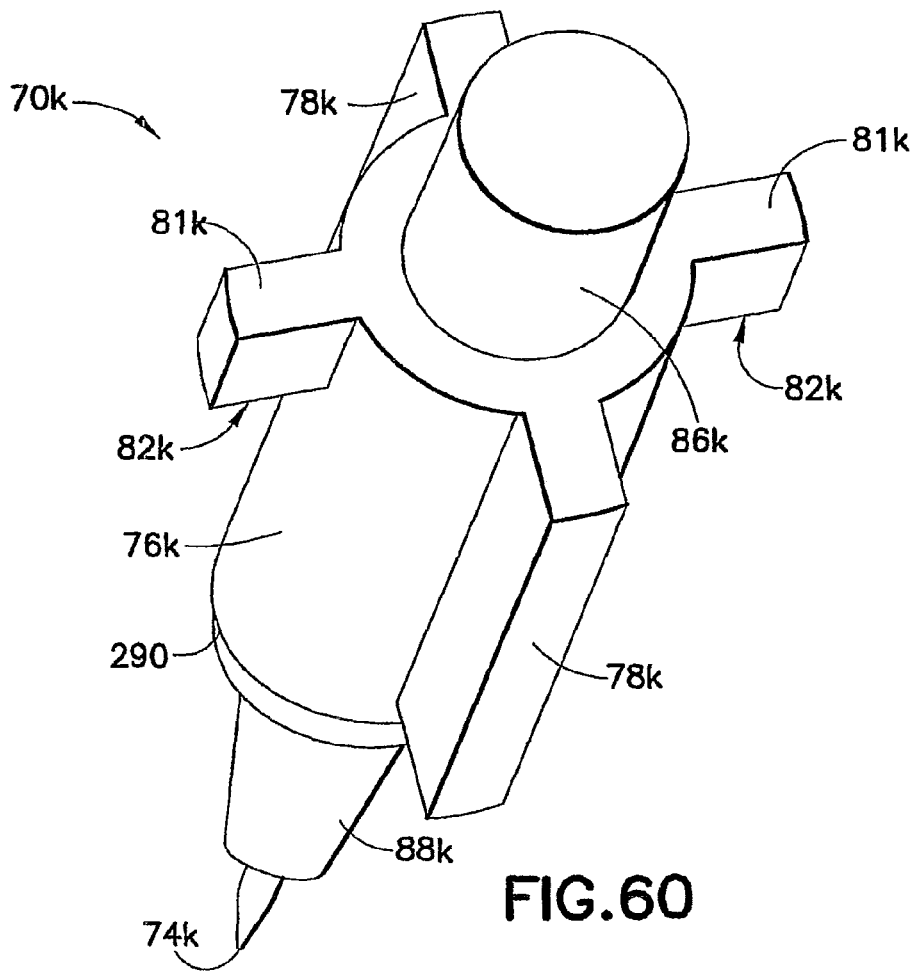
FIG. 60 is a perspective view of a lancet used in the lancet device of FIG. 56.

As shown in FIG. 60, in addition to two opposed guide tabs 78k, carrier body 76k further comprises two actuation tabs 81k oriented along an axis generally orthogonal to an axis passing through guide tabs 78k. Actuation tabs 81k form part of the actuation structure or actuator of lancet device 10k. Actuation tabs 81 are shorter in length than guide tabs 78k, which typically extend approximately the length of carrier body 76k. Actuation tabs 81k comprise a distal facing surface 82k adapted to engage or rest upon the upper side 270 of guide plate 262 in the initial, pre-actuated state of lancet 70k. Actuation tabs 81k are generally adapted to mate or align with clearance slots 264 in plate 262 when plate 262 is rotated to the appropriate alignment position with actuation tabs 81k to allow actuation of lancet device 10k as described herein. Likewise, guide tabs 78k are sized to mate with guide slots 266 in plate 262. However, guide tabs 78k generally extend at least partially through guide slots 266 in the initial, pre-actuated state of lancet device 10k, and the guide slots 266 are typically sized larger enough to allow plate 262 to rotate relative to carrier body 76k without guide tabs 78k interfering with such rotation due to their presence in guide slots 266.

Shield body 50k may define additional internal guide channels 84k for receiving actuation tabs 81k when the interference engagement between actuation tabs 81k and plate 262 is removed by rotation of plate 262. Such additional guide channels 84k are optional as the association of guide tabs 78k and guide channels 84k is typically sufficient to guide the movement of carrier body 76k during the puncturing movement of lancet 70k. If provided, additional guide channels 84k may extend the internal length of shield body 50k or along only a portion of the length of shield body 50k. Carrier body 76k further comprises a proximal or rearward end spring guide 86k and a distal or forward end spring guide 88k for engaging a drive spring and retraction spring, respectively, of lancet device 10k as described herein. Spring guides 86k, 88k may be formed integral with the carrier body 76k or be provided as distinct, separate elements in the manner described previously in this disclosure.

Movement of the lancet 70k through the lancet device 10a is achieved through a biasing force provided by a drive spring 92k. Drive spring 92k is adapted to exert a biasing force against lancet 70k to drive lancet 70k through lancet device 10k toward the puncturing position, and is disposed between the rearward end of main body 20k and the lancet 70k. Rear cap 24k may include structure for alignment of and/or for maintaining drive spring 92k in the proper orientation on rear cap 24k. For example, rear cap 24k may include an internal alignment structure (not shown) for correctly positioning the drive spring 92k. Lancet 70k, as indicated previously, includes proximal spring guide 86k which engages the opposite end of drive spring 92k in the initial or pre-actuated state of lancet device 10k. Guide tabs 78k and actuation tabs 81k may be used as additional or replacement structure for engaging the distal end of drive spring 92k.

In the initial state of lancet device 10k, drive spring 92k is typically in a generally uncompressed, unloaded state between rear cap 24k and distal spring guide 86k of carrier body 76k. However, drive spring 92k may exert a limited forward biasing or positioning force on carrier body 76k via proximal spring guide 86k to help maintain the interference engagement between actuation tabs 81k and plate 262. Alternatively, drive spring 92k may be partially compressed between rear cap 24k and carrier body 76k and is adapted for further compression therebetween. During actuation of lancet device 10k, the retraction of shield body 50k into main body 20k causes compression or further compression of drive spring 92k due to the interference engagement between lancet 70k and plate 262, thereby storing potential energy in drive spring 92k necessary to bias lancet 70k to the puncturing position. As shield body 50k is further retracted into main body 20k, the rotation of plate 262 relative to lancet 70k eventually removes the interference engagement between actuation tabs 81k and plate 262, thereby releasing the potential energy stored in compressed drive spring 92k as kinetic energy applied to lancet 70k to bias lancet 70k to the puncturing position.

A retraction or return spring 94k may further be provided at the forward end of the lancet device 10k, for retracting the lancet 70k within shield body 50k after lancet 70k has moved axially to the puncturing position wherein puncturing element 74k extends outward from the distal or forward end 52k of shield body 50k. Retraction spring 94k is adapted to be engaged by distal spring guide 88k extending forward from carrier body 76a during the forward, puncturing movement of lancet 70k, as described herein. The forward end wall 58k of shield body 50k forms a distal end pocket 98k for receiving and supporting retraction spring 94k. Retraction spring 94k is disposed in distal end pocket 98k throughout the operation sequence of lancet device 10a in a puncturing procedure. Retraction spring 94k may be secured to the internal side of the forward end wall 58k of shield body 50k through use of a medical grade adhesive or by mechanically securing retraction spring 94k thereto in the manner described previously in this disclosure. Drive and retraction springs 92k, 94k are typically compression springs capable of storing potential energy when in a compressed state. Lancet device 10k may further include a protective tab or cover 100k for protectively covering the forward end of the lancet 70k as described in previous embodiments. The respective elements of the lancet device 10k are all typically formed of molded plastic material, such as a medical grade plastic material. Lancet 72k may be constructed of any suitable material adapted for puncturing the skin, and is typically a surgical grade metal such as stainless steel.

Rear cap 24k of housing 12k further comprises internal structure adapted to interact with plate 262 to cause actuation of lancet device 10k. In particular, rear cap 24k is formed with at least one and typically two distally-extending actuation members typically cam elements 280 each having a tapered cam surface 282 formed on their distal ends. Cam elements 280 are formed to extend distally into the respective cam guide recesses 268 in plate 262. The cam interaction between cam elements 280 and plate 262 provides the means by which the interference engagement between the lancet 70k and plate 262 is removed to allow lancet 70k to move to the puncturing position. More particularly, the interaction between the tapered cam surfaces 282 on cam elements 280 and cam guide recesses 268 in plate 262 during the retracting movement of shield body 50k into main body 20k causes sufficient rotational movement of plate 262 relative to carrier body 76k to allow actuation tabs 81k to align with clearance slots 264 in plate 262 to remove the interference engagement between lancet 70k and plate 262. As indicated previously, such rotational movement of plate 262 is sliding rotational movement on rear rim 63k of shield body 50k. Also as indicated previously, guide slots 266 in plate 262 are preferable sized sufficiently to allow plate 262 to rotate to the alignment position without guide tabs 78k interfering with such rotation.

Figure 62:
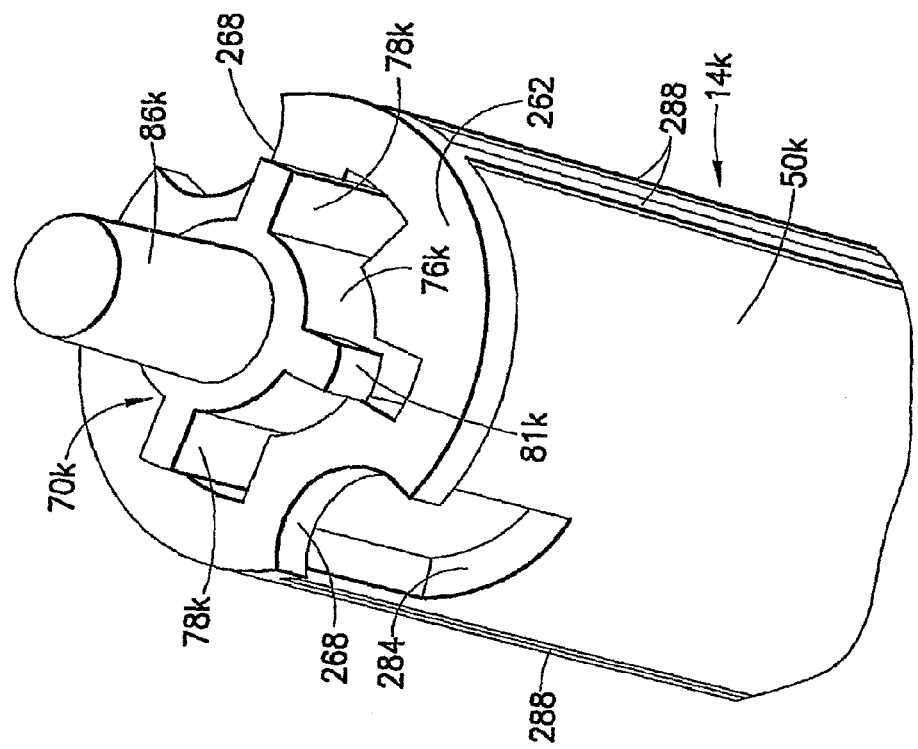
FIG. 62 is a side view of the assembled structure shown in FIG. 61 additionally including the rear cap shown in FIG. 59.
Figure 61:
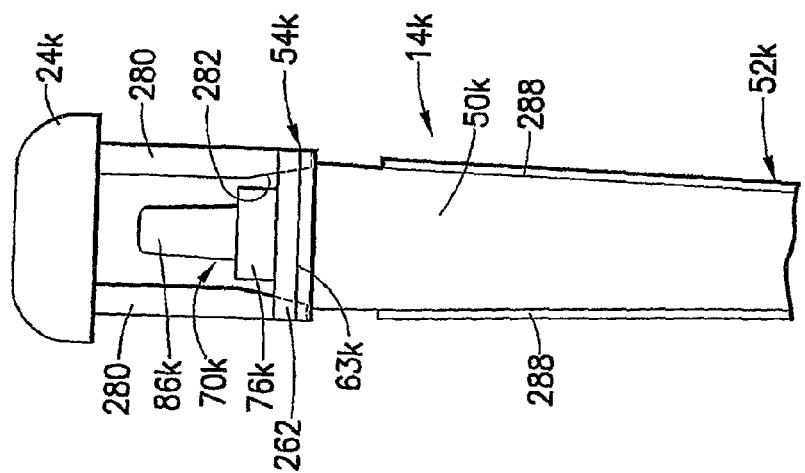
FIG. 61 is a perspective view of a rearward portion of the lancet of FIG. 60 showing the lancet associated with the shield and guide plate shown in FIG. 59.
Figure 63:
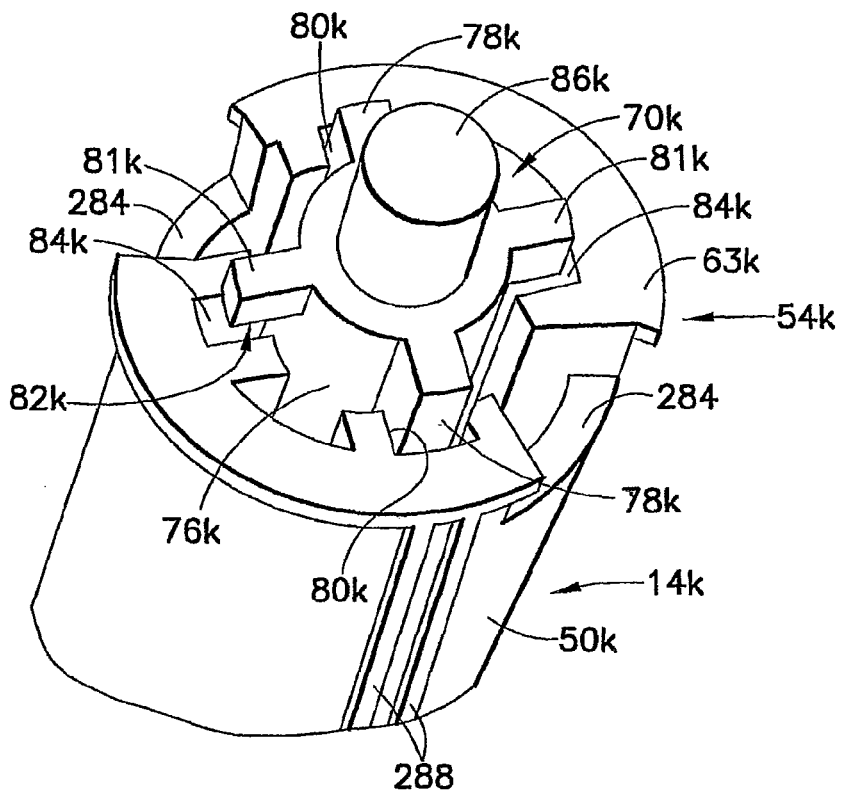
FIG. 63 is a perspective view of a rearward end of a shield with a lancet movable through the shield in accordance with the lancet device of FIG. 56.
Figure 64:
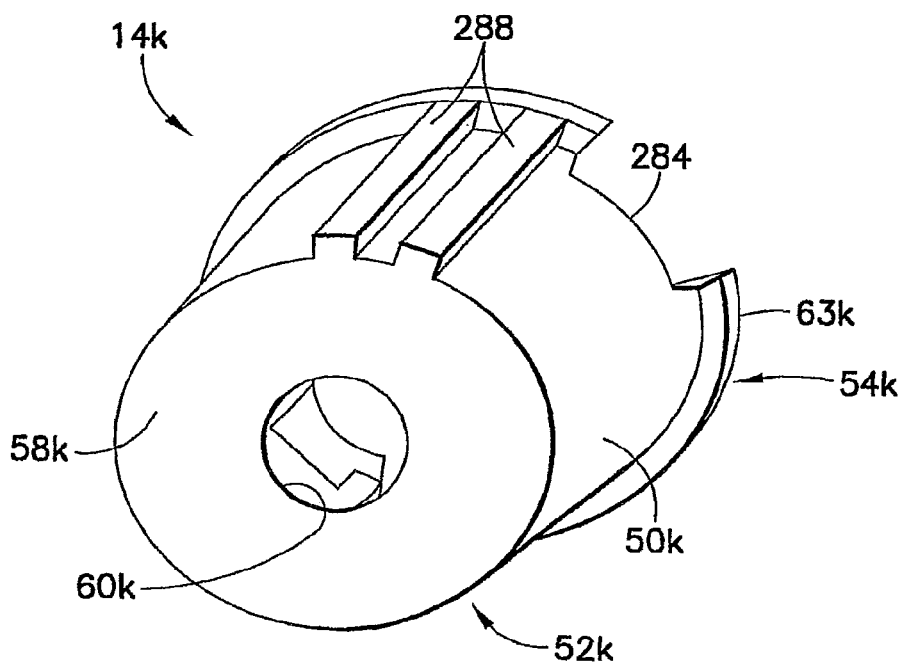
FIG. 64 is a perspective view of a forward end of the shield of the lancet device of FIG. 56.

Due to the elongated length of cam elements 280, shield body 50k defines opposed cut-outs or notches 284 to accommodate the distal tips of cam elements 280 extending through cam guide recesses 268 in the initial, pre-actuated state of lancet device 10k, and the eventual forward position of the distal tips of cam elements 280 as shield body 50k is retracted into main body 20k to cause actuation of lancet device 10k. Cam guide recesses 268 are initially offset from notches 284 but as plate 262 is rotated to the alignment position cam guide recesses 268 eventually align with notches 284 as shown in FIG. 62. The engagement of cam elements 280 with plate 262 in cam guide recesses 268 provides an additional advantage of maintaining or locking the orientation of plate 262 on rear rim 63k of shield body 50k. Thus, plate 262 will be prevented or inhibited from disengaging from and falling off of rear rim 63k should lancet device 10k be turned upside down (i.e., shield 14k pointed upward) prior to use. Additional structure extending from rear cap 24k or internally from the inner wall of main body 20*k* of housing 12*k* may be provided to maintain the positioning of plate 262 on rear rim 63*k* of shield body 50*k*.

Additionally, in order to prevent the possibility of rotational motion imparted to plate 262 by cam elements 280 from being transmitted to shield body 50*k*, shield body 50*k* may comprise longitudinally-extending outer ribs 288 which are adapted to cooperate with interfering structure on the inner wall of main body 20*k*, such as an engaging tab or detent (not shown). The engagement of such a tab or detent with ribs 288 will substantially lock the orientation of shield body 50*k* relative main body 20*k* and prevent rotation of shield body 50*k* relative to main body 20*k*. Moreover, engagement ribs 288 may be used as guiding structure to guide the retracting movement of shield body 50*k* into main body 20*k* during actuation of lancet device 10*k*. Shield body 50*k* further defines an abutment shoulder 290 at forward end 52*k*. Abutment shoulder 290 is adapted for interference engagement with forward rim 42*k* of main body 20*k* to prevent shield body 50*k* and, thus, lancet 70*k* from axial forward movement out of main body 20*k* through front opening 30*k*. Additionally, the limited positioning or biasing force of drive spring 92*k* on lancet 70*k* in the initial, pre-actuated state of lancet device 10*k* is transmitted through the interference engagement between plate 262 and shield body 50*k* to shoulder 290, which then engages forward rim 42*k*.

Use and actuation of lancet device 10*k* will now be described with continued reference to FIGS. 56-67. Lancet device 10*k* is typically initially provided with cover 100*k* extending distally from carrier body 76*k*, and through forward opening 60*k* in forward end wall 58*k* of shield body 50*k*. In the initial, pre-actuated state of lancet device 10*k*, drive spring 92*k* is typically uncompressed between the inner side of rear cap 24*a* and proximal spring guide 86*k* of carrier body 76*a*, and lancet 70*k* is initially in interference engagement with plate 262, for example under the limited position or biasing force provided by drive spring 92*k*. In particular, actuation tabs 81*k* extending from carrier body 76*k* rest upon the upper side 270 of plate 262 and are offset from mating clearance slots 264 in plate 262. Further, in the initial, pre-actuated state of lancet device 10*k*, guide tabs 78*k* are disposed in guide channels 80 in shield body 50*k*, and extend proximally through guide slots 266 in plate 262. As indicated previously, the engagement of guide tabs 78*k* in guide channels 80*k* prevents rotation of lancet 70*k* in shield body 50*k* and, more particularly, carrier body 76*k* in shield body 50*k* during the rotational movement of plate 262 used to release the interference engagement between actuation tabs 81*k* and plate 262, as described herein. Cam elements 280 extending distally from rear cap 24*k* extend at least partially through the respective cam guide recesses 268 defined in the periphery of plate 262. Typically, the tapered cam surfaces 282 of cam elements 280 contact plate 262 within cam guide recesses 268 to allow cam elements 280 to effect the rotational movement of plate 262 when shield body 50*k* is retracted (i.e., depressed) into main body 20*k*, and secondarily to maintain plate 262 associated with rear rim 63*k* of shield body 50*k*. As described previously, guide slots 266 in plate 262 are sized to accommodate guide tabs 78*k* and to allow plate 262 to rotate relative carrier body 76*k* without guide tabs 78*k* interfering with such rotational movement necessary to allow actuation tabs 81*k* into alignment with clearance slots 264 in plate 262. In this initial, pre-actuated state of lancet device 10*k*, cam guide recesses 268 are offset from notches 284 in shield body 50*k* with the only the distal tips of cam elements 280 extending through cam guide recesses 268 as shown in FIG. 65B.

To use the lancet device 10*k*, the user grasps opposing sides of housing 12*k*, such as between a finger and thumb, and removes breakable cover 100*k*. Cover 100*k* is removed typically by moving cover 100*k* in a combined twisting and pulling motion in forward opening 60*k* in forward end wall 58*a* of shield body 50*k* to break the frangible connection with carrier body 76*k*. Once the frangible connection is broken, cover 100*k* may be removed through the forward opening 60*k*. Forward end wall 58*k* of shield body 50*k* may then be placed in contact with a location on the patient's body where it is desired to cause a puncture injury to initiate blood flow. If provided, target indicia may be aligned with the desired location of puncture.

Figure 66A:
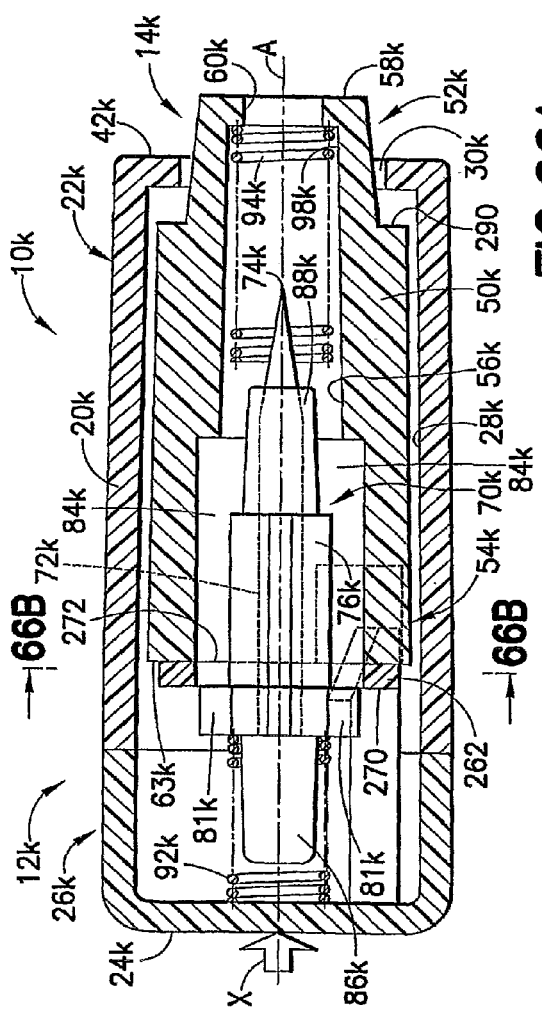
FIGS. 66A and 66B are longitudinal and transverse cross-sectional views, respectively, of the lancet device of FIG. 56 showing the lancet device in an initial stage of actuation.
Figure 66B:
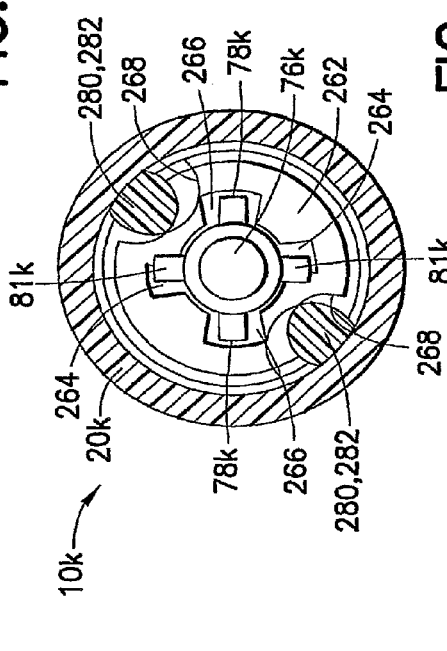

Once placed against the body, the user exerts a downwardly directed force on main body 20*k* of housing 12*k* forcing shield body 50*k* of shield 14*k* to retract (i.e., depress) into housing 12*k*. In particular, the user applies a downward directed force in the direction of Arrow X, thereby applying a force against the user's body (i.e., skin surface). Such force establishes an opposing force on forward end wall 58*k* of shield body 50*k* causing shield body 50*k* to retract axially within main body 20*k* of housing 12*k*. As shield body 50*k* retracts into main body 20*k*, rearward end 54*k* of shield body 50*k* moves proximally (i.e., rearward) toward rear cap 24*k*. The engagement between rear rim 63*k* at the rearward end 54*k* of shield body 50*k* and plate 262 causes plate 262 to move together with shield body 50*k* toward rear cap 24*k*. As the entire lancet 70*k* moves rearward due to the interference engagement between actuation tabs 81*k* and plate 262, drive spring 92*k* begins to compress or compresses further between rear cap 24*k* and carrier body 76*k* and, more particularly, between proximal spring guide 86*k* and rear cap 24. Substantially simultaneously, cam elements 280 interact with plate 262 in cam guide recesses 268 in plate 262, and act upon plate 262 to cause plate 262 to slidably rotate on rear rim 63 of shield body 50*k*. In particular, as shield body 50*k* moves proximally, tapered cam surfaces 282 on cam elements 280 engage plate 262 in cam guide recesses 268 causing plate 262 to rotate. The tapered form of tapered cam surface 282 converts the linear retraction motion imparted to shield body 50*k* to rotational movement of plate 262. The engagement of guide tabs 78*k* in guide channels 80*k* prevents lancet 70*k* and carrier body 76*k* in particular from rotating in shield body 50*k*. As shown in FIG. 66B, the distal ends of cam elements 280 project further through cam guide recesses 268 as cam elements 280 rotate plate 262 toward the release position where actuation tabs 81*k* align with clearance slots 264 in plate 262.

As the entire lancet 70*k* continues move rearward due to the interference engagement between actuation tabs 81*k* and plate 262, drive spring 92*k* continues to compress between rear cap 24*k* and proximal spring guide 86*k*, and am elements 280 continue to rotate plate 262 on rear rim 63*k* of shield body 50*k*. Eventually, plate 262 rotates to the release position where actuation tabs 81*k* align with clearance slots 264 in plate 262, as shown in FIG. 67B. When this occurs, the interference engagement between actuation tabs 81*k* and plate 262 is released. At the moment the actuation tabs 81*k* align with clearance slots 264, the restraining force applied to drive spring 92*k* due to the interference engagement between actuation tabs 81*k* and plate 262 is released, releasing the stored potential energy in drive spring 92*k* as kinetic energy used to move lancet 70*k* forward in shield body 50*k*. With the stored potential energy in compressed drive spring 92*k* released as kinetic energy, drive spring 92*k* biases lancet 70*k* away from rear cap 24*k* and through internal cavity 56*k* in shield body 50*k*. During such movement, corresponding guide tabs 78k and guide channels 80k guide lancet 70k axially through shield body 50k. The biasing force acting on lancet 70k is preferably sufficient to cause the puncturing end 74k of lancet 72k to project a sufficient distance and with sufficient force from the forward opening 60k in shield body 50k to cause a puncture wound in the desired location on a patient's body. Moreover, during the propelling axial movement of lancet 70k, proximal spring guide 86k on carrier body 76k of lancet 70k releases from drive spring 92k which remains connected to rear cap 24k. In lancet device 10k, lancet 70k is limited to axial movement only with respect to shield 14k and housing 12k.

Moreover, as lancet 70k moves forward in the propelling movement, distal spring guide 88k engages the rearward end of retraction spring 94k. The biasing force provided by drive spring 92k is at least in part applied to retraction spring 94k by engagement of distal spring guide 88k with the rearward end of retraction spring 94a which causes retraction spring 94k to compress toward distal end pocket 98k and store potential energy. Retraction spring 94k is designed such that it may be compressed in whole or in part by the biasing force of drive spring 92k propelling lancet 70k, but still permits puncturing end 74k of lancet 72k to extend through forward opening 60k in shield body 50k a sufficient distance and with sufficient force to puncture the skin of the patient and initiate blood flow. Guide channels 84k associated with actuation tabs 81k may be formed with abutment surfaces for engagement by actuation tabs 81k during the forward movement of lancet 70k to prevent lancet 70k from axial movement entirely out of shield body 50k through forward or front opening 60k. Alternatively, carrier body 76k and/or distal spring guide 88k may be adapted for interference engagement with forward end wall 58 of shield body 50k to prevent lancet 70k from axial movement entirely out of shield body 50k through forward or front opening 60k As indicated previously, retraction spring 94k is typically a compression spring and will have sufficient resilience to return to a relaxed, unloaded state within shield body 50k after the lancet 70k extends to the puncturing position. Accordingly, once the retraction spring 94k is compressed it will provide a return biasing force on the lancet 70k by engagement with the distal spring guide 88k on carrier body 76k. Retraction spring 94k thereby acts between the forward end wall 58k of the shield body 50a and distal spring guide 88k on carrier body 76k to cause complete retraction of lancet 70k into shield body 50k. In particular, retraction spring 94k applies a return biasing force that retracts the puncturing end 74k of lancet 72k entirely within shield body 50k. Moreover, as the retraction spring 94k returns to a relaxed or unloaded state within shield body 50k, lancet 70k is returned to a static position within shield body 50k, wherein lancet 70k is disposed at a relatively fixed and stationary position within shield body 50. Once retraction spring 94k returns to a relaxed or uncompressed state, retraction spring 94k maintains lancet 70k disposed within the shield body 50k with puncturing end 74k shielded within shield body 50k, and prevents further movement of lancet 70k toward the puncturing position.

While the invention was described with reference to several distinct embodiments of the lancet device, those skilled in the art may make modifications and alterations to the invention without departing from the scope and spirit of the invention. Accordingly, the above detailed description is intended to be illustrative rather than restrictive. The invention is defined by the appended claims, and all changes to the invention that fall within the meaning and range of equivalency of the claims are to be embraced within their scope.

What is claimed is:

1. A lancet device, comprising:
a housing having a rearward end, a forward end, and a side portion;
a shield movably associated with the housing, the shield comprising a rearward end, a forward end, a central passageway extending between the rearward end and the forward end, and at least one guide channel defined within an interior of the shield and extending between the rearward end and the forward end;
a lancet disposed in the housing and comprising a tip and at least one guide tab configured to slidably move within the at least one guide channel of the shield, the lancet adapted for axial movement between a first position where the tip is disposed within the shield and a second position where the tip extends through a forward opening in the shield;
a drive member disposed at the rearward end of the housing for biasing the lancet to the second position; and
an actuator associated with the housing and engaged with the lancet to maintain the lancet in the first position,
wherein movement of the shield into the housing causes disengagement of the actuator from the lancet and release of the drive member thereby enabling the drive member to bias the lancet to the second position.

2. The lancet device of claim 1, wherein the drive member comprises a coil spring positioned between a surface of the housing and the lancet.

3. The lancet device of claim 1, wherein the actuator maintains the drive member in an at least partially compressed state.

4. The lancet device of claim 1, wherein the shield is at least partially disposed within the housing.

5. The lancet device of claim 4, wherein the shield is configured to move into the housing during use of the lancet device.

6. The lancet device of claim 1, wherein the actuator is generally annular.

7. The lancet device of claim 6, wherein the actuator further comprises a surface that engages a part of the lancet to maintain the lancet in the first position.

8. The lancet device of claim 7, wherein the surface is annularly discontinuous.

9. The lancet device of claim 1, wherein a portion of the actuator is disposed between the shield and the side portion of the housing at an angle orthogonal to the longitudinal axis of the lancet device.

10. The lancet device of claim 1, wherein the portion of the actuator extends in a direction from a distal end of the lancet device to a proximal end of the lancet device with a longitudinal axis of the portion of the actuator extending substantially parallel with a longitudinal axis of the housing.

11. The lancet device of claim 1, wherein the rearward end of the shield contacts the actuator.

12. The lancet device of claim 1, wherein the at least one guide channel comprises at least two guide channels, and wherein the at least one guide tab comprises at least two guide tabs.

13. The lancet device of claim 1, wherein a portion of the actuator extends past the rearward end of the shield in a direction towards the forward end of the housing, the same portion of the actuator being disposed between the shield and the side portion of the housing.

* * * * *